United States Patent
Jiang et al.

(10) Patent No.: US 9,790,269 B2
(45) Date of Patent: Oct. 17, 2017

(54) TRANSTHYRETIN ANTIBODIES AND USES THEREOF

(71) Applicant: MISFOLDING DIAGNOSTICS, INC., San Diego, CA (US)

(72) Inventors: Xin Jiang, San Diego, CA (US); Jeffery W. Kelly, La Jolla, CA (US); Justin Chapman, San Diego, CA (US)

(73) Assignee: MISFOLDING DIAGNOSTICS, INC., San Diego, CA (US)

( * ) Notice: Subject to any disclaimer, the term of this patent is extended or adjusted under 35 U.S.C. 154(b) by 0 days.

(21) Appl. No.: 14/760,194

(22) PCT Filed: Feb. 7, 2014

(86) PCT No.: PCT/US2014/015421
§ 371 (c)(1),
(2) Date: Jul. 9, 2015

(87) PCT Pub. No.: WO2014/124334
PCT Pub. Date: Aug. 14, 2014

(65) Prior Publication Data
US 2016/0039916 A1    Feb. 11, 2016

Related U.S. Application Data

(60) Provisional application No. 61/863,818, filed on Aug. 8, 2013, provisional application No. 61/762,750, filed on Feb. 8, 2013.

(51) Int. Cl.
*C07K 16/18* (2006.01)

(52) U.S. Cl.
CPC .......... *C07K 16/18* (2013.01); *C07K 2317/34* (2013.01); *C07K 2317/92* (2013.01)

(58) Field of Classification Search
CPC . C07K 16/18; C07K 2317/34; C07K 2317/92
See application file for complete search history.

(56) References Cited

U.S. PATENT DOCUMENTS

| | | | |
|---|---|---|---|
| 4,816,567 A | 3/1989 | Cabilly et al. |
| 4,844,904 A | 7/1989 | Hamaguchi et al. |
| 4,863,740 A | 9/1989 | Kissel et al. |
| 4,975,282 A | 12/1990 | Cullis et al. |
| 5,000,959 A | 3/1991 | Iga et al. |
| 5,405,783 A | 4/1995 | Pirrung et al. |
| 5,412,087 A | 5/1995 | McGall et al. |
| 5,445,934 A | 8/1995 | Fodor et al. |
| 5,459,127 A | 10/1995 | Felgner et al. |
| 5,501,979 A | 3/1996 | Geller et al. |
| 5,561,063 A | 10/1996 | Hock et al. |
| 5,604,090 A | 2/1997 | Alexander et al. |
| 5,624,820 A | 4/1997 | Cooper |
| 5,658,753 A | 8/1997 | Paul et al. |
| 5,665,577 A | 9/1997 | Sodroski et al. |
| 5,674,703 A | 10/1997 | Woo et al. |
| 5,693,508 A | 12/1997 | Chang |
| 5,695,937 A | 12/1997 | Kinzler et al. |
| 5,700,470 A | 12/1997 | Saito et al. |
| 5,719,054 A | 2/1998 | Boursnell et al. |
| 5,731,172 A | 3/1998 | Saito et al. |
| 5,786,340 A | 7/1998 | Henning et al. |
| 5,821,235 A | 10/1998 | Henning et al. |
| 5,861,397 A | 1/1999 | Wheeler |
| 5,928,944 A | 7/1999 | Seth et al. |
| 6,001,331 A | 12/1999 | Caprathe et al. |
| 6,013,516 A | 1/2000 | Verma et al. |
| 6,110,456 A | 8/2000 | During |
| 7,029,655 B2 | 4/2006 | Allen et al. |
| 7,053,116 B2 | 5/2006 | Schubert et al. |
| 7,205,136 B1 | 4/2007 | Schochetman et al. |
| 7,214,695 B2 | 5/2007 | Kelly et al. |
| 7,214,696 B2 | 5/2007 | Kelly et al. |
| 7,250,496 B2 | 7/2007 | Bentwich |
| 7,311,893 B2 | 12/2007 | Gervais et al. |
| 7,425,318 B2 | 9/2008 | Kung et al. |
| 7,560,488 B2 | 7/2009 | Kelly et al. |
| 7,659,299 B2 | 2/2010 | Pepys et al. |
| 7,700,616 B2 | 4/2010 | Tamagnan et al. |
| 7,749,697 B2 | 7/2010 | Oleksiewicz et al. |
| 7,868,033 B2 | 1/2011 | Labaudiniere |
| 7,901,683 B2 | 3/2011 | Griswold-Prenner et al. |
| 7,910,332 B2 | 3/2011 | Nielsen et al. |
| 8,101,743 B2 | 1/2012 | Brown-Driver et al. |

(Continued)

FOREIGN PATENT DOCUMENTS

| EP | 1583830 B1 | 9/2006 |
|---|---|---|
| EP | 2152872 B1 | 9/2010 |

(Continued)

OTHER PUBLICATIONS

Bergstrom J et al. Surface exposed epitopes and structural heterogeneity of in vivo formed transthyretin amyloid fibrils. Biochem. Biophys. Res. Comm. 2006, 348:532-539.*
Gustaysson A et al. Mechanisms of transthyretin amyloidogenesis; Antigenic mapping of transthyretin purified from plasma and amyloid fibrils and within in situ tissue localizations. Am. J. Pathol. 1994, 144(6):1301-1311.*
Obayashi K et al. Impact of antibodies against amyloidogenic transthyretin (ATTR) on phenotypes of patients with familial amyloidotic polyneuropathy (FAP) ATTR Valine30Methionine. Clina Chimica Acta, 2013, 419:127-131.*
Sharma S et al. Identification of autoantibodies against transthyretin for the screening and diagnosis or rheumatoid arthritis. PLoS One, 2014, 9(4):e93905.*
Abcam, KD Value: A quantitative measurement of antibody affinity. From www.abcam.com/primary-antibodies/kd-value-a-quantitive-measurement-of-antibody-affinity; Retrieved Dec. 8, 2016.*

(Continued)

*Primary Examiner* — Kimberly A. Ballard
(74) *Attorney, Agent, or Firm* — Wilson Sonsini Goodrich & Rosati

(57) ABSTRACT

The present invention provides compositions comprising anti-transthyretin antibodies. The compositions are particularly useful for diagnosis, prognosis and/or treatment of amyloid diseases or symptoms thereof.

19 Claims, 16 Drawing Sheets

(56) References Cited

U.S. PATENT DOCUMENTS

| | | | |
|---|---|---|---|
| 8,168,775 | B2 | 5/2012 | Sah et al. |
| 8,283,460 | B2 | 10/2012 | Ge et al. |
| 8,653,080 | B2 | 2/2014 | Dillin et al. |
| 9,101,643 | B2 | 8/2015 | Sah |
| 2006/0035946 | A1 | 2/2006 | Huang et al. |
| 2006/0079578 | A1 | 4/2006 | Laurin et al. |
| 2006/0135460 | A1 | 6/2006 | Ridder et al. |
| 2007/0037875 | A1 | 2/2007 | Kelly et al. |
| 2007/0111258 | A1 | 5/2007 | Kaufman et al. |
| 2009/0123373 | A1 | 5/2009 | Wang et al. |
| 2010/0159486 | A1* | 6/2010 | Liotta ............... G01N 33/6896 435/7.92 |
| 2010/0233176 | A1* | 9/2010 | Cashman ............. G06F 19/16 424/139.1 |
| 2014/0056904 | A1* | 2/2014 | Chakrabartty ........ C07K 16/26 424/139.1 |

FOREIGN PATENT DOCUMENTS

| | | |
|---|---|---|
| JP | 2010195710 A | 9/2010 |
| WO | WO 92/05266 A2 | 4/1992 |
| WO | WO 92/14829 A1 | 9/1992 |
| WO | WO 2004/061104 A2 | 7/2004 |
| WO | WO 2006/007853 A2 | 1/2006 |
| WO | WO 2008/141074 A1 | 11/2008 |
| WO | WO 2008/145133 A2 | 12/2008 |
| WO | WO 2009/065414 A1 | 5/2009 |
| WO | WO 2010/030203 A1 | 3/2010 |
| WO | WO 2010/048228 A2 | 4/2010 |
| WO | WO 2011/100396 A2 | 8/2011 |
| WO | WO 2011/123468 A1 | 10/2011 |
| WO | WO 2011/140333 A1 | 11/2011 |

OTHER PUBLICATIONS

Su Y et al. Antibody therapy for familial amyloidotic polyneuropathy. Amyloid, 2012, 19(S1):45-46.*

Adams, et al. The course and prognostic factors of familial amyloid polyneuropathy after liver transplantation. Brain. Jul. 2000;123 ( Pt 7):1495-504.

Adamski-Werner, et al. Diflunisal analogues stabilize the native state of transthyretin. Potent inhibition of amyloidogenesis. J Med Chem. Jan. 15, 2004;47(2):355-74.

Alhamadsheh, et al. Potent kinetic stabilizers that prevent transthyretin-mediated cardiomyocyte proteotoxicity. Sci Transl Med. Aug. 24, 2011;3(97):97ra81. doi: 10.1126/scitranslmed. 3002473.

Ando, et al. Transthyret in-related familial amyloidotic polyneuropathy. Archives of Neurology, vol. 62, No. 7, pp. 1057-1062 (2005).

Andrade. A peculiar form of peripheral neuropathy; familiar atypical generalized amyloidosis with special involvement of the peripheral nerves. Brain. Sep. 1952;75(3):408-27.

Balch, et al. Adapting proteostasis for disease intervention. Science. Feb. 15, 2008;319(5865):916-9. doi: 10.1126/science.1141448.

Banerji, et al. A lymphocyte-specific cellular enhancer is located downstream of the joining region in immunoglobulin heavy chain genes. Cell. Jul. 1983;33(3):729-40.

Bartalena, et al. Thyroid hormone transport proteins. Clin Lab Med. Sep. 1993;13(3):583-98.

Baures, et al. Discovering transthyretin amyloid fibril inhibitors by limited screening. Bioorg Med Chem. Aug. 1998;6(8):1389-401.

Baures, et al. Synthesis and evaluation of inhibitors of transthyretin amyloid formation based on the non-steroidal anti-inflammatory drug, flufenamic acid. Bioorg Med Chem. Jul. 1999;7(7):1339-47.

Benson, et al. Suppression of choroid plexus transthyretin levels by antisense oligonucleotide treatment. Amyloid. Jun. 2010;17(2):43-9. doi: 10.3109/13506129.2010.483121.

Bird, et al. Single-chain antigen-binding proteins. Science. Oct. 21, 1988;242(4877):423-6.

Blake, et al. Structure of prealbumin: secondary, tertiary and quaternary interactions determined by Fourier refinement at 1.8 A. J Mol Biol. May 25, 1978;121(3):339-56.

Blankenstein, et al. A retroviral expression vector containing murine immunoglobulin heavy chain promoter/enhancer. Nucleic Acids Res. Nov. 25, 1988;16(22):10939.

Boshart, et al. A very strong enhancer is located upstream of an immediate early gene of human cytomegalovirus. ll. Jun. 1985;41(2):521-30.

Bourgault, et al. Sulfated glycosaminoglycans accelerate transthyretin amyloidogenesis by quaternary structural conversion. Biochemistry. Feb. 15, 2011;50(6):1001-15. doi: 10.1021/bi101822y. Epub Jan. 24, 2011.

Bulawa, et al. Tafamidis, a potent and selective transthyretin kinetic stabilizer that inhibits the amyloid cascade. Proc Natl Acad Sci U S A. Jun. 12, 2012;109(24):9629-34. doi: 10.1073/pnas.1121005109. Epub May 29, 2012.

Cheng, et al. Amyloid β-sheet mimics that antagonize protein aggregation and reduce amyloid toxicity. Nat Chem. Nov. 2012;4(11):927-33. doi: 10.1038/nchem.1433. Epub Sep. 9, 2012.

Choi, et al. A substructure combination strategy to create potent and selective transthyretin kinetic stabilizers that prevent amyloidogenesis and cytotoxicity. J Am Chem Soc. Feb. 3, 2010;132(4):1359-70. doi: 10.1021/ja908562q.

Coelho, et al. A strikingly benign evolution of FAP in an individual found to be a compound heterozygote for two TTR mutations: TTR MET 30 and TTR MET 119. J. Rheumatol., 1993. 20: p. 179.

Coelho, et al. Compound heterozygotes of transthyretin Met 30 and transthyretin Met 119 are protected from the devastating effects of familial amyloid polyneuropathy. Neuromuscular Disorders. 1996;6(Suppl 1):S20. doi: 10.1016/0960-8966(96)88826-2.

Coelho, et al. Tafamidis for transthyretin familial amyloid polyneuropathy: a randomized, controlled trial. Neurology. Aug. 21, 2012;79(8):785-92. doi: 10.1212/WNL.0b013e3182661eb1. Epub Jul. 25, 2012.

Colon, et al. Partial denaturation of transthyretin is sufficient for amyloid fibril formation in vitro. Biochemistry. Sep. 15, 1992;31(36):8654-60.

Cone, et al. High-efficiency gene transfer into mammalian cells: generation of helper-free recombinant retrovirus with broad mammalian host range. Proc Natl Acad Sci U S A. Oct. 1984;81(20):6349-53.

De La Pena, et al. Transgenic rye plants obtained by injecting DNA into young floral tillers. Nature 325, 274-276 (Jan. 15, 1987); doi:10.1038/325274a0.

Foss, et al. The pathway by which the tetrameric protein transthyretin dissociates. Biochemistry. Nov. 29, 2005;44(47):15525-33.

Gillies, et al. A tissue-specific transcription enhancer element is located in the major intron of a rearranged immunoglobulin heavy chain gene. Cell. Jul. 1983;33(3):717-28.

Glenner. Amyloid deposits and amyloidosis: the beta-fibrilloses (second of two parts). N Engl J Med. Jun. 12, 1980;302(24):1333-43.

Goldsteins, et al. Exposure of cryptic epitopes on transthyretin only in amyloid and in amyloidogenic mutants. Proc Natl Acad Sci U S A. Mar. 16, 1999;96(6):3108-13.

Guild, et al. Development of retrovirus vectors useful for expressing genes in cultured murine embryonal cells and hematopoietic cells in vivo. J Virol. Oct. 1988;62(10):3795-801.

Gunning, et al. A human beta-actin expression vector system directs high-level accumulation of antisense transcripts. Proc Natl Acad Sci USA. 1987; 84:4831-4835.

Hammarstrom, et al. Sequence-dependent denaturation energetics: A major determinant in amyloid disease diversity. Proc Natl Acad Sci U S A. Dec. 10, 2002;99 Suppl 4:16427-32. Epub Sep. 25, 2002.

Hammarstrom, et al. Trans-suppression of misfolding in an amyloid disease. Science, 2001. 293(5539): p. 2459-62.

Hantzopoulos, et al. Improved gene expression upon transfer of the adenosine deaminase minigene outside the transcriptional unit of a retroviral vector. Proc Natl Acad Sci U S A. May 1989;86(10):3519-23.

(56) References Cited

OTHER PUBLICATIONS

Hess. Pollen-Based Techniques in Genetic Manipulation. Intern Rev. Cytol. 1987;107:367-395.
Hsiao, et al. N-acetylcysteine prevents beta-amyloid toxicity by a stimulatory effect on p35/cyclin-dependent kinase 5 activity in cultured cortical neurons. J Neurosci Res. Sep. 2008;86(12):2685-95. doi: 10.1002/jnr.21710.
Hurshman Babbes, et al. Quantification of the thermodynamically linked quaternary and tertiary structural stabilities of transthyretin and its disease-associated variants: the relationship between stability and amyloidosis. Biochemistry. Jul. 1, 2008;47(26):6969-84. doi: 10.1021/bi800636q. Epub Jun. 7, 2008.
Hurshman, et al. Transthyretin aggregation under partially denaturing conditions is a downhill polymerization. Biochemistry. Jun. 15, 2004;43(23):7365-81.
Huston, et al. Protein engineering of antibody binding sites: recovery of specific activity in an anti-digoxin single-chain Fv analogue produced in *Escherichia coli*. Proc Natl Acad Sci U S A. Aug. 1988;85(16):5879-83.
International search report and written opinion dated Nov. 6, 2014 for PCT Application No. US2014/015421.
Jacobson, et al. Genetic aspects of amyloidosis. Adv Hum Genet. 1991;20:69-123, 309-11.
Jacobson, et al. Transthyretin Pro55, a variant associated with early-onset, aggressive, diffuse amyloidosis with cardiac and neurologic involvement. Hum Genet. May 1992;89(3):353-6.
Jacobson, et al. Variant-sequence transthyretin (isoleucine 122) in late-onset cardiac amyloidosis in black Americans. Engl J Med. Feb. 13, 1997;336(7):466-73.
Johnson, et al. Bisaryloxime Ethers as Potent Inhibitors of Transthyretin Amyloid Fibril Formation. J. Med. Chem., 2005, 48 (5), pp. 1576-1587.
Johnson, et al. Native state kinetic stabilization as a strategy to ameliorate protein misfolding diseases: a focus on the transthyretin amyloidoses. Acc Chem Res. Dec. 2005;38(12):911-21.
Johnson, et al. The transthyretin amyloidoses: from delineating the molecular mechanism of aggregation linked to pathology to a regulatory-agency-approved drug. J Mol Biol. Aug. 10, 2012;421(2-3):185-203. doi: 10.1016/j.jmb.2011.12.060. Epub Jan. 5, 2012.
Jones, et al. Replacing the complementarity-determining regions in a human antibody with those from a mouse. Nature. 1986; 321: 522-5.
Kay, et al. Evidence for gene transfer and expression of factor IX in haemophilia B patients treated with an AAV vector. Nat Genet. Mar. 2000;24(3):257-61.
Kelly, et al. Transthyretin quaternary and tertiary structural changes facilitate misassembly into amyloid. Adv Protein Chem. 1997;50:161-81.
Klabunde, et al. Rational design of potent human transthyretin amyloid disease inhibitors. Nat Struct Biol. Apr. 2000;7(4):312-21.
Kohler, et al. Continuous cultures of fused cells secreting antibody of predefined specificity. Nature. Aug. 7, 1975;256(5517):495-7.
Luo, et al. A simple method for the transformation of rice via the pollen-tube pathway. Plant Mol. Biol. Reporter. 1988; 6(3):165-174.
Martone, et al. Transthyretin is synthesized in the mammalian eye. Biochem Biophys Res Commun. Mar. 15, 1988;151(2):905-12.
Mason, et al. Transcription cell type specificity is conferred by an immunoglobulin VH gene promoter that includes a functional consensus sequence. Cell. Jun. 1985;41(2):479-87.
McIvor, et al. Human purine nucleoside phosphorylase and adenosine deaminase: gene transfer into cultured cells and murine hematopoietic stem cells by using recombinant amphotropic retroviruses. Mol Cell Biol. Feb. 1987;7(2):838-46.
Miller, et al. Generation of helper-free amphotropic retroviruses that transduce a dominant-acting, methotrexate-resistant dihydrofolate reductase gene. Mol Cell Biol. Mar. 1985;5(3):431-7.
Miltenyi, et al. High gradient magnetic cell separation with MACS. Cytometry. 1990;11(2):231-8.
Miroy, et al. Inhibiting transthyretin amyloid fibril formation via protein stabilization. Proc Natl Acad Sci U S A. Dec. 24, 1996;93(26):15051-6.
Nakai, et al. Adeno-associated viral vector-mediated gene transfer of human blood coagulation factor IX into mouse liver. Blood. Jun. 15, 1998;91(12):4600-7.
Oza, et al. Synthesis, structure, and activity of diclofenac analogues as transthyretin amyloid fibril formation inhibitors. J Med Chem. Jan. 17, 2002;45(2):321-32.
Palha, et al. Antibody recognition of amyloidogenic transthyretin variants in serum of patients with familial amyloidotic polyneuropathy. J Mol Med (Berl). 2001;78(12):703-7.
Peng, et al.. Retroviral-mediated gene transfer and expression of human phenylalanine hydroxylase in primary mouse hepatocytes. Proc Natl Acad Sci U S A. Nov. 1988;85(21):8146-50.
Peterson, et al Inhibiting transthyretin conformational changes that lead to amyloid fibril formation. Proc Natl Acad Sci U S A. Oct. 27, 1998;95(22):12956-60.
Petrassi, et al. Structure-based design of N-phenyl phenoxazine transthyretin amyloid fibril inhibitors. J Am Chem Soc. 2000;122:2178-2192.
Pfeffer, et al. Expression of transthyretin and retinol binding protein mRNAs and secretion of transthyretin by cultured monkey retinal pigment epithelium. Mol Vis. Jan. 14, 2004;10:23-30.
Presta, L. Antibody engineering. Curr Opin Biotechnol. 1992; 3(4): 394-8.
Purkey, et al. Evaluating the binding selectivity of transthyretin amyloid fibril inhibitors in blood plasma. Proc Natl Acad Sci U S A. May 8, 2001;98(10):5566-71.
Raz, et al. Studies on the protein-protein and protein-ligand interactions involved in retinol transport in plasma. J Biol Chem. Apr. 25, 1970;245(8):1903-12.
Raz, et al. The interaction of thyroxine with human plasma prealbumin and with the prealbumin-retinol-binding protein complex. J Biol Chem. Jun. 25, 1969;244(12):3230-7.
Razavi, et al. Benzoxazoles as transthyretin amyloid fibril inhibitors: synthesis, evaluation, and mechanism of action. Angew Chem Int Ed Engl. Jun. 23, 2003;42(24):2758-61.
Razavi, et al. Design, synthesis, and evaluation of oxazole transthyretin amyloidogenesis inhibitors. Bioorg Med Chem Lett. Feb. 15, 2005;15(4):1075-8.
Redondo, et al. Search for intermediate structures in transthyretin fibrillogenesis: soluble tetrameric Tyr78Phe TTR expresses a specific epitope present only in amyloid fibrils. J Mol Biol. Dec. 1, 2000;304(3):461-70.
Reixach, et al. Tissue damage in the amyloidoses: Transthyretin monomers and nonnative oligomers are the major cytotoxic species in tissue culture. Proc Natl Acad Sci U S A. Mar. 2, 2004;101(9):2817-22. Epub Feb. 23, 2004.
Riechmann, et al. Reshaping human antibodies for therapy. Nature. 1988;332(6162): 323-327.
Sanford, et al. Optimizing the biolistic process for different biological applications. Methods Enzymol. 1993;217:483-509.
Saraiva. Transthyretin mutations in health and disease. Hum Mutat. 1995;5(3):191-6.
Sarver, et al. Bovine papilloma virus deoxyribonucleic acid: a novel eucaryotic cloning vector. Mol Cell Biol. Jun. 1981;1(6):486-96.
Sekijima, et al. The biological and chemical basis for tissue-selective amyloid disease. Cell. Apr. 8, 2005;121(1):73-85.
Tabin, et al. Adaptation of a retrovirus as a eucaryotic vector transmitting the herpes simplex virus thymidine kinase gene. Mol Cell Biol. Apr. 1982;2(4):426-36.
Ueda, et al. Clinicopathological features of senile systemic amyloidosis: an ante- and post-mortem study. Mod Pathol. Dec. 2011;24(12):1533-44. doi: 10.1038/modpathol.2011.117. Epub Aug. 5, 2011.
Van Assendelft, et al. The beta-globin dominant control region activates homologous and heterologous promoters in a tissue-specific manner. Cell. Mar. 24, 1989;56(6):969-77.
Van Jaarsveld, et al. The interaction of human plasma retinol-binding protein and prealbumin. J Biol Chem. Jul. 10, 1973;248(13):4698-705.

(56) References Cited

OTHER PUBLICATIONS

Westermark, et al., Fibril in senile systemic amyloidosis is derived from normal transthyretin. Proc Natl Acad Sci U S A. Apr. 1990;87(7):2843-5.
Wigler, et al. Transfer of purified herpes virus thymidine kinase gene to cultured mouse cells. Cell. May 1977;11(1):223-32.
Wiseman, et al. Kinetic stabilization of an oligomeric protein by a single ligand binding event. J Am Chem Soc. Apr. 20, 2005;127(15):5540-51.
Wojtczak, et al. Structures of human transthyretin complexed with thyroxine at 2.0 A resolution and 3',5'-dinitro-N-acetyl-L-thyronine at 2.2 A resolution. Acta Crystallogr D Biol Crystallogr. Jul. 1, 2005;52(Pt 4):758-65.
Zhou, et al. Introduction of exogenous DNA into cotton embryos. Methods Enzymol. 1983;101:433-81.
Costa, et al. Immunoassay for transthyretin variants associated with amyloid neuropathy. Scand J Immunol. Aug. 1993;38(2):177-82.
European search report and opinion dated May 30, 2016 for EP Application No. 14749029.

\* cited by examiner

TRANSTHYRETIN ANTIBODIES AND USES THEREOF

CROSS-REFERENCE

This application claims the benefit of U.S. Provisional Application No. 61/762,750, filed Feb. 8, 2013, and claims the benefit of U.S. Provisional Application No. 61/863,818, filed Aug. 8, 2013, which applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 11, 2017, is named 43982-701.831_SL.txt and is 23.1 Kilobytes in size. The sequence listing submitted electronically contains no new matter.

BACKGROUND OF THE INVENTION

Transthyretin (TTR) is a homotetrameric protein composed of 127-amino acid, 14 kDa monomeric subunits. TTR is also known as CTS, HsT2651, PALB, prealbumin, and TBPA. TTR is synthesized in the liver, choroid plexus and retinal pigment epithelium for secretion into blood, cerebrospinal fluid (CSF), and the eye, respectively. In the blood, TTR serves as a carrier for the retinol-binding protein-retinol (vitamin A) complex, whereas in CSF and the eye, it carries both thyroxine and holo retinol-binding protein. In its native state, TTR exists as a tetramer.

TTR is an amyloidogenic protein that can form fibrils and other aggregates. Rate-limiting TTR tetramer dissociation can generate dimers which subsequently can dissociate into monomers. These monomers can subsequently adopt misfolded conformations and aggregate into TTR oligomers and amyloid fibrils in a process known as amyloidogenesis. Mounting evidence indicates that the active aggregation of misfolded monomeric TTR or TTR amyloidogenesis is a root cause of TTR amyloid diseases.

The process of TTR amyloid fibril formation or amyloidogenesis is associated with a number of diseases, which present a significant burden on human health. For example, wild-type TTR amyloidogenesis is associated with senile systemic amyloidosis (SSA), a cardiomyopathy affecting up to 25% of the population above the age of 80. Another example of a TTR-related amyloid disease is the autosomal dominantly inherited disorder familial amyloid polyneuropathy (FAP). FAP is a relentless degenerative disease that strikes between the age 20-60 and causes progressive peripheral nerve degeneration, autonomic nervous system dysfunction, and in many individuals cardiomyopathy. Without a liver transplant, FAP is usually fatal within 10-12 years. Familial amyloid cardiomyopathy (FAC), another inherited TTR-aggregation-associated disease, can lead to congestive heart failure and death. There are now more than 100 TTR point mutations associated with the hereditary amyloid diseases. Many of these diseases are often misdiagnosed because their symptoms can be mistaken for other diseases. Misdiagnosis and the general lack of early diagnostic methods for the TTR-related amyloidoses currently present a significant roadblock to effective treatment, as irreversible degeneration has often occurred by the time treatment is initiated.

SUMMARY OF THE INVENTION

In one aspect, the invention provides an anti-transthyretin antibody that exhibits selective binding to non-native TTR under physiologically relevant conditions as compared to tetrameric TTR for said antibody binding.

In some embodiments, an antibody as disclosed herein binds to an epitope that is more accessible on non-native TTR as compared to tetrameric TTR, wherein epitope accessibility is evidenced by formation of an epitope/antibody complex in a binding assay.

In another aspect, the invention provides an anti-transthyretin antibody that exhibits selective binding to a non-native form of mutant transthyretin (TTR) obtained from an amyloid disease carrier under physiologically relevant conditions as compared to a tetrameric form of said mutant TTR generally comprising wild-type (WT) and mutant subunits.

In some embodiments, the amyloid disease is familial amyloid polyneuropathy, familial amyloid cardiomyopathy, carpel tunnel syndrome, leptomeningeal amyloidosis, familial oculoleptomeningeal amyloidosis, or senile systemic amyloidosis.

In some embodiments, an antibody as disclosed herein is a polyclonal antibody or monoclonal antibody.

In some embodiments of the non-native TTR binding antibodies described herein, an antibody as disclosed herein binds to wild-type monomeric and/or wild-type oligomeric TTR.

In some embodiments of the non-native TTR binding antibodies described herein, an antibody binds to mutant monomeric and/or mutant oligomeric TTR.

In some embodiments of the non-native TTR binding antibodies described herein, an antibody as disclosed herein antibody does not recognize the generic forms of cross-beta-sheet amyloid fibrils.

In some embodiments, mutant transthyretin comprises a mutation selected from the group consisting of a Cys10Arg mutation, a Leu12Pro mutation, an Asp18Glu mutation, an Asp18Gly mutation, an Asp18Asn mutation, a Val20Ile mutation, a Ser23Asn mutation, a Pro24Ser mutation, an Ala25Thr mutation, an Ala25Ser mutation, a Val28Met mutation, a Val30Met mutation, a Val30Ala mutation, a Val30Leu mutation, a Val30Gly mutation, a Val32Ala mutation, a Phe33Ile mutation, a Phe33Leu mutation, a Phe33Val mutation, a Phe33Cys mutation, an Arg34Thr mutation, an Arg34Gly mutation, a Lys35Asn mutation, a Lys35Thr mutation, an Ala36Pro mutation, an Asp38Ala mutation, an Asp38Val mutation, a Trp41Leu mutation, a Glu42Gly mutation, a Glu42Asp mutation, a Phe44Ser mutation, an Ala45Asp mutation, an Ala45Ser mutation, an Ala45Thr mutation, a Gly47Arg mutation, a Gly47Ala mutation, a Gly47Val mutation, a Gly47Glu mutation, a Thr49Ala mutation, a Thr49Ile mutation, a Thr49Pro mutation, a Ser50Arg mutation, a Ser50Ile mutation, a Glu51Gly mutation, a Ser52Pro mutation, a Gly53Glu mutation, a Gly53Ala mutation, a Glu54Gly mutation, a Glu54Lys mutation, a Glu54Leu mutation, a Leu55Arg mutation, a Leu55Pro mutation, a Leu55Gln mutation, a Leu55Glu mutation, a His56Arg mutation, a Gly57Arg mutation, a Leu58His mutation, a Leu58Arg mutation, a Thr59Lys mutation, a Thr60Ala mutation, a Glu61Lys mutation, a Glu61Gly mutation, a Phe64Leu mutation, a Phe64Ser mutation, a Gly67Glu mutation, a Ile68Leu mutation, a Tyr69His mutation, a Tyr69Ile mutation, a Lys70Asn mutation, a Val71Ala mutation, a Ile73Val mutation, a Ser77Phe mutation, a Ser77Tyr mutation, a Tyr78Phe mutation, an Ala81Val mutation, an Ala81Thr mutation, a Ile84Ser mutation, a Ile84Asn mutation, a Ile84Thr mutation, a His88Arg mutation, a Glu89Gln mutation, a Glu89Lys mutation, a His90Asp mutation, an Ala91Ser mutation, a Gln92Lys mutation, a Val94Ala mutation, an Ala97Gly mutation, an Ala97Ser mutation, an Arg103Ser mutation, a Ile107Val mutation, a Ile107Met mutation, a Ile107Phe mutation, an Ala109Ser mutation, a Leu111Met mutation, a Ser112Ile mutation, a Tyr114Cys mutation, a Tyr114His mutation, a Tyr116Ser mutation, an Ala120Ser mutation, a Val122Ile mutation, a DelVal122 mutation, a Val122Ala mutation, and an Asn124Ser mutation.

In some embodiments of any of the antibodies described herein, said selective binding to said non-native TTR as compared to tetrameric TTR is evidenced by an increased amount of immunocomplexes formed between an invention antibody and non-native TTR as compared to the amount of immunocomplexes formed between the antibody and tetrameric TTR.

In some embodiments, a non-native TTR comprises more than four transthyretin subunits.

In some embodiments, a non-native TTR is an oligomeric TTR that exhibits a molecular weight greater than 56 kD.

In some embodiments, a non-native TTR is monomeric TTR.

In some embodiments, an anti-transthyretin antibody as disclosed herein binds to an epitope residing between positions 30-66 in SEQ ID. NO. 1

In some embodiments, an antibody disclosed herein exhibits weaker binding to an epitope when TTR is in a native tetrameric conformation as compared to when TTR is in a non-native conformation.

In some embodiments, weaker binding can be ascertained by indirect ELISA.

In some embodiments, an epitope comprises at least 3, 4, 5, 6, 7, 8, 9, 10, 12, 15 amino acids in length.

In some embodiments, an epitope is contained in the amino acid sequence ADDTWEPFASGKT (SEQ ID NO: 14) or TSESGELHGLTTE (SEQ ID NO: 15).

In some embodiments, an anti-transthyretin antibody binds to an epitope residing between positions 109-121 in SEQ ID. NO. 1.

In some embodiments, an antibody exhibits weaker binding to the epitope when TTR is in a native tetrameric conformation as compared to when TTR is in a non-native conformation.

In some embodiments, an epitope is contained in the amino acid sequence ALLSPYSYSTTAV (SEQ ID NO: 16).

In some embodiments, a complex comprising an antibody disclosed herein and the epitope exhibits a dissociation constant that is less than 10 nM.

In another aspect, the invention provides a host cell that produces any of the antibodies of the present invention.

In another aspect, the invention provides an isolated polynucleotide comprising a nucleic acid sequence encoding an antibody of the present invention.

In another aspect, the invention provides a vector comprising a polynucleotide encoding an antibody of the present invention.

In some embodiments, a host cell is a mammalian cell.

In some embodiments, a host cell is a myeloma cell.

In some embodiments, a host cell is a hybridoma.

In another aspect, the invention provides for a method for treating an amyloid disease in a subject in need thereof, comprising: administering an anti-aggregate agent to the subject upon detection of non-native TTR in the subject.

In some embodiments, the method comprises administering an anti-aggregate agent to the subject upon detection of non-native TTR in a biological sample obtained from the subject.

In some embodiments, non-native TTR is detected by an antibody of the present invention.

In another aspect, the invention provides for a method of administering an anti-aggregate agent to a subject in need thereof, comprising administering an anti-aggregate agent to the subject at multiple time points; measuring a level of non-native TTR in the subject upon at least a first and second time point of administration; and adjusting dosage of the anti-aggregate agent and/or selecting a different anti-aggregate agent for administration based on the detected level non-native TTR.

In some embodiments, a first time point occurs before administering a first dosage of the anti-aggregate agent.

In some embodiments, a second time point occurs after administering a first dosage of the anti-aggregate agent.

In some embodiments, non-native TTR is measured by an assay utilizing an antibody of the present invention.

In some embodiments, the method comprises increasing dosage of the anti-aggregate agent if the detected level is increased by at least 20% at a second time point as compared to a first time point.

In another aspect, the invention provides for a method of detecting the increased likelihood of developing an amyloid disease symptom in a subject that has not developed an amyloid disease symptom, comprising: measuring a level of non-native TTR in the subject using an antibody of the present invention; and designating the subject as having an increased likelihood of developing the amyloid disease symptom if the level is increased as compared to a level of non-native TTR measured in a control subject.

In a related aspect, the invention provides for a method of designating a subject suffering a symptom of an amyloid-associated disease, comprising: measuring a level of non-native TTR in the subject using an antibody of the present invention; and designating the subject as having the amyloid disease based on the measured level of non-native TTR.

In some embodiments, the method further comprises alerting the subject or a caregiver thereof of the designation.

In practicing any of the methods of the invention, in some embodiments, an amyloid (or amyloid-associated disease) disease is selected from the group consisting of amyloidosis, cardiomyopathy, polyneuropathy, diabetes, ophthalmic diseases and diseases (incl. age-related macular degeneration), idiopathic cardiomyopathy, Amyotrophic lateral sclerosis (ALS), Immunoglobulin light chain amyloidosis (AL), carpel tunnel syndrome, familial amyloid polyneuropathy, familial amyloid cardiomyopathy, senile systemic amyloidosis, leptomeningeal amyloidosis, and familial oculoleptomeningeal amyloidosis.

In another aspect, the invention provides for a method of assessing the efficacy of an anti-aggregate therapy applied to a subject, comprising measuring a change in the level of non-native TTR in the subject during therapy, wherein the measuring is performed using an antibody of the present invention, and wherein a decrease in the level of non-native FUR during therapy indicates that the therapy is efficacious.

In some embodiments, the method further comprises alerting the subject or caregiver thereof that the therapy is efficacious if the change is a decrease in the level of non-native TTR.

In some embodiments, the method further comprises alerting the subject or caregiver thereof that the therapy is not efficacious if the change is not a decrease in the level of non-native TTR.

In practicing any of the methods of the invention, detection or measuring a level of non-native TTR comprises detecting or measuring in a biological sample obtained from the subject.

In some embodiments, the biological sample is a liquid sample.

In some embodiments, the subject is a human.

In some embodiments, the anti-aggregate agent or therapy comprises a TTR kinetic stabilizer, wherein the TTR kinetic stabilizer stabilizes the TTR tetrameric form against dissociation.

In some embodiments, the kinetic stabilizer is a benzoxazole.

In some embodiments, the benzoxazole is tafamidis.

In some embodiments, the kinetic stabilizer is diflunisal.

In some embodiments, the anti-aggregate agent or therapy comprises an anti-TTR agent intended at reducing total TTR protein level.

In another aspect, the invention provides a kit for the detection of non-native TTR in a sample, comprising an antibody of the present invention; and instructions for conducting a binding assay utilizing the antibody.

In some embodiments, the kit further comprises a detectable label capable of forming a complex with the antibody.

In another aspect, the invention provides a computer system for detecting the increased likelihood of developing an amyloid disease symptom in a subject that has not developed an amyloid disease symptom, comprising: a memory unit configured to store data related to concentration of non-native TTR in a biological sample from the subject; and a computer readable medium that is configured to designate the subject as having an increased likelihood of developing the amyloid disease symptom if the level is increased as compared to a level of non-native TTR measured in a control subject.

In another aspect, the invention provides a computer system for detecting the increased likelihood of developing an amyloid disease symptom in a subject that has not developed the amyloid disease symptom, comprising: a memory unit configured to store data related to concentration of non-native TTR in a biological sample from the subject; and a computer readable medium that is configured to designate the subject as having an increased likelihood of developing the amyloid disease symptom if the level is changed over 20% as compared to a level of non-native TTR measured in the subject at an earlier time point.

In another aspect, the invention provides a computer system for designating a subject suffering a symptom associated with a plurality of diseases as having an amyloid disease, comprising: a memory unit configured to store data related to a level of non-native TTR in a biological sample from the subject; and a computer readable medium that is configured to designate the subject as having an amyloid disease if the level is increased as compared to a level of non-native TTR measured in a control subject.

In another aspect, the invention provides a computer system for assessing the efficacy of an anti-aggregate therapy applied to a subject, comprising: a memory unit configured to store data related to a change in the level of non-native TTR in the subject during therapy; and a computer readable medium that is configured to designate the therapy as efficacious if the change is a decrease in the level of non-native TTR during the therapy.

In another aspect, the invention provides a computer system for adjusting treatment for an amyloid disease in a subject, comprising: a memory unit configured to store data related to concentration of non-native TTR in a biological sample from the subject; and a user interface that is configured to provide an alert to a caregiver to administer an anti-aggregate agent to the subject if the concentration of non-native TTR is increased as compared to a measured concentration of non-native TTR in a control subject.

In some embodiments, an anti-aggregate agent is a TTR kinetic stabilizer, wherein the TTR kinetic stabilizer stabilizes a TTR tetrameric form against dissociation.

In some embodiments, a kinetic stabilizer is a benzoxazole which includes but is not limited to tafamidis.

In some embodiments, a kinetic stabilizer can be diflunisal.

In some embodiments, an anti-aggregate agent comprises an anti-TTR agent that reduces total TTR protein level.

In some embodiments, a non-native TTR is monomeric and/or oligomeric TTR.

In another aspect, the invention provides an immunocomplex comprising a non-native TTR and an antibody of the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

GENERAL TECHNIQUES

Figure 1:
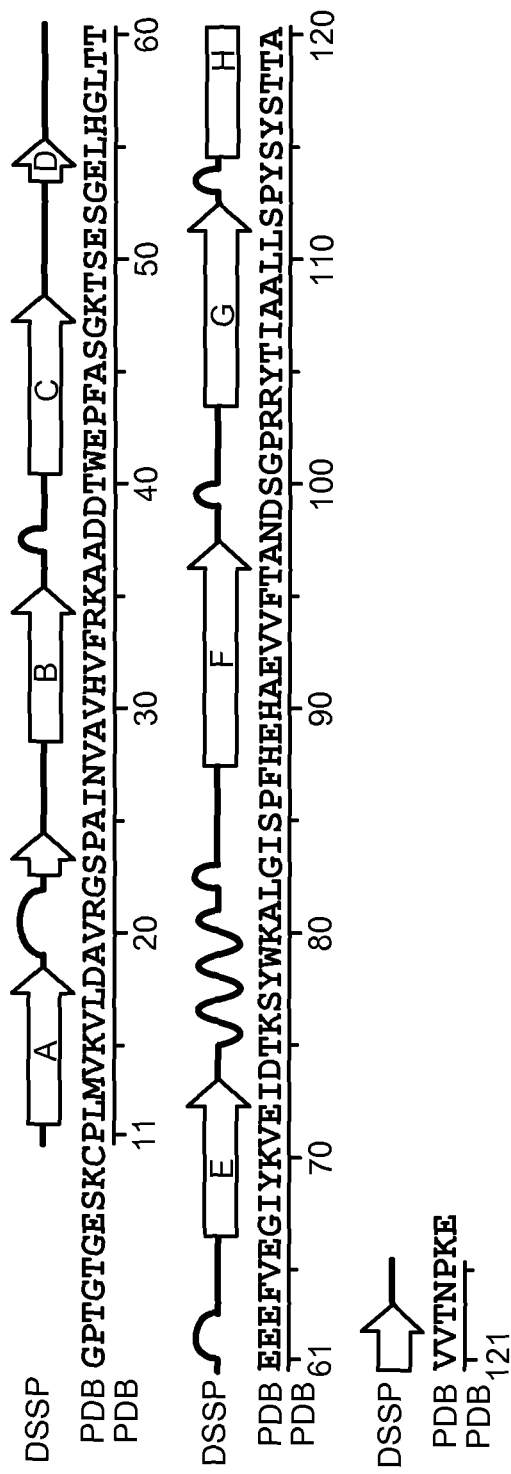
FIG. 1 illustrates the secondary structure of a single monomeric subunit from tetrameric wild-type TTR based on crystal structure (SEQ ID NO: 1). All beta-strands are labeled.

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Matthews, PLANT VIROLOGY, 3.sup.rd edition (1991); Sambrook, Fritsch and Maniatis, MOLECULAR CLONING: A LABORATORY MANUAL, 2.sup.nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular forms "a", "an" and "the" include plural references unless the context clearly dictates otherwise. For example, the term "a cell" includes a plurality of cells, including mixtures thereof.

Definitions

The terms "polypeptide", "peptide", and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "amino acid", as used herein, encompasses naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., γ-carboxyglutamate, hydroxyproline, and O-phosphoserine. Amino acid analogs refers to compounds that have the same basic chemical structure as a naturally occurring amino acid, i.e., an a carbon that is bound to a hydrogen, a carboxyl group, an amino group, and an R group. Exemplary amino acid analogs include but are not limited to homoserine, norleucine, methionine sulfoxide, and methionine methyl sulfonium. Such analogs can have modified R groups (e.g., norleucine) or modified peptide backbones, as long as they retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission.

The term "antibody" or "antibodies" or as used herein refers to immunoglobulin (Ig) molecules and antigen-binding portions of immunoglobulin molecules, i.e., molecules that contain an antigen binding site which specifically binds to an antigen. Structurally, a simple naturally occurring antibody (e.g., IgG) comprises four polypeptide chains: two heavy (H) chains and two light (L) chains that are interconnected by disulfide bonds. The natural immunoglobulins represent a large family of molecules that include several types of molecules, such as IgD, IgG, IgA, IgM and IgE.

"Antibodies" can also refer to hybrid or altered antibodies. The antigen-binding function of an antibody can be performed by fragments of a naturally-occurring antibody, therefore, the term "antibodies" also encompasses fragments of antibodies, altered antibodies, or hybrid antibodies, including but not limited to Fab fragment(s), and Fv fragments. These fragments are also known as "antigen-binding fragments". Examples of binding fragments encompassed within the term "antigen-binding fragments" include but are not limited to (i) Fab fragments consisting of the VL, VH, CL and CH1 domains; (ii) Fd fragments consisting of the VH and CH1 domains; (iii) Fv fragments consisting of the VL and VH domains of a single arm of an antibody, (iv) dAb fragments which consists of a VH domain as described by (Ward et al., (1989) Nature 341:544-546), (v) isolated complementarity determining regions (CDRs); and (vi) F(ab')2 fragments, which are bivalent fragments comprising two Fab fragments linked by a disulfide bridge at the hinge region. Furthermore, although the two domains of the Fv fragment are generally coded for by separate genes, a synthetic linker can be made that enables them to be made as a single protein chain (known as single chain Fv (scFv); Bird et al. (1988) Science 242:423-426; and Huston et al. (1988) PNAS 85:5879-5883) by recombinant methods. Such single chain antibodies are also encompassed within the term "antigen-binding fragments". Preferably, the antibody fragments are those which are capable of crosslinking their target antigen, such as, e.g., bivalent fragments such as F(ab')2 fragments. Alternatively, antibody fragments which do not themselves crosslink their target antigen (e.g., a Fab fragments) can be used in conjunction with secondary antibodies which serves to crosslink the antibody fragment, thereby crosslinking the target antigen.

Antibodies can be fragmented using conventional techniques described herein or known in the art and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab fragments can be prepared, for example, by proteolytic digestion of substantially intact immunoglobulin molecules using methods that are well known in the art, e.g., by papain digestion. However, Fab fragments may also be prepared by expressing in a suitable host cell the desired portions of immunoglobulin heavy chain and immunoglobulin light chain using methods disclosed herein or any other methods known in the art.

An Fv fragment of an immunoglobulin molecule is a multimeric protein consisting of the immunologically active portions of an immunoglobulin heavy chain variable region and an immunoglobulin light chain variable region covalently coupled together and capable of specifically binding to an antigen. Fv fragments are typically prepared by expressing in suitable host cell the desired portions of immunoglobulin heavy chain variable region and immunoglobulin light chain variable region using methods described herein and/or other methods known to artisans in the field.

The term "antibodies" can also include bispecific and chimeric molecules having a desired binding portion. Also encompassed within the term "antibodies" are vertebrate antibodies, hybrid antibodies or chimeric antibodies.

The term "antibodies" also encompasses humanized antibodies. Humanized" forms of non-human (e.g., murine) antibodies include chimeric antibodies containing minimal sequence derived from a non-human Ig. In some embodiments, the humanized antibodies are human Igs (recipient antibody) in which one or more of the CDRs of the recipient are replaced by CDRs from a non-human donor antibody, such as mouse, rat, rabbit or non-human primate antibody having the desired specificity, affinity and binding function. In some embodiments, one or more FR amino acid residues of the human Ig are replaced by corresponding non-human amino acid residues. In some cases, humanized antibodies contain modified residues which are not found in the recipient antibody or in the donor antibody. These modified residues can serve to refine antibody performance, if needed. A humanized antibody can comprise substantially all of at least one and, in some cases two, variable domains, in which all or substantially all of the hypervariable regions correspond to those of a non-human donor Ig and all, or substantially all, of the FRs are those of a human Ig sequence. The humanized antibody optionally can also include at least a portion of an Ig constant region (Fc), typically that of a human immunoglobulin. For details, see Jones et al., Nature 321: 522-525 (1986); Reichmann et al., Nature 332: 323-329 (1988); and Presta, Curr. Op. Struct. Biol. 2: 593-596 (1992).

"Humanized antibodies" also encompasses antibodies in which part, or all of the CDRs of the heavy and light chain are derived from a non-human monoclonal antibody, substantially all the remaining portions of the variable regions are derived from human variable region (both heavy and light chain), and the constant regions are derived from a human constant region. In one embodiment, the CDR1, CDR2 and CDR3 regions of the heavy and light chains are derived from a non-human antibody. In yet another embodiment, at least one CDR (for example, a CDR3) of the heavy and light chains is derived from a non-human antibody. A person of skill in the art will understand that any combination of CDR1, CDR2, and CDR3 derived from a non-human antibody are within the scope of the invention.

The term "antibodies" also encompasses catalytic antibodies, e.g., antibodies that harbor antigen-specific catalytic activity. Antigen-specific catalytic activity may include, for example, antigen-specific proteolytic cleavage. Catalytic antibodies, and methods of producing the same, are described in, e.g., U.S. Pat. Nos. 5,658,753 and 7,205,136.

"Antigen" as used herein means a substance that is recognized and bound specifically by an antibody. Antigens can include peptides, proteins, glycoproteins, polysaccharides and lipids; portions thereof and combinations thereof.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

A "cell line" or "cell culture" denotes bacterial, plant, insect or higher eukaryotic cells grown or maintained in vitro. The descendants of a cell may not be completely identical (either morphologically, genotypically, or phenotypically) to the parent cell.

A "defined medium" refers to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a) all essential amino acids, and usually the basic set of twenty amino acids plus cysteine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolar range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

"Homology" or "identity" or "similarity" refers to sequence similarity between two peptides or between two polynucleotides. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences.

As used herein, the term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring the polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart.

Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

An "isolated" antibody can also be "substantially pure" when free of most or all of the materials with which it typically associates with in nature. Thus, an isolated antibody sample that is substantially pure does not include polypeptides or polynucleotides present among millions of other sequences, such as antibodies of an antibody library or nucleic acids in a genomic or cDNA library, for example. Of course, a "substantially pure" molecule can be combined with one or more other molecules. Thus, the term "substantially pure" is not meant to exclude combination compositions.

A sample of isolated antibody can be considered "substantially pure" if the antibody accounts for 60%, 70%, 80%, 90%, or more than 90% of the sample by weight. Purity can be determined by any appropriate method, including but not limited to, UV spectroscopy, chromatography (e.g., HPLC, gas phase), gel electrophoresis (e.g., silver or coomassie staining) and sequence analysis (nucleic acid and peptide).

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide which is known to comprise additional residues in one or both directions.

The terms "polynucleotides", "nucleic acid", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as gene product. If the polynucleotide is derived from genomic DNA, expression may include splicing of the mRNA in a eukaryotic cell.

A "subject" as used herein refers to a biological entity containing expressed genetic materials. The biological entity is preferably plant, animal, or microorganisms including bacteria, viruses, fungi, and protozoa. Tissues, cells and their progeny of a biological entity obtained in vivo or cultured in vitro are also encompassed.

A "vector" is a nucleic acid molecule, preferably self-replicating, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions.

An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

"Heterologous" means derived from a genotypically distinct entity from the rest of the entity to which it is being compared. For example, a promoter removed from its native coding sequence and operatively linked to a coding sequence other than the native sequence is a heterologous promoter. The term "heterologous" as applied to a polynucleotide, a polypeptide, means that the polynucleotide or polypeptide is derived from a genotypically distinct entity from that of the rest of the entity to which it is being compared. For instance, a heterologous polynucleotide or antigen may be derived from a different species origin, different cell type, and the same type of cell of distinct individuals.

"Recombinant" as applied to a polynucleotide means that the polynucleotide is the product of various combinations of cloning, restriction and/or ligation steps, and other procedures that result in a construct that is distinct from a polynucleotide found in nature.

The terms "gene" or "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

DETAILED DESCRIPTION OF THE INVENTION

Aspects of the invention relate to antibodies that selectively recognize and bind to non-native TTR. Such antibodies have a wide range of diagnostic and therapeutic applications. Accordingly, in one aspect, the invention provides anti-transthyretin antibodies that exhibit selective binding to non-native forms of TTR under physiologically relevant conditions, as compared to tetrameric TTR for said antibody binding. In a related aspect, the invention provides anti-transthyretin antibodies that exhibit selective binding to non-native forms of mutant TTR present in an amyloid disease carrier under physiologically relevant conditions as compared to a tetrameric form of said mutant TTR.

The term "bind" or "binding" means that the binding partners referred to have affinity for each other. The term "specific" or "selective" and grammatical variations thereof, when used in reference to binding, means that the binding between the binding partners is such that it can be distinguished from non-specific or non-selective binding to other molecules. For example, an antibody exhibits "selective binding" to an antigen if it binds with greater affinity or avidity than it binds to other reference antigens including polypeptides or other substances. In some embodiments, the antibodies exhibit a 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, or more than 100-fold greater binding to non-native TTR as compared to native TTR of the same composition. In particular embodiments, the antibodies exhibit a 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, or more than 100-fold greater binding to non-native TTR as compared to native TTR of the same composition. Selective binding can be ascertained using a binding assay such as, e.g., ELISA, immunoprecipitation, coprecipitation, western blotting, surface plasmon resonance, multiplex immunoassay, two-hybrid assays and the like. In some embodiments, the binding assay is an ELISA assay. In one embodiment, the ELISA assay is an indirect (e.g., sandwich) assay. Such binding assays can produce a stronger detectable signal in a sample wherein an antibody of the present invention is reacted with non-native TTR, as compared to a sample wherein the antibody is reacted with native TTR. Generally, a detectable signal can be described as a signal produced by a detectable label. The detectable label can be any molecule that can be conjugated to another molecule so as to enable detection of the conjugated molecule. Non-limiting examples of detectable labels include chelators, photoactive agents, radionuclides (alpha, beta and gamma emitters), fluorescent agents, luminescent agents, nanoparticles, paramagnetic ions, or enzymes that produce a detectable signal in the presence of certain reagents (e.g., horseradish peroxidase, alkaline phosphatase, glucose oxidase).

The terms "tetrameric TTR" and "native TTR" are used interchangeably herein to refer to a protein formed by the association of four TTR monomers. Structurally, the TTR tetramer features two thyroxine-binding sites that are formed by the weaker dimer-dimer interface of TTR. Each TTR monomer comprises 127 amino acids. Within the native tetramer, the monomer is made up of two face-to-face β-sheets, containing β-strands CBEF and DAGH, respectively. The amino acid sequence of the TTR monomer with the β-strands labeled is depicted in FIG. 1.

"Non-native TTR forms", as used herein, refers to structural TTR conformations that are associated with formation of TTR aggregates including amyloid fibrils. The rate-limiting step of TTR amyloid formation is dissociation of tetrameric TTR into monomeric TTR. It is believed that upon dissociation of tetrameric TTR into monomeric TTR, monomeric TTR exhibits instability, adopting partially unfolded and misfolded conformations that promote aggregation into oligomers. The oligomers subsequently associate into protofibrils, which further associate into insoluble TTR amyloid fibrils and insoluble TTR amyloid deposits. Accordingly, non-native TTR forms include but are not limited to partially unfolded or misfolded TTR tetramer, partially unfolded or misfolded monomeric TTR, oligomeric TTR, TTR protofibrils, TTR fibrils, and TTR amyloid deposits. In some embodiments, non-native TTR may contain truncated TTR caused by proteolysis. In some embodiments, antibodies of the invention exhibit selective binding to monomeric and/or oligomeric TTR. Monomeric TTR is described herein. In some embodiments, the antibodies further exhibit selective binding to TTR protofibrils, TTR fibrils, TTR amyloid deposits, or any combination thereof.

"Oligomeric TTR", as used herein, refers to non-native TTR proteins formed by the association of more than 4 TTR monomers. In some embodiments, TTR oligomers are formed of 5-10 subunits, 7-20 subunits, 10-50 subunits, 30-100 subunits, or more than 100 subunits. In some embodiments, TTR oligomers comprise more than 100 subunits. In some embodiments, TTR oligomers comprise less than 8 subunits. In some embodiments, the TTR oligomers are formed of 8, 12, 16, 24, 32, 40, 48, 56, 64, 72, 80, 88, 96, or more subunits. In some embodiments, the TTR oligomers are pentamers, hexamers, heptamers, or octomers. In some embodiments, oligomeric TTR exhibits a molecular weight that is greater than 56 kD. In some embodiments, the subunits in the oligomeric TTR compose of mutant TTR. In some embodiments, the subunits in the said oligomers compose of wild-type TTR. In other embodiments, the subunits in the said oligomers compose of a mixture of mutant and wild-type TTR monomers or truncated monomers.

Amyloid deposits can be characterized as insoluble, fibrous protein aggregates. In some embodiments, the amyloid deposits exhibit beta sheet structure. In some embodiments, the amyloid deposits substantially comprise protein fibrils. Amyloid fibrils can be characterized as thread-like protein aggregates that are insoluble and resistant to protease activity. They comprise β-strands that run perpendicular to the fiber axis and form a cross β-sheet of indefinite length. "Protofibrils" can be characterized as elongated protein aggregates that are generally soluble.

"Physiologically relevant conditions", as used herein, generally refer to environmental conditions that do not promote protein denaturation. Physiologically relevant conditions can include in vivo conditions (e.g., physiological conditions), in vitro conditions wherein TTR is retained in a cellular milieu (e.g., live cell imaging), or in vitro conditions wherein TTR is isolated from a cellular milieu but remains in an environment that does not promote significant protein denaturation. Protein denaturation generally refers to a process in which proteins lose their quaternary, tertiary, and/or secondary structure which is present in a native state, generally, by application of a stressor. Therefore, physiologically relevant conditions can be generally characterized as lacking external stressors that induce protein denaturation.

For example, the binding assays may be conducted under physiologically relevant buffer conditions. Generally, a physiological buffer contains a physiological concentration of salt and is adjusted to a neutral pH ranging from about 6.5 to about 7.8, and preferably from about 7.0 to about 7.5. A variety of physiological buffers is listed in Sambrook et al. (1989) supra and hence is not detailed herein.

Another exemplary stressor that can induce protein denaturation is non-physiological pH. Generally, non-physiological pH refers to either acidic or basic (i.e. —non-neutral) pH. Acidic pH can be a pH less than about 7, less than about 6.5, less than about 6, less than about 5, or less than about 4. Exemplary acidic denaturants include but are not limited to acetic acid, citrate acid, trichloroacetic acid, sulfosalicylic acid. Basic pH can be greater than about 7.5, greater than about 8.0, or greater than about 8.5). Physiologically relevant pH conditions can be about pH 6-8, about pH 6.5-7.8, about pH 7.0-7.5.

Non-physiological salt concentrations represent another stressor that can promote protein denaturation. Some salts, such as ammonium sulfate, tend to stabilize protein structures and increase the melting temperature. Others, such as calcium chloride, destabilize proteins and lower the melting temperature and are referred to as chaotropic. Exemplary chaotropic salts include but are not limited to heavy metal salts, lithium trifluoromethanesulfonate (LiOTD, lithium hexafluorophosphate (LiPF(6)), and lithium bis(trifluoromethanesulfonyl)imide (LiNTf(2), Guanidinium chloride, magnesium chloride, lithium acetate. Exemplary physiological salt concentrations include salt concentrations of physiological buffers, described herein.

High, non-physiological temperatures can also induce protein denaturation. Many proteins denature at about 41 degrees C. or higher. Physiologically relevant temperatures can include temperatures below 41 deg C., below 40 deg C., below 39 deg C., below 38 deg C. Furthermore, temperatures below freezing can also affect native protein structure. Physiologically relevant temperatures can include temperatures above 0 deg C., above 1 deg C., above 2 deg C., above 3 deg C., or about 4 deg C. or higher. In one embodiment, a physiologically relevant temperature ranges from about 4 deg C. to about 40 deg C.

Presence of chaotropic agent including but not limited to urea, guanidium hydrochloride, sodium dodecyl sulfate, and alcohols (e.g. ethanol) can also disrupt native non-covalent protein intramolecular interactions such as hydrophobic interactions, electrostatic interactions, and hydrogen bonding. Thus, the presence of chaotropic agent is another example of a non-physiologically relevant condition.

Proteins can denature at interfaces. During the course of an immunoassay, several interfaces are formed that affect the structure and function of the biological components. An exemplary interface is the interface between a solid surface and a liquid solution. In some embodiments, proteins present at an interface (e.g., a solid/liquid interface) are in a non-physiologically relevant condition. For example, direct attachment of proteins to a solid surface (e.g., during a direct ELISA assay), can alter the conformation of proteins and induce denaturation, hence, may be considered as a non-physiologically relevant condition. Accordingly, an in vitro binding assay can be considered to be conducted under physiologically relevant conditions if more than 50% of proteins in a test sample are present in a liquid solution and not localized to a solid/liquid interface (e.g., not directly attached to a solid surface).

In some embodiments, the antibodies bind to wild-type or mutant TTR. The term "mutant TTR" refers to any TTR protein species that is encoded by a TTR gene that harbors a mutation in the TTR gene. A mutant TTR protein may harbor a missense mutation in less than all of the subunits (some being wild type), in which a single nucleotide change in the TTR gene causes an amino acid substitution in the TTR amino acid sequence. A mutant TTR protein may harbor a frameshift mutation, e.g., a mutation that disrupts the reading frame of the gene resulting in a substantially different amino acid sequence as compared to wild-type TTR. Alternatively, a mutant TTR protein may harbor a nonsense mutation, resulting in a premature stop codon, which causes significant truncation of the protein product. In particular embodiments, the mutant TTR protein harbors a missense mutation. In particular, there are over 100 missense mutant forms of TTR known to be associated with amyloid disease. In some embodiments, the mutant TTR is a mutant TTR associated with an amyloid disease (amyloidogenic mutant TTR). In some embodiments, sporadic or familial amyloidogenic mutation is present on either a single allele (e.g., a heterozygous mutation) or both alleles (e.g., a homozygous mutation) of the TTR gene. In some embodiments, the amyloidogenic mutant TTR comprises a Cys10Arg, Leu12Pro, Asp18Glu, Asp18Gly, Asp18Asn, Val20Ile, Ser23Asn, Pro24Ser, Ala25Thr, Ala25Ser, Val28Met, Val30Met, Val30Ala, Val30Leu, Val30Gly, Val32Ala, Phe33Ile, Phe33Leu, Phe33Val, Phe33Cys, Arg34Thr, Arg34Gly, Lys35Asn, Lys35Thr, Ala36Pro, Asp38Ala, Asp38Val, Trp41Leu, Glu42Gly, Glu42Asp, Phe44Ser, Ala45Asp, Ala45Ser, Ala45Thr, Gly47Arg, Gly47Ala, Gly47Val, Gly47Glu, Thr49Ala, Thr49Ile, Thr49Pro, Ser50Arg, Ser50Ile, Glu51Gly, Ser52Pro, Gly53Glu, Gly53Ala, Glu54Gly, Glu54Lys, Glu54Leu, Leu55Arg, Leu55Pro, Leu55Gln, Leu55Glu, His56Arg, Gly57Arg, Leu58His, Leu58Arg, Thr59Lys, Thr60Ala, Glu61Lys, Glu61Gly, Phe64Leu, Phe64Ser, Gly67Glu, Ile68Leu, Tyr69His, Tyr69Ile, Lys70Asn, Val71Ala, Ile73Val, Ser77Phe, Ser77Tyr, Tyr78Phe, Ala81Val, Ala81Thr, Ile84Ser, Ile84Asn, Ile84Thr, His88Arg, Glu89Gln, Glu89Lys, His90Asp, Ala91Ser, Gln92Lys, Val94Ala, Ala97Gly, Ala97Ser, Ile107Val, Ile107Met, Ile107Phe, Ala109Ser, Leu111Met, Ser112Ile, Tyr114Cys, Tyr114His, Tyr116Ser, Ala120Ser, Val122Ile, DelVal122, Val122Ala, or Asn124Ser mutation. In other embodiments, the mutant TTR is not associated with an amyloid disease (non-amyloidogenic mutant TTR). In some embodiments, the non-amyloidogenic mutant TTR comprises a Gly6Ser, Met13Ile, Asp74His, His90Asn, Gly101Ser, Pro102Arg, Arg104Cys, Arg104His, Ala108Ala, Ala109Thr, Ala109Val, Thr119Met, or Pro125Ser mutation. In other embodiments, a mutant TTR may harbor more than one mutation. In particular embodiments, a mutant TTR may harbor two mutations, either on the same allele or on different alleles. A mutation may be any combination of the single mutations described herein. In some embodiments, the mutant TTR is a Gly6Ser/Val30Met, Gly6Ser/Phe33Ile, Gly6Ser/Ala45Asp, Gly6Ser/Ser77Tyr, Gly6Ser/Tyr114Cys, Gly6Ser/Thr119Met, Gly6Ser/Val122/Ala, His90Asn/Val30Met, His90Asn Glu42Gly, His90Asn/Thr119Met, Arg104His/Val30Met, or Thr119Met/Val30Met mutation.

"Amyloid disease carrier", as used herein, generally refers to a symptomatic subject carrying an amyloid disease or an asymptomatic subject carrying a gene mutation or known risk factor for developing an amyloid disease. The terms "amyloid disease" or "amyloid associated disease" are used interchangeably herein to refer to any disease that is associated with deposition of amyloid in a subject. Amyloid deposits can accumulate in one or more organs or body systems and disrupt the function of said one or more organs or body systems. Exemplary amyloid diseases include, e.g., Alzheimer's disease, Type 2 diabetes, Parkinson's disease, transmissible spongiform encephalopathy, Huntington's disease, medullary carcinoma of the thyroid, cardiac arrhythmia, isolated atrial amyloidosis, atherosclerosis, rheumatoid arthritis, aortic medial amyloid, prolactinomas, familial amyloid polyneuropathy, hereditary non-neuropathic systemic amyloidosis, dialysis-related amyloidosis, Finnish amyloidosis, lattice corneal dystrophy, cerebral amyloid angiopathy, systemic AL amyloidosis, multiple myeloma, familial amyloid cardiomyopathy, senile systemic amyloidosis, amyloidosis, cardiomyopathy, polyneuropathy, diabetes, ophthalmic diseases and disorders such as, e.g., age-related macular degeneration, idiopathic cardiomyopathy, amyotrophic lateral sclerosis (ALS), Immunoglobulin light chain amyloidosis (AL), and carpel tunnel syndrome, among others. In preferred embodiments, the amyloid disease is a disease associated with amyloidogenic TTR, e.g., familial amyloid polyneuropathy, familial amyloid cardiomyopathy, senile systemic amyloidosis, leptomeningeal amyloidosis, familial oculoleptomeningeal amyloidosis, idiopathic polyneuropathy, and post mitotic tissue degeneration.

Epitopes

In some embodiments, the antibody binds to an epitope that is more accessible on non-native TTR as compared to tetrameric TTR. The term "epitope" refers to an antigenic determinant to which an antibody binds. A polypeptide epitope can be as few as three, four, five, six, seven, eight, ten, eleven, twelve, thirteen, fourteen, fifteen, amino acids or as many as sixteen to fifty or even more amino acids. The term "conformational epitope" refers to an epitope comprised of a two or three dimensional juxtaposition of amino acids; the amino acids may be contiguous or non-contiguous, on the same polypeptide or on one or more different polypeptides.

In some embodiments, the antibody binds to an epitope that is more accessible on monomeric and/or oligomeric TTR as compared to tetrameric TTR. Epitope accessibility can be ascertained by the formation of a complex between the epitope and the antibody. In some embodiments, formation of the complex is detected by a binding assay, e.g., an immunoassay.

In some embodiments, the epitope is a conformational epitope. In some embodiments, the conformation epitope comprises non-consecutive amino acids from any wild-type or mutant TTR sequence that form a 3-D structure that exhibits binding affinity for the antibody.

In some embodiments, the epitope comprises a plurality of non-consecutive amino acids between positions 30-66 of a wild-type or mutant TTR sequence. In other embodiments, the epitope comprises a plurality of non-consecutive amino acids between positions 70-127, 80-127, 90-127, 100-127, 110-127, or 115-127 of any wild-type or mutant TTR sequence. In other embodiments, the epitope comprises a plurality of consecutive amino acids from any wild-type or mutant TTR protein that exhibits a different conformation when said wild-type or mutant TTR is monomeric or oligomeric as compared to when said wild-type or mutant TTR is in tetrameric form.

In some embodiments, the epitope comprises a portion of the TTR amino acid sequence that is predicted to be buried in the TTR tetramer but exposed in the dissociated monomer, as predicted by the crystal structure. Epitope prediction can be facilitated by molecular visualization software such as, e.g., PyMOL, BioBlender, Visual_Molecular_Dynamics, Jmol, Geneious Pro, RasMol, UCSF Chimera, STING, VisProt3DS, Polyview-3D. In some embodiments the epitope is a portion of the amino acid sequence that is predicted to be exposed in both the TTR tetramer and monomer but adopts a different conformation when TTR is in monomeric as opposed to tetrameric form (e.g., a conformational epitope).

In some embodiments, the epitope comprises a plurality of consecutive amino acids between positions about 30 to about 66 of any wild-type or mutant TTR sequence. In other embodiments, the epitope comprises a plurality of consecutive amino acids between positions about 70-127, 80-127, 90-127, 109-121, 100-127, 110-127, or 115-127 of any wild-type or mutant TTR sequence. In other embodiments, the epitope comprises a plurality of consecutive amino acids between positions about 115-127 of any wild-type or mutant TTR sequence. In some embodiments, the epitope is 3, 4, 5, 6, 7, 8, 9, 10, 12, 14, 16, 18, 20, or more than 20 amino acids in length. In some embodiments, the epitope is 3-7, 4-10, 7-15, 10-20, or more than 20 amino acids in length.

In some embodiments, the epitope is contained in or comprises the amino acid sequence ADDTWEPFASGKT (SEQ ID NO: 14) or TSESGELHGLTTE (SEQ ID NO: 15). In some embodiments, the epitope is contained in or comprises the amino acid sequence ALLSPYSYSTTAV (SEQ ID NO: 16).

In some embodiments the antibody exhibits weaker binding to the epitope when TTR is in a tetrameric conformation. In some embodiments, said weaker binding is ascertained by an indirect, e.g., sandwich ELISA assay. An exemplary sandwich ELISA assay is described herein.

Antibodies of the present invention can be in the form of monoclonal, polyclonal, chimeric, humanized, catalytic, and recombinant antibodies.

In some embodiments, the antibody is a monoclonal antibody. The term "monoclonal antibody" as used herein refers to an antibody composition comprising a substantially homogeneous antibody population. It is not intended to be limited as regards to the source of the antibody or the manner in which it is made. Monoclonal antibodies generally bind to a single antigenic site or epitope. In contrast to conventional (polyclonal) antibody preparations which typically include different antibodies directed against different determinants (epitopes), each monoclonal antibody is directed against a single epitope on the antigen. Monoclonal antibodies can include whole antibodies or fragments thereof.

In other embodiments, the antibody is a polyclonal antibody or a fragment thereof. The term "polyclonal antibody" as used herein refers to an antibody composition that comprises a non-homogenous antibody population raised against an antigen. Antibodies in the non-homogenous antibody population can recognize different epitopes on said antigen. In some cases, antibodies in the non-homogenous antibody population recognize the same epitope on said antigen. In some embodiments, the antigen is a polypeptide that comprises a portion of the TTR amino acid sequence. In some embodiments, the antigen is more accessible on monomeric and/or oligomeric TTR as compared to tetrameric TTR. Antigen accessibility can be ascertained by the formation of a complex between the antigen and the antibody, as described herein. In some embodiments, the antigen comprises a plurality of consecutive amino acids between positions 30-66 of any wild-type or mutant TTR sequence. In other embodiments, the antigen comprises a plurality of consecutive amino acids between positions 60-127 of any wild-type or mutant TTR sequence. In other embodiments, the antigen comprises a plurality of consecutive amino acids between positions 70-127, 80-127, 109-121, 90-127, 100-127, 110-127, or 115-127 of any wild-type or mutant TTR sequence. In some embodiments, the antigen is 3, 4, 5, 6, 7, 8, 9, 10, 12, 14, 16, 18, 20, or more than 20 amino acids in length. In some embodiments, the antigen is 3-7, 4-10, 7-15, 10-20, 15-30, 20-40, 30-60, or more than 60 amino acids in length.

In some embodiments, the antigen comprises the amino acid sequence ADDTWEPFASGKT (SEQ ID NO: 14) or TSESGELHGLTTE (SEQ ID NO: 15).

The antibodies of the present invention also encompass antibodies conjugated to a functional moiety. The functional moiety can be a detectable label capable of generating a detectable signal. Exemplary detectable labels include, but are not limited to, fluorescent compounds, chemiluminescent compounds, bioluminescent compounds, enzymes, radioisotopes, colloidal metals, paramagnetic labels. These antibodies can be used, for example, in methods and systems for the detection, imaging, and/or quantitation of non-native TTR in a subject or in a sample obtained from a subject. Other functional moieties include, e.g., signal peptides, agents that enhance immunologic reactivity, capture reagents which facilitate attachment to a solid support, vaccine carriers, bioresponse modifiers, and drugs. Signal peptides can be short amino acid sequences. Such sequences can target proteins to a cellular compartment, e.g., to endoplasmic reticulum, to the Golgi complex, to the nucleus, to acellular membrane, or can target a protein for secretion. Exemplary agents that enhance immunologic reactivity include, e.g., bacterial superantigens. Exemplary capture reagents include, e.g., biotin, avidin, streptavidin, neutravidin, captavidin, polyhistidine tags. Vaccine carriers can be, e.g., keyhole limpet hemocyanin or tetanus toxoid. Bioresponse modifiers can be, e.g., cytokines such as, e.g., tumor necrosis factor, interleukin-2, interleukin 4, granulocyte macrophage colony stimulating factor, and gamma interferon. Drug moieties can be, e.g., an anti-aggregate agent. Exemplary anti-aggregate agents are described herein.

The chemically functional moieties can be attached to the antibody by any means known in the art. For example, a fusion gene encoding the antibody operably linked to a functional moiety can be created. Alternatively, the antibody can be chemically bonded to the moiety by any of a variety of well-established chemical procedures. For example, when the moiety is a protein, the linkage may be by way of a cross linker, e.g., SPDP, carbodiimide glutaraldehyde, or the like. The moieties may be covalently linked, or conjugated, through a secondary reagent, such as a second antibody, protein A, or a biotin-avidin complex. Paramagnetic moieties can be conjugated to the antibody by means that are well-known in the art. See, e.g., Miltenyi et al. (1990) Cytometry 11:231-238.

Table 1 summarizes the properties of exemplary antibodies of the present invention.

TABLE 1 list of antibodies and their properties

| Antibody ID | Host | Type | Epitope | Affinity ($K_d$, nM) |
|---|---|---|---|---|
| MFD101 | Mouse | IgG1 | ADDTWEPFASGKT (SEQ ID NO: 14) | |
| MFD102 | Mouse | IgG1 | ADDTWEPFASGKT (SEQ ID NO: 14) | 0.2 |
| MFD103 | Mouse | IgG1 | ADDTWEPFASGKT (SEQ ID NO: 14) | |
| MFD104 | Mouse | IgG1 | N.D. | |
| MFD105 | Mouse | IgG1 | ADDTWEPFASGKT (SEQ ID NO: 14) | |
| MFD106 | Mouse | IgG1 | N.D. | |
| MFD107 | Mouse | IgG1 | TSESGELHGLTTE (SEQ ID NO: 15) | |

TABLE 1-continued list of antibodies and their properties

| Antibody ID | Host | Type | Epitope | Affinity ($K_d$, nM) |
|---|---|---|---|---|
| MFD108 | Mouse | IgG1 | TSESGELHGLTTE (SEQ ID NO: 15) | 0.25 |
| MFD109 | Mouse | IgG1 | TSESGELHGLTTE (SEQ ID NO: 15) | |
| MFD110 | Mouse | IgG1 | N.D. | |
| MFD111 | Mouse | IgG1 | TSESGELHGLTTE (SEQ ID NO: 15) | |
| MFD112 | Mouse | IgG1 | N.D. | |
| MFD113 | Rabbit | pAb | Multiple (see text for details) | |
| MFD114 | Rabbit | pAb | ALLSPYSYSTTAV (SEQ ID NO: 16) | 0.53 |

Polynucleotides and Vectors of the Present Invention

The invention provides various polynucleotides that encode antibodies of the invention or fragments thereof. In some embodiments, the polynucleotide comprise a coding sequence that encodes a heavy chain polypeptide of an invention antibody. In some embodiments, the polynucleotide comprise a coding sequence that encodes a light chain polypeptide of an invention antibody. In some embodiments, the polynucleotide comprises both a coding sequence encoding a light chain polypeptide of an invention antibody and a coding sequence encoding a heavy chain polypeptide of an invention antibody.

In some embodiments, the polynucleotide comprises a coding sequence that encodes a heavy chain region of the invention antibody. In one embodiment, the coding sequence has at least 80% sequence homology to SEQ. ID. NO. 2. In another embodiment, the coding sequence encodes an amino acid sequence having 80% sequence homology to SEQ. ID. NO. 3. In one embodiment, the coding sequence encodes a heavy chain region of an antibody produced by a hybridoma clone corresponding to ATCC deposit # PTA-120817.

In some embodiments, the coding sequence has at least 80% sequence homology to SEQ. ID NO. 4. In some embodiments, the polynucleotide comprises a DNA sequence that encodes an amino acid sequence having least 80% homology to SEQ. ID NO. 5. In one embodiment, the coding sequence encodes a heavy chain region of an antibody produced by a hybridoma clone corresponding to ATCC deposit # PTA-120816.

In some embodiments, the coding sequence has at least 80% sequence homology to SEQ. ID NO. 6. In some embodiments, the polynucleotide comprises a DNA sequence that encodes an amino acid sequence having least 80% homology to SEQ. ID NO. 7.

In some embodiments, the polynucleotide comprises a coding sequence that encodes a light chain region of the invention antibody. In one embodiment, the coding sequence has at least 80% sequence homology to SEQ. ID. NO. 8. In another embodiment, the coding sequence encodes an amino acid sequence having 80% sequence homology to SEQ. ID. NO. 9. In one embodiment, the coding sequence encodes a light chain region of an antibody produced by a hybridoma clone corresponding to ATCC deposit # PTA-120817.

In some embodiments, the coding sequence has at least 80% sequence homology to SEQ. ID NO. 10. In some embodiments, the polynucleotide comprises a DNA sequence that encodes an amino acid sequence having least 80% homology to SEQ. ID NO. 11. In one embodiment, the coding sequence encodes a light chain region of an antibody produced by a hybridoma clone corresponding to ATCC deposit # PTA-120816.

In some embodiments, the coding sequence has at least 80% sequence homology to SEQ. ID NO. 12. In some embodiments, the polynucleotide comprises a DNA sequence that encodes an amino acid sequence having least 80% homology to SEQ. ID NO. 13.

The antibody nucleotide sequences may also be modified, for example, by substituting the coding sequence for human heavy and light chain constant regions in place of the homologous non-human sequences. In that manner, chimeric antibodies are prepared that retain the binding specificity of the original antibody.

It is also understood that the polynucleotides embodied in the invention include those coding for functional equivalents and fragments thereof of the exemplified polypeptides. Functionally equivalent polypeptides include those that enhance, decrease or not significantly affect properties of the polypeptides encoded thereby. Functional equivalents may be polypeptides having conservative amino acid substitutions, analogs including fusions, and mutants.

Due to the degeneracy of the genetic code, there can be considerable variation in nucleotides of the L and H sequences, as well as the heterodimerization sequences suitable for construction of the polynucleotide and vectors of the present invention. Sequence variants may have modified DNA or amino acid sequences, one or more substitutions, deletions, or additions, the net effect of which is to retain the desired antigen-binding activity. For instance, various substitutions can be made in the coding region that either do not alter the amino acids encoded or result in conservative changes. These substitutions are encompassed by the present invention. Conservative amino acid substitutions include substitutions within the following groups: glycine, alanine; valine, isoleucine, leucine; aspartic acid, glutamic acid; asparagine, glutamine; serine, threonine; lysine, arginine; and phenylalanine, tyrosine. While conservative substitutions do effectively change one or more amino acid residues contained in the polypeptide to be produced, the substitutions are not expected to interfere with the antigen-binding activity of the resulting antibodies to be produced. Nucleotide substitutions that do not alter the amino acid residues encoded are useful for optimizing gene expression in different systems. Suitable substitutions are known to those of skill in the art and are made, for instance, to reflect preferred codon usage in the expression systems.

Where desired, the recombinant polynucleotides may comprise heterologous sequences that facilitate detection of the expression and purification of the gene product. Examples of such sequences are known in the art and include those encoding reporter proteins such as beta-galactosidase, beta-lactamase, chloramphenicol acetyltransferase (CAT), luciferase, green fluorescent protein (GFP) and their derivatives. Other heterologous sequences that facilitate purification may code for epitopes such as Myc, HA (derived from influenza virus hemagglutinin), His-6 (SEQ ID NO: 17), FLAG, or the Fc portion of immunoglobulin, glutathione S-transferase (GST), and maltose-binding protein (MBP).

The polynucleotides can be conjugated to a variety of chemically functional moieties described above.

The polynucleotides of the invention can comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention.

The polynucleotides embodied in this invention can be obtained using chemical synthesis, recombinant cloning methods, PCR, or any combination thereof. Methods of chemical polynucleotide synthesis are well known in the art and need not be described in detail herein. One of skill in the art can use the sequence data provided herein to obtain a desired polynucleotide by employing a DNA synthesizer or ordering from a commercial service.

Polynucleotides comprising a desired sequence can be inserted into a suitable vector which in turn can be introduced into a suitable host cell for replication and amplification. Accordingly, the invention encompasses a variety of vectors comprising one or more of the polynucleotides of the present invention. Also provided is a selectable library of expression vectors comprising at least one vector encoding an invention antibody.

Vectors can be any plasmid, virus, viral vector, or other vehicle known in the art that can be manipulated by insertion or incorporation of a nucleic acid. For example, "cloning vectors" can be employed for the purposes of genetic manipulation. For another example, "expression vectors" can be employed to transcribe or translate the inserted polynucleotide. Generally, expression vectors are useful for introducing nucleic acids, including a nucleic acid that encodes an antibody operably linked with an expression control element, and expressing the antibody in vitro (e.g., in solution or a solid phase), in cells, or in a subject in vivo.

Viral vectors can be based on retroviral, adeno-associated virus (AAV), lentiviral, adenoviral, retrovirus, or rotaviral genomes, simian virus 40 (SV40) or bovine papilloma virus (Cone et al., Proc. Natl. Acad. Sci. USA 81:6349 (1984); Eukaryotic Viral Vectors, Cold Spring Harbor Laboratory, Gluzman ed., 1982; Sarver et al., Mol. Cell. Biol. 1:486 (1981). Additional viral vectors useful for expression include Norwalk virus, coronaviruses, paramyxo and rhabdoviruses, togavirus (e.g., sindbis virus and semliki forest virus), parvovirus, and vesicular stomatitis virus (VSV).

Expression vectors can be designed for in vivo and ex vivo expression. One such mammalian expression vector is AAV (U.S. Pat. No. 5,604,090). AAV vectors have previously been shown to provide expression of Factor IX in humans and in mice at levels sufficient for therapeutic benefit (Kay et al., Nat. Genet. 24:257 (2000); Nakai et al., Blood 91:4600 (1998)). Adenoviral vectors (U.S. Pat. Nos. 5,700,470, 5,731,172 and 5,928,944),) retroviral (e.g., lentivirus vectors are useful for infecting dividing as well as non-dividing cells and foamy viruses) vectors (U.S. Pat. Nos. 5,624,820, 5,693,508, 5,665,577, 6,013,516 and 5,674, 703 and WIPO publications WO92/05266 and WO92/14829), herpes simplex virus vectors (U.S. Pat. No. 5,501, 979, and papilloma virus vectors (e.g., human and bovine papilloma virus) have all been employed in gene therapy (U.S. Pat. No. 5,719,054).

Vectors also include cytomegalovirus (CMV) based vectors (U.S. Pat. No. 5,561,063). Vectors that efficiently deliver genes to cells of the intestinal tract have been developed (see, e.g., U.S. Pat. Nos. 5,821,235, 5,786,340 and 6,110,456).

A vector generally contains an origin of replication for propagation in a cell. Control elements, including expression control elements as set forth herein, present within a vector, can be included to facilitate transcription and translation.

Suitable transcription or translational control sequences include but are not limited to replication origin, promoter, enhancer, repressor binding regions, transcription initiation sites, ribosome binding sites, translation initiation sites, and termination sites for transcription and translation.

As used herein, a "promoter" is a DNA region capable of binding RNA polymerase and initiating transcription of a coding region located downstream (in the 3' direction) from the promoter. The promoter can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase. Eukaryotic promoters can contain "TATA" boxes and "CAT" boxes.

The choice of promoters will largely depend on the host cells in which the vector is introduced. For animal cells, a variety of robust promoters, both viral and non-viral promoters, are known in the art. Non-limiting representative viral promoters include CMV, the early and late promoters of SV40 virus, promoters of various types of adenoviruses (e.g. adenovirus 2) and adeno-associated viruses. It is also possible, and often desirable, to utilize promoters normally associated with a desired light or heavy chain gene, provided that such control sequences are compatible with the host cell system.

Suitable promoter sequences for other eukaryotic cells include the promoters for 3-phosphoglycerate kinase, or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In certain preferred embodiments, the vectors of the present invention use strong enhancer and promoter expression cassettes. Examples of such expression cassettes include the human cytomegalovirus immediately early (HCMV-IE) promoter (Boshart et al, Cell 41: 521, (1985)), the beta-actin promoter (Gunning et al. (1987) Proc. Natl. Acad. Sci. (USA) 84: 5831), the histone H4 promoter (Guild et al. (1988), J Viral. 62: 3795), the mouse metallothionein promoter (McIvor et al. (1987), Mol, Cell. Biol. 7: 838), the rat growth hormone promoter (Millet et al. (1985), Mol. Cell Biol. 5: 431), the human adenosine deaminase promoter (Hantzapoulos et al. (1989) Proc. Natl. Acad. Sci. USA 86: 3519), the HSV tk promoter 25 (Tabin et al. (1982) Mol. Cell. Biol. 2: 426), the .alpha-1 antitrypsin enhancer (Peng et al. (1988) Proc. Natl. Acad. Sci. USA 85: 8146), and the immunoglobulin enhancer/promoter (Blankenstein et al. (1988) Nucleic Acid Res. 16: 10939), the SV40 early or late promoters, the Adenovirus 2 major late promoter, or other viral promoters derived from polyoma virus, bovine papilloma virus, or other retroviruses or adenoviruses. The promoter and enhancer elements of immunoglobulin (Ig) genes confer marked specificity to B lymphocytes (Banerji et al. (1983) Cell 33: 729; Gillies et al. (1983) Cell 33: 717; Mason et al. (1985) Cell 41: 479), while the elements controlling transcription of the B-globin gene function only in erythroid cells (van Assendelft et al. (1989) Cell 56:969).

Cell-specific or tissue-specific promoters may also be used. A vast diversity of tissue specific promoters have been described and employed by artisans in the field. Exemplary promoters operative in selective animal cells include hepatocyte-specific promoters and cardiac muscle specific promoters. Depending on the choice of the recipient cell types, those skilled in the art will know of other suitable cell-specific or tissue-specific promoters applicable for the construction of the expression vectors of the present invention.

Using well-known restriction and ligation techniques, appropriate transcriptional control sequences can be excised from various DNA sources and integrated in operative relationship with the intact selectable fusion genes to be expressed in accordance with the present invention.

In constructing the subject vectors, the termination sequences associated with the exogenous sequences are also inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional read-through. Preferred terminator sequences (or termination sites) of the present invention have a gene that is followed by a transcription termination sequence, either its own termination sequence or a heterologous termination sequence. Examples of such termination sequences include stop codons coupled to various polyadenylation sequences that are known in the art, widely available, and exemplified below. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

Vectors can also include a selection marker. A "selection marker" is a gene that allows for the selection of cells containing the gene. "Positive selection" refers to a process whereby only cells that contain the selection marker will survive upon exposure to the positive selection. Drug resistance is one example of a positive selection marker; cells containing the marker will survive in culture medium containing the selection drug, and cells lacking the marker will die. Selection markers include, for example, drug resistance genes (e.g., neo, which confers resistance to G418; hygr, which confers resistance to hygromycin; and puro, which confers resistance to puromycin). Other positive selection marker genes include genes that allow the visual identification or screening of cells containing the marker. These genes include genes for fluorescent proteins (GFP and GFP-like chromophores, luciferase), the lacZ gene, the alkaline phosphatase gene, and surface markers such as CD8, among others. "Negative selection" refers to a process whereby cells containing a negative selection marker are killed upon exposure to an appropriate negative selection agent. For example, cells which contain the herpes simplex virus-thymidine kinase (HSV-tk) gene (Wigler et al., Cell 11:223 (1977)) are sensitive to the drug gancyclovir (GANC). Similarly, the gpt gene renders cells sensitive to 6-thioxanthine.

The vectors embodied in this invention can be obtained using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or that in the public or proprietary databases to obtain a desired vector by any synthetic means available in the art.

Vectors can be produced using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or that in the public or proprietary databases to obtain a desired vector by any synthetic means available in the art.

Host Cell

In another aspect, the invention provides a host cell that produces an antibody of the invention. In some embodiments, the host cell is a stably or transiently transformed cell or progeny thereof into which a nucleic acid encoding an invention antibody or fragment thereof has been introduced by means of recombinant DNA technology in vitro, ex vivo or in vivo. In some embodiments, the transformed cell is propagated and the introduced nucleic acid transcribed, and/or encoded protein expressed. Transformed cells include, by way of non-limiting example, prokaryotic and eukaryotic cells such as bacteria, fungi, plant, insect, and animal (e.g., mammalian, including human) cells.

The term "transformed", as used herein, means a genetic change in a cell following incorporation of nucleic acid (e.g., a transgene) exogenous to the cell. Thus, a "transformed cell" is a cell into which, or a progeny of which a nucleic acid molecule has been introduced by means of recombinant DNA techniques. Cell transformation to produce host cells may be carried out as described herein or using any technique known in the art.

Introduction of antibodies and nucleic acid encoding invention antibodies into target cells can be carried out by methods known in the art such as osmotic shock (e.g., calcium phosphate), microinjection, electroporation, cell fusion, etc. Introduction of nucleic acid and can also be accomplished using other techniques. By way of example only, a nucleic acid can be entrapped in microcapsules prepared by coacervation techniques or by interfacial polymerization, e.g., by the use of hydroxymethylcellulose or gelatin-microcapsules, or poly (methylmethacrolate) microcapsules. Introduction of antibodies or nucleic acid encoding the same can also be delivered using a colloid drug delivery system. Colloidal delivery systems include, e.g., macromolecule complexes, nano-capsules, microspheres, beads, and lipid-based systems such as oil-in-water emulsions, micelles, piperazine based amphilic cationic lipids (described in U.S. Pat. No. 5,861,397), cationic lipid systems (described in U.S. Pat. No. 5,459,127), and liposomes, e.g., phosphatidylcholine, phosphatidylserine, lipofectin and DOTAP (see, e.g., U.S. Pat. Nos. 4,844,904, 5,000,959, 4,863,740, 4,975,282). Other methods suitable for transformation of host cells are described herein.

For most animal cells, any of the above-mentioned methods is suitable for vector delivery. Preferred animal cells are vertebrate cells, preferably mammalian cells, capable of expressing exogenously introduced gene products in large quantity, e.g. at the milligram level. Non-limiting examples of preferred cells are NIH3T3 cells, COS, HeLa, and CHO cells.

The animal cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, animal cells can be grown in a defined medium that lacks serum but is supplemented with hormones, growth factors or any other factors necessary for the survival and/or growth of a particular cell type. Whereas a defined medium supporting cell survival maintains the viability, morphology, capacity to metabolize and potentially, capacity of the cell to differentiate, a defined medium promoting cell growth provides all chemicals necessary for cell proliferation or multiplication. The general parameters governing mammalian cell survival and growth in vitro are well established in the art. Physicochemical parameters which may be controlled in different cell culture systems are, e.g., pH, $pO_2$, temperature, and osmolarity. The nutritional requirements of cells are usually provided in standard media formulations developed to provide an optimal environment. Nutrients can be divided into several categories: amino acids and their derivatives, carbohydrates, sugars, fatty acids, complex lipids, nucleic acid derivatives and vitamins. Apart from nutrients for maintaining cell metabolism, most cells also require one or more hormones from at least one of the following groups: steroids, prostaglandins, growth factors, pituitary hormones, and peptide hormones to proliferate in serum-free media (Sato, G. H., et al. in "Growth of Cells in Hormonally Defined Media", Cold Spring Harbor Press, N.Y., 1982). In addition to hormones, cells may require transport proteins such as transferrin (plasma iron transport protein), ceruloplasmin (a copper transport protein), and high-density lipoprotein (a lipid carrier) for survival and growth in vitro. The set of optimal hormones or transport proteins will vary for each cell type. Most of these hormones or transport proteins have been added exogenously or, in a rare case, a mutant cell line has been found which does not require a particular factor. Those skilled in the art will know of other factors required for maintaining a cell culture without undue experimentation.

For plant cells, a variety of vector delivery techniques is available in the art. The host cells may be in the form of whole plants, isolated cells or protoplasts. Illustrative procedures for introducing vectors into plant cells include *Agrobacterium*-mediated plant transformation, protoplast transformation, gene transfer into pollen, injection into reproductive organs and injection into immature embryos. As is evident to one skilled in the art, each of these methods has distinct advantages and disadvantages. Thus, one particular method of introducing vectors into a particular plant species may not necessarily be the most effective for another plant species.

*Agrobacterium tumefaciens*-mediated transfer is a widely applicable system for introducing vectors into plant cells because the vector can be introduced into whole plant tissues, bypassing the need for regeneration of an intact plant from a protoplast. The use of *Agrobacterium*-mediated expression vectors to introduce vector into plant cells is well known in the art. This technique makes use of a common feature of *Agrobacterium* which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a recombinant plant viral nucleic acid between the T-DNA border sequences results in transfer of the recombinant plant viral nucleic acid to the plant cells, where the recombinant plant viral nucleic acid is replicated, and then spreads systemically through the plant.

Because not all plants are natural hosts for *Agrobacterium*, alternative methods such as transformation of protoplasts may be employed to introduce the subject vectors into plant host cells. For certain monocots, transformation of the plant protoplasts can be achieved using methods based on calcium phosphate precipitation, polyethylene glycol treatment, electroporation, and combinations of these treatments.

In addition to protoplast transformation, particle bombardment is an alternative and convenient technique for delivering the invention vectors into a plant host cell. Specifically, the plant cells may be bombarded with microparticles coated with a plurality of the subject vectors. Bombardment with DNA-coated microprojectiles has been successfully used to produce stable transformants in both plants and animals (see, for example, Sanford et al. (1993) Methods in Enzymology, 217:483-509). Microparticles suitable for introducing vectors into a plant cell are typically made of metal, preferably tungsten or gold. These microparticles are available for example, from Bio-Rad (e.g., Bio-Rad's PDS-1000/He). Those skilled in the art will know that the particle bombardment protocol can be optimized for any plant by varying parameters such as He pressure, quantity of coated particles, distance between the macrocarrier and the stopping screen and flying distance from the stopping screen to the target.

Vectors can also be introduced into plants by direct DNA transfer into pollen as described by Thou et al., Methods in Enzymology, 101:433 (1983); D. Hess, Intern Rev. Cytol., 107:367 (1987); Luo et al., Plant Mol. Biol. Reporter, 6:165 (1988). Alternatively, the vectors can be injected into reproductive organs of a plant as described by Pena et al., Nature, 325:274 (1987).

Other techniques for introducing nucleic acids into a plant cell include: (a) Hand Inoculations. Hand inoculations are performed using a neutral pH, low molarity phosphate buffer, with the addition of celite or carborundum (usually about 1%). One to four drops of the preparation is put onto the upper surface of a leaf and gently rubbed. (b) Mechanized Inoculations of Plant Beds. Plant bed inoculations are performed by spraying (gas-propelled) the vector solution into a tractor-driven mower while cutting the leaves. Alternatively, the plant bed is mowed and the vector solution sprayed immediately onto the cut leaves. (c) High Pressure Spray of Single Leaves. Single plant inoculations can also be performed by spraying the leaves with a narrow, directed spray (50 psi, 6-12 inches from the leaf) containing approximately 1% carborundum in the buffered vector solution. (d) Vacuum Infiltration. Inoculations may be accomplished by subjecting a host organism to a substantially vacuum pressure environment in order to facilitate infection.

Other suitable host cells for cloning and expressing the subject vectors are prokaryotes and eukaryotic microbes such as fungi or yeast cells. Suitable prokaryotes for this purpose include bacteria including Gram-negative and Gram-positive organisms. Representative members of this class of microorganisms are Enterobacteriaceae (e.g. *E. coli*), *Enterobacter, Erwinia, Klebsiella, Proteus, Salmonella* (e.g. *Salmonella typhimurium*), *Serratia* (e.g., *Sefratia marcescans*), *Shigella, Neisseria* (e.g. *Neisseria meningitidis*) as well as *Bacilli* (e.g. *Bacilli subtilis* and *Bacilli licheniformis*). Preferably, the host cell secretes minimal amounts of proteolytic fragments of the expressed Abus. Commonly employed fungi (including yeast) host cells are *S. cerevisiae, Kluyveromyces lactis* (*K. lactis*), species of *Candida* including *C. albicans* and *C. glabrata, C. maltosa, C. utilis, C. stellatoidea, C. parapsilosis, C. tropicalus, Neurospora crassas, Aspergillus nidulans, Schizosaccharomyces pombe* (*S. pombe*), *Pichia pastoris*, and *Yarowia lipolytica*.

The cells may be present in culture, a tissue or organ ex vivo, or in a subject in vivo. A progeny cell does not necessarily need to be identical to the parental cell, since there may be mutations that occur during replication.

In some embodiments, the host cell is a hybridoma cell, e.g., a hybrid cell produced by the fusion of a B-lymphocyte producing an antibody of the invention with a myeloma cell. Such B-lymphocytes producing an invention antibody can be generated by, e.g., immunizing a test animal with an antigen as described herein and harvesting B-lymphocytes from the spleen of said immunized test animals. Fusion of B-lymphocytes with myeloma cells to produce hybridomas are known in the art and described in, e.g., Kohler et al., Nature 256:495 (1975), Making and Using Antibodies: A Practical Handbook (1st Ed., 2006). Selection of hybridomas for the desired binding characteristics are known in the art and described in, e.g., Kohler et al., Nature 256:495 (1975), Making and Using Antibodies: A Practical Handbook (1st Ed., 2006). A vast number of hybridoma cells producing an array of monoclonal antibodies may be obtained from public or private repositories. The largest depository agent is American Type Culture Collection, which offers a diverse collection of well-characterized hybridoma cell lines. In some embodiments the host cell is a hybridoma cell corresponding to ATCC deposit #PTA-120816 or PTA-120817.

Once introduced into a suitable host cell, expression of the invention antibody can be determined using any nucleic acid or protein assay known in the art. For example, the presence of transcribed mRNA of a light or heavy chain of the antibody can be detected and/or quantified by conventional hybridization assays (e.g. Northern blot analysis), amplification procedures (e.g. RT-PCR), SAGE (U.S. Pat. No. 5,695,937, hereby incorporated by reference), and array-based technologies (see e.g. U.S. Pat. Nos. 5,405,783, 5,412, 087 and 5,445,934, hereby incorporated by reference), using probes complementary to any region of the polynucleotide.

Expression of the vector can also be determined by examining the protein level of the antibody. A variety of techniques are available in the art for protein analysis. They include but are not limited binding assays, which are described herein, and SDS-PAGE analysis.

Methods of Producing Antibodies

The antibodies of the invention can be produced using any methods known to one of skill in the art (see, e.g., Making and Using Antibodies: A Practical Handbook (1$^{st}$ Ed., 2006)) or as described herein.

In some embodiments, the antibodies are generated by inoculating a test animal with an antigen polypeptide that comprises a portion of the TTR amino acid sequence. In some embodiments, the antigen is more accessible on monomeric and/or oligomeric TTR as compared to tetrameric TTR. Antigen accessibility can be ascertained by the formation of a complex between the antigen and the antibody. In some embodiments, formation of the complex is detected by a binding assay, e.g., an immunoassay. In some embodiments, the antigen comprises a plurality of consecutive amino acids between positions 1-100 of any wild-type or mutant TTR sequence. In some embodiments, the antigen comprises a plurality of consecutive amino acids between positions 5-90, 10-80, 20-70, or 30-66 of any wild-type or mutant TTR sequence. In other embodiments, the antigen comprises a plurality of consecutive amino acids between positions 60-127 of any wild-type or mutant TTR sequence. In other embodiments, the antigen comprises a plurality of consecutive amino acids between positions 70-127, 80-127, 90-127, 109-121, 100-127, 110-127, or 115-127 of any wild-type or mutant TTR sequence. In some embodiments, the antigen is 3, 4, 5, 6, 7, 8, 9, 10, 12, 14, 16, 18, 20, or more than 20 amino acids in length. In some embodiments, the antigen is 3-7, 4-10, 7-15, 10-20, 15-30, 20-40, 30-60, or more than 60 amino acids in length. In some embodiments, the antigen is synthesized using standard solid phase chemistry. In some cases the antigen sequence is chosen based on the crystal structure of TTR. By way of example only, a TTR polypeptide fragment that comprises an amino acid sequence that is predicted to be buried in the TTR tetramer but exposed in the dissociated monomer may be chosen as the antigen. Epitope prediction tools are described herein.

In some embodiments, the antigen may be a polypeptide designed with the aid of a design tool. Such tools include but are not limited to Expasy, which has aggregated a set of public tools under its ProtScale page, Antigen Profiler tool which enables a user to score individual peptide sequences based upon a relation epitope mapping database of previous immunogens used to generate antibodies. In some embodiments, the antigen may be designed to avoid certain amino acid sequences, such as, by way of example only, repeats of a single amino acid that are greater than 4 amino acids in length (e.g., RRRR (SEQ ID NO: 18)), Serine (S), Threonine (T), Alanine (A), and Valine (V) doublets, sequences starting or ending with Proline (P), or extremely hydrophobic peptides, such as, by way of non-limiting example, VALI (SEQ ID NO: 19)).

In some embodiments, small antigens (e.g., <10 daltons) are conjugated or crosslinked to larger, immunogenic, carrier proteins to increase immunogenicity. Examples of carrier proteins include, e.g. Keyhole limpet hemocyanin (KLH) and bovine serum albumin. In some embodiments, small peptide antigens are delivered using liposomes as a carrier.

The test animal can be any animal capable of generating an immune response to an antigen. Animal species frequently used for antibody production include chickens, goats, guinea pigs, hamsters, horses, mice, rats, rabbits, and sheep. One of skill in the art will understand that selection of the animal species may be based on a number of considerations, including but not limited to the amount of antibody needed, whether a monoclonal or polyclonal antibody is desired, the phylogenetic relationship between the donor species of the antigen and the species of the antibody producer (e.g., the more distant the phylogenetic relationship, the greater the potential for high titer antibody response) and the desired characteristics (e.g., class, subclass (isotype), titer) of the antibodies to be made.

Monoclonal antibodies can be generated according to conventional techniques, such as the hybridoma method, described in, e.g., Kohler et al., Nature 256:495 (1975), Making and Using Antibodies: A Practical Handbook (1$^{st}$ Ed., 2006), recombinant DNA methods as described in, e.g., U.S. Pat. No. 4,816,567, hereby incorporated by reference, and protein synthesis. In some embodiments, a nucleic acid that encodes the antibody is introduced into a host cell or a translation extract, and the host cell or extract is incubated under conditions whereby the nucleic acid is expressed as a translation product, and the antibody isolated.

Polyclonal antibodies can be generated according to conventional techniques. In some embodiments, the polyclonal antibodies are recombinant polyclonal antibodies. Recombinant polyclonal antibodies and methods of making the same are described in PCT application WO2009065414, WO2008145133, WO2006007853, WO2004061104 European Patent Nos. EP2152872, EP1583830, and U.S. Pat. No. 7,910,332 and U.S. Pat. No. 7,749,697, all of which are hereby incorporated by reference.

Uses of the Antibodies of the Present Invention

The antibodies of the present invention provide an effective means for the detection and measurement of non-native TTR. Such detection and measurement can be used for a wide range of applications, such as, e.g., diagnostic and/or therapeutic purposes. For example, the detection methods may be used for the identification of subjects that have increased likelihood of developing a disease, for diagnosing a disease, for improving accuracy of disease diagnosis in a subject harboring one or more symptoms that are shared by a plurality of diseases, for identification of subjects for early treatment for said disease, for monitoring the progression of the disease, for assessing the pharmacodynamic properties of a therapeutic agent, for determining the effectiveness of an therapy targeting said disease, for drug screening purposes, for aiding in the selection of a therapeutic regimen for the disease, for evaluating disease prognosis in a subject, or as a therapeutic agent.

In one embodiment, the invention provides a method for detecting an increased likelihood of developing an amyloid disease symptom in a subject that has not developed said amyloid disease symptom, e.g., is asymptomatic. In a related embodiment, the invention provides a method for the diagnosis of a disease in a subject who has developed a symptom of the disease, wherein the symptom is associated with a plurality of diseases. By way of example only, accurate diagnosis of SSA can be a challenge, as histological and symptomatic hallmarks of SSA are shared by other types of systemic amyloidoses. By way of other example only, histological and symptomatic hallmarks of FAC are shared by other types of cardiomyopathies, making diagnosis of FAC a challenge. Accordingly, the methods and antibodies of the present invention can, for example, provide a useful biomarker that can distinguish a TTR-related amyloidosis characterized by a symptom in common with other diseases from said other diseases. In these and other methods, the method comprises measuring a level of non-native TTR in said subject using an antibody of the invention. In some embodiments, said subject is designated as having an increased likelihood of developing said amyloid disease symptom or of having an amyloid disease if said level is increased as compared to a level of non-native TTR measured in a control subject. In other embodiments, said subject carrying certain mutations (e.g. V30M mutation) is designated as having an increased likelihood of developing said amyloid disease symptom or of having an amyloid disease if said non-native TTR level is changed (increased or decreased) over 20% as compared to a level of non-native TTR measured in the same subject at a previous time point.

Detection Methods:

In some embodiments, the methods of the present invention comprise detecting a level of non-native TTR in said subject. In some embodiments, the method for the early detection of a disease comprises measuring or quantifying a level of non-native TTR in said subject. In some embodiments, a level of non-native TTR in said subject is detected or measured with the aid of an antibody of the present invention. In other embodiments, a level of non-native TTR in said subject is detected or measured with the aid of any molecule that selectively binds to non-native TTR as compared to tetrameric TTR. Exemplary molecules include, e.g., aptamers.

In some embodiments, a level of non-native TTR is detected in said subject. In some embodiments, detecting a level of non-native TTR in a subject comprises detecting a level of non-native TTR in a biological sample obtained from said subject. In some embodiments, the biological sample is a liquid sample. In some embodiments, the liquid sample is whole blood, plasma, serum, ascites, cerebrospinal fluid, sweat, urine, tears, saliva, buccal sample, cavity or organ rinse. In other embodiments, the biological sample is a solid biological sample, e.g., feces or tissue biopsy.

In some embodiments, the antibody is employed in a binding assay such as, e.g., ELISA, immunoprecipitation, coprecipitation, western blotting, surface plasmon resonance, multiplex immunoassays, two-hybrid assay, immunohistochemistry assay, and the like. In some embodiments, the binding assay is an ELISA assay. Such assays are known in the art and described in The Immunoassay Handbook, $4^{th}$ Ed. (2005). Detection may employ the use of detectable labels, such as, e.g., fluorescent compounds, chemiluminescent compounds, bioluminescent compounds, enzymes, radioisotopes, colloidal metals, paramagnetic labels. Detection methods as described herein can enable the sensitive, quantitative detection of rare non-native TTR in a sample. By way of example only, detection methods as described herein can enable the quantitative detection of 0.01 ng-100 μg/ml TTR in a sample, 10 ng-500 μg/ml TTR in a sample, and/or 100 ng-1000 mg/ml 1 TTR in a sample. Such sensitive detection methods can aid in the early diagnosis of TTR-related amyloidosis in a subject.

Figure 2:
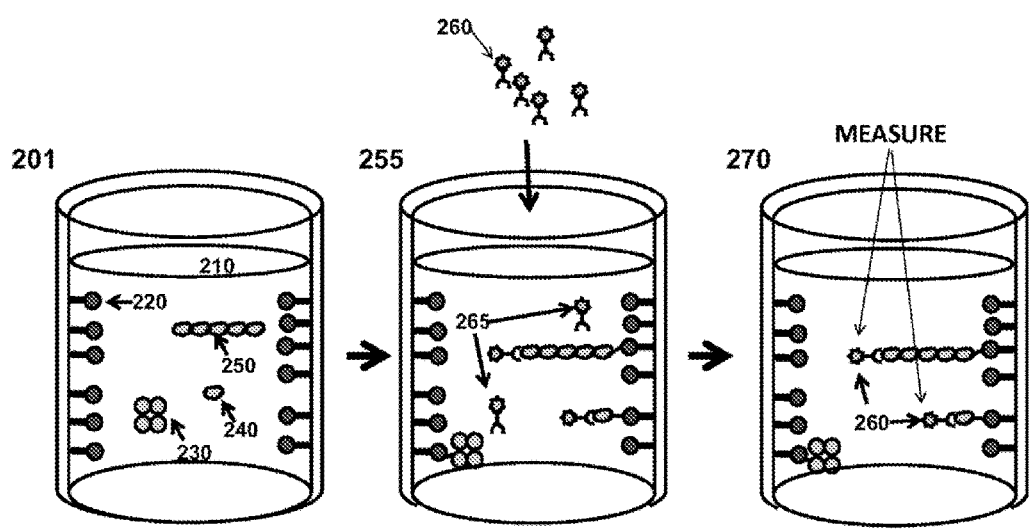
FIG. 2 depicts an exemplary binding assay for the detection of non-native TTR.

In particular embodiments, the ELISA assay is an indirect (e.g., sandwich) assay. FIG. 2 provides a schematic diagram (200) of an exemplary sandwich-type ELISA assay utilizing the antibody of the present invention. In some embodiments, the method comprises a first step (201) of adding a liquid sample 210 obtained from a subject to a well immobilized thereon a capture antibody 220 capable of binding to TTR. In some embodiments the liquid sample 210 comprises a heterogeneous mixture of tetrameric TTR (230) and non-native TTR (e.g., monomeric TTR (240) and oligomeric TTR (250)). In some embodiments, the capture antibody 220 is capable of binding to non-native and tetrameric TTR. In other embodiments, the capture antibody 220 exhibits selective binding to non-native TTR. The non-native and tetrameric TTR in said liquid sample 210 are allowed to form a binding complex to the capture antibody 220, thereby immobilizing said non-native and/or tetrameric TTR onto said well. In a second step (255), a detection antibody (260) is added to the well. In some embodiments, the detection antibody is capable of selective binding to non-native TTR as compared to tetrameric TTR. In other embodiments, the detection antibody exhibits binding to non-native and/or tetrameric TTR. In some embodiments, the method further comprises incubating the mixture for a sufficient period of time as to allow the formation of a complex comprising non-native TTR and the detection antibody 260. In some embodiments, the method further comprises removing uncomplexed detection antibody 165 from said well in a series of wash steps. In a third step (270), a level of complexed detection antibody 260 remaining in the well is detected and/or measured by any means known in the art. In some embodiments, the level of complexed detection antibody 260 remaining in the well is proportional to the amount of non-native TTR present in the liquid sample.

Table 2 summarizes the various capture and detection antibody combinations used in the invention.

TABLE 2

Exemplary capture/detection antibody combinations

| Capturing Antibody | Example of detection Antibodies |
|---|---|
| MFD114 | MFD102 or similar (bind epitope 1) |
|  | MFD108 or similar (bind epitope 2) |
|  | MFD112 |
|  | MFD113 |
|  | MFD114 |
| MFD113 | MFD102 or similar (bind epitope 1) |
|  | MFD108 or similar (bind epitope 2) |
|  | MFD113 |
|  | MFD114 |
| MFD112 | MFD102 or similar (bind epitope 1) |
|  | MFD108 or similar (bind epitope 2) |
|  | MFD112 |
|  | MFD114 |
| MFD102 or similar (bind epitope 1) | MFD114 |
|  | MFD113 |
|  | MFD112 |
|  | MFD102 or similar (bind epitope 1) |
|  | MFD108 or similar (bind epitope 2) |
| MFD108 or similar (bind epitope 2) | MFD114 |
|  | MFD113 |
|  | MFD112 |
|  | MFD102 or similar (bind epitope 1) |
|  | MFD108 or similar (bind epitope 2) |

In some embodiments, a binding assay is used to detect a level of non-native TTR in a solid biological sample, e.g., tissue biopsy. In some embodiments, the solid biological sample is homogenized prior to the binding assay, .e.g., a sandwich ELISA assay as described herein. In some embodiments, additives are added to a blocking buffer as well as the biological samples during the ELISA experiment to minimize non-specific binding or interferences including but not limited to heterophilic interactions. Such additives include carrier proteins (e.g. bovine serum albumin, casein), detergent (e.g. Tween-20), pooled normal plasma, polypropylene glycol, protein A/G, non-specific mouse antibodies, non-specific rabbit antibodies, as well as commercial sources of blocking reagents that serve such purposes. In other embodiments, the solid biological sample is not homogenized. In some embodiments, the binding assay is an immunohistochemistry assay. Immunohistochemistry assays may be performed as described herein or by any means known in the art.

In general, an immunohistochemistry assay comprises collecting a tissue biopsy sample, and preserving said tissue biopsy sample to prevent breakdown of cellular protein and tissue architecture. Preservation of said tissue biopsy sample may involve removal of blood, e.g., by perfusion or rinsing. Preservation of tissue biopsy sample may also involve contacting said sample with a preservative, such as, .e.g., formaldehyde, paraformaldehyde, glutaraldehyde, one or more alcohols such as, e.g., ethanol, methanol, acetone, acetic acid, osmium tetroxide, potassium dichromate, chromic acid, potassium permangamate, picrates solution, or Hepes-glutamic acid buffer-mediated organic solvent protection effect fixative. The tissue sample may be further prepared by tissue sectioning, e.g., into tissue slices of substantially uniform thickness (e.g., 1-10 microns, 7-20 microns, 10-50 microns, 30-100 microns, 50-200 microns, 100-500 microns, or greater than 500 microns). In some embodiments, the tissue sections are washed in a wash buffer comprising a buffered solution, e.g., a phosphate buffer solution, followed by incubation with a blocking agent that blocks non-specific antibody binding. In some embodiments, the immunohistochemistry assay comprises contacting the tissue sections with an antibody of the present invention to effect formation of a binding complex between said antibody and a TTR non-native protein conformation. Non-specifically bound antibody may be removed in one or more wash steps, and the binding complex may be detected by any means known in the art.

In some embodiments, non-native TTR is detected directly in the subject, e.g., by in vivo imaging. By way of example only, an antibody of the present invention can be conjugated to a detectable label. The labeled antibody can be introduced in the body of the subject, e.g., by injection into said subject, and detected in the subject in vivo. The subject can be imaged using an apparatus that is configured to detect the detectable label. By way of example only, the antibody can be conjugated to an MRI contrast agent. The conjugated antibody can be introduced into the subject for imaging by MRI. By way of other example only, the antibody can be conjugated to a radioactive isotope suitable for PET imaging. The conjugated antibody can then be introduced into the subject for imaging by PET scan. By way of yet other example, the antibody can be labeled with a fluorophore, e.g., a near-infrared fluorophore. The conjugated antibody can then be introduced into the subject for fluorescence imaging, e.g., near-infrared fluorescent imaging.

In some embodiments, detection is based on a detected level of non-native TTR above a background level as determined by samples that are known not to contain TTR (e.g., wells that contain reaction components only). In some embodiments, a level of non-native TTR can be quantified by quantifying a detectable signal. In some embodiments a level of non-native TTR can be quantified by comparing said detectable signal to a signal generated by samples containing known amounts of non-native TTR. In some embodiments, a level of non-native TTR can be normalized to total TTR levels by ratiometric analysis, e.g., by comparing a signal generated by contacting a sample with an antibody of the invention vs. a signal generating by contacting said sample with an antibody that binds only tetrameric TTR or that binds to non-native and tetrameric TTR with similar affinity or avidity.

In some embodiments, designation of said subject as having an increased likelihood of developing an amyloid disease symptom, or designation of said subject as having an amyloid disease, comprises comparing a level of non-native TTR in said subject to a level of non-native TTR in a control subject. If a level of non-native TTR in said subject is greater than a level of non-native TTR in a control subject, said subject can be designated as having an increased likelihood of developing an amyloid disease symptom or designated as having an amyloid disease. The control subject can be an individual known not to harbor an amyloid disease, or known not to harbor a TTR mutation. The control subject can be an age-matched control subject, e.g., within 0-10 years of age as said subject, or the control subject can be of a different age, e.g., a younger or older age than said subject. The control subject does not have to be a different individual from said subject, but may be the same subject at an earlier time point, e.g., within an age bracket that is not considered to be a risk factor for developing said disease or said disease symptom. Age brackets that can be considered as risk factors are described herein. In some embodiments, a level of non-native TTR in said subject may be compared to an expected level of a control subject. In some embodiments, said expected level is a non-detectable level. Accordingly, a subject can be designated as having a disease or having an increased likelihood of developing a disease if non-native TTR is detected in said subject. During the process of amyloidogenesis, the level of non-native TTR level as detected herein is influenced by multiple factors including but not limited to the formation of amyloid deposit, which may act either as a sink or reservoir for non-native TTR in the circulation. Therefore, the level of non-native TTR changes over time in an amyloid disease carrier. In some embodiments, when the said control subject is the same individual at an earlier age, an alteration, e.g., an increase of over 10%, 20%, 30%, 40%, 50%, 100%, 200%, 500% or more of a level of non-native TTR may also signal an increased likelihood of developing an amyloid disease symptom, or designation of said subject as having an amyloid disease. In some embodiments, a detected fluctuation in the level of non-native TTR (e.g., a transient decrease or increase) indicates an increased likelihood of developing an amyloid disease symptom. In some embodiments, a detected fluctuation in the level of non-native TTR in a subject is used to designate said subject as having an amyloid disease.

Amyloid diseases are described herein. The disease can be an amyloid disease associated with amyloidogenic TTR. Exemplary amyloidogenic TTR-associated diseases are described herein.

In some embodiments, the methods described herein further comprise alerting the subject or a caregiver thereof of said designation. Methods of alerting are described herein.

Subjects

The term "subject" encompasses any biological entity that carries one or more forms of TTR. In some embodiments, the subject is an animal. In some embodiments the animal is a vertebrate, such as a mammal, amphibian, bird, or reptile. Exemplary mammals include, e.g., a mouse, rat, rabbit, guinea pig, dog, cat, pig, sheep, horse, cow, human, or monkey. Exemplary amphibians include, e.g., frogs, toads, salamanders, and newts. Exemplary reptiles include, e.g., snakes, lizards, turtles. Exemplary birds include, e.g., chickens, waterfowl, finches, songbirds. In some embodiments, the subject is an invertebrate, e.g., *C. elegans* or insect such as, e.g., *Drosophila melongaster*.

In some embodiments, the subject is suspected of having a disease or of having an increased likelihood of developing a disease symptom based on any combination of a number of risk factors, symptoms, assays, and tests described below. In related methods, the subject has been diagnosed with an amyloid disease and is undergoing an anti-aggregate therapy.

One of ordinary skill in the art will understand that the presence or absence of risk factors, symptoms, assays, and tests described below may also be used as an aid to monitor the progression of the disease or to monitor a therapeutic effect of an agent.

The subject may be considered to be at increased risk for having a disease or disease symptom and selected to undergo diagnostic testing using any of the methods of the invention, based on any combination of risk factors associated with the disease. The presence of any combination of risk factors described herein can be used to aid in the diagnosis of the subject based on use of any of the antibodies described herein. One of ordinary skill in the art will understand that a greater number of risk factors that can be applied to a subject may correlate with greater risk of the subject developing the disease, however, a subject may be considered to be at increased risk for developing the disease based on even one of the risk factors described herein. A subject can also be selected to undergo diagnostic testing without presenting any of the risk factors described herein.

In some embodiments, the subject is considered to be at increased risk for developing a disease upon detection of a TTR mutation in said subject. TTR mutations associated with increased risk for developing, e.g., FAP or FAC are described herein. One of skill in the art will understand that de novo (i.e. —new) mutations of TTR may be discovered as being associated with a disease, and that detection of these new mutations in a subject may indicate that said subject is at increased risk for developing the disease or symptom(s) of the disease.

Detection of a TTR mutation can be performed using any means known in the art and may include but are not limited to genotyping methods, exome or genome sequencing methods, including next-generation sequencing methods, or haplotype analysis.

In some embodiments, mutant or variant TTR is detected by detecting a difference in TTR protein molecular weight as compared to wild-type TTR molecular weight. Differences in TTR molecular weight can be detected by any method described herein or known in the art, including but not limited to mass spectroscopy, electrospray ionization mass spectroscopy, size-based chromatography, and size-based electrophoresis. The difference in molecular weight can be a difference of about 1, 2, 3, 4, 5, 6, 7, 8, 9, 10, 12, 14, 16, 18, 20, 25, 30, 30, 35, 40, 45, 50, 55, 60, 65, 70, 75, 80, 85, 90, 95, 100, 125, 150, 175, 200, 250, 300, 350, 400, 450, 500, 600, 700, 800, 900, 1000, or over 1000 daltons. The difference in molecular weight can be a difference of 1-10 daltons, 2-20 daltons, 5-30 daltons, 10-50 daltons, 20-100 daltons, 50-200 daltons, 100-500 daltons (0.5 kDa), 200-1000 daltons (1kDA), 0.5-5 kDa, or greater than 5 kDa. In some embodiments, the difference in molecular weight is equal to or greater than 1, 2, 3, 4, 5, 6, 7, 8, 9, 10, 12, 14, 16, 18, 20, or more than 20 daltons. In preferred embodiments, the difference in molecular weight is equal to or greater than 10 daltons. In particular embodiments, the difference in molecular weight is an increase of 26 daltons as compared to wild-type TTR.

In other embodiments, TTR mutations are detected by a change in isoelectric point as compared to wild-type TTR. Such changes in isoelectric point can be detected by any methods described herein or known in the art, such as, e.g., isoelectric focusing. In some embodiments, proteins in a biological sample obtained from a subject are subjected to size-based separation by electrophoresis, and are further separated according to isoelectric point by isoelectric focusing, e.g., by isoelectric focusing using a urea gradient.

In some embodiments, the TTR mutation or variant is detected by analysis of a biological sample obtained from said subject. The biological sample can be a fluid sample, e.g., whole blood, plasma, serum, ascites, cerebrospinal fluid, sweat, urine, tears, saliva, buccal sample. The biological sample can also be a solid biological sample, e.g., feces or tissue biopsy.

In some embodiments, the subject is considered to be at increased risk for developing a disease based on geographic/race factors. By way of example only, there is a high prevalence of TTR variants in Portugal, Sweden, and Japan. Therefore, a subject can be considered to be at increased risk for developing a disease if said subject is Portuguese, Swedish, or Japanese. By way of other example, there is a high prevalence of the V122I TTR variant in Africans and African Americans as compared to Caucasians. The V122I TTR variant is generally associated with FAC with little or no neuropathic symptoms. Therefore, a subject can be considered to be at increased risk for developing a disease, e.g., FAC, if said subject is of African descent. By way of other example only, a L111M TTR mutation has been reported in Danish kindred as being associated with exclusive cardiac involvement. Therefore, a subject can be considered to be at increased risk for developing a disease, e.g., a cardiac disease, if said subject is of Danish descent.

In some embodiments, a subject is considered to be at increased risk for developing a disease or a disease symptom if the subject has a family history of a disease. In some embodiments, a family history of a disease involves any relative of the subject being diagnosed or suspected of having a disease. In some embodiments, a family history of a disease includes an immediate family member having been diagnosed or suspected of having a disease. In some embodiments, the family member diagnosed or suspected of having a disease is a parent, grandparent, great-grandparent, or family member from a yet even older generation. In some embodiments, the family member is a sibling. In particular embodiments, the sibling is an identical twin. In some embodiments, the family member is a son or daughter, or a grandchild or family member from a yet even younger generation. In some embodiments, the family member is outside the immediate family, e.g., a first cousin, a second cousin, a third cousin, an aunt, an uncle, a second or third aunt, a second or third uncle, a niece, a nephew, a second or third niece, a second or third nephew.

In some embodiments, a subject is considered to be at increased risk for developing a disease or disease symptom based on age of said subject. For example, FAP typically strikes from 20-40 years of age. In some embodiments, a subject may be considered to be at increased risk for developing a symptom of FAP if said subject is between about 20-40 years of age. By way of other example, FAC typically strikes older individuals (e.g., 60 or above). In some embodiments, a subject is considered to be at increased risk for developing a symptom of FAC if said subject is about 40, 45, 50, 55, or 60 years or older. By way of yet another example, SSA is highly prevalent in individuals aged 80 or above. In some embodiments, a subject is considered to be at increased risk for developing a symptom of SSA if said subject is about 60, 65, 70, 75, or 80 years of age or older.

In some cases, subjects with FAP or FAC present symptoms of carpal tunnel syndrome prior to developing polyneuropathy or cardiomyopathy symptoms. Therefore, in some embodiments, a subject is considered to be at increased risk for developing a symptom of FAP or FAC if said subject exhibits a symptom of carpal tunnel syndrome. Symptoms of carpal tunnel syndrome include, but are not limited to pain, numbness, tingling, or weakness in the hand or fingers.

Symptoms

In some embodiments, said subject has suffered or is suffering from a disease symptom. In some cases, symptoms of a disease can be ascertained by a physical exam, subject self-report, neurological exam, medical history, electrophysiological test, lab assay, or imaging. In some cases, a physical exam or medical history will include an assessment or history of symptoms. In some cases, the neurological exam will include an assessment of the patient's vision, reflexes, balance, coordination, and/or muscle strength. Such laboratory tests can include tests of nerve function, e.g., electromyography with nerve conduction studies. Described herein are exemplary diseases and characteristic symptoms of said diseases. One of ordinary skill in the art will understand that symptoms of a disease can manifest in a wide variety of ways and that the symptoms described herein for each disease is not meant to be an exhaustive list of symptoms.

In some embodiments, the symptom of the disease is a symptom characteristic of FAP. FAP is a progressive degenerative disease that typically strikes between age 20-40 and causes progressive peripheral nerve degeneration. Symptoms of FAP can be due to sensory and/or autonomic nerve dysfunction. Sensorimotor symptoms of FAP can begin in the lower extremities of the subject and ascend laterally, and can include but are not limited to polyneuropathy, impaired sensation, e.g., impaired pain sensation, impaired temperature sensation, impaired touch sensation (e.g., numbness), or painful parasthesias (i.e. —unusual sensations such as, e.g., pins and needles sensation), balance difficulties, difficulty walking, Symptoms of autonomic nerve dysfunction can include, but are not limited to nausea, vomiting, constipation, urinary incontinence or urinary retention, nephropathy, weight loss (e.g., wasting away), sweating abnormalities, e.g., inability to sweat, sexual dysfunction (e.g., impotence), a high blood prealbumin level, foot ulcers, diarrhea, carpal tunnel syndrome, delayed gastric emptying, and orthostatic hypotension. As the disease progresses, symptoms can include central nervous system manifestations such as, e.g., hydrocephalus, dementia, psychosis, seizures, visual impairment, ataxia and cardiomyopathy.

In some embodiments, the symptom of the disease is characteristic of a leptomeningeal form of amyloidosis. The leptomeningeal form generally spares sensory and autonomic function, however, amyloid deposits on CNS tissues can cause symptoms such as, by way of non-limiting example only, hydrocephalus, seizures, ataxia, dementia, psychosis, motor impairment, and/or intracranial hemorrhage.

Methods of assessing one or more symptoms of FAP are known in the art and include, the Neuropathy Impairment Score-Lower Limbs (NIS-LL), which quantifies motor, sensory, and reflex functions in the lower limbs. Lower limb motor and sensory impairment are another exemplary symptomatic hallmark of early-stage FAP.

Other tests can involve skin biopsy to evaluate cutaneous nerve innervations, or nerve and muscle biopsy. Such tests can detect degeneration of affected nerves, e.g., axonal degeneration.

In other embodiments, the symptom of the disease is characteristic of FAC (familial amyloid cardiomyopathy). Cardiomyopathy generally refers to a deterioration of heart muscle (i.e. —myocardium) function. Said deterioration may occur for any reason. Cardiomyopathy can result in heart failure. Symptoms of cardiomyopathy include, e.g., dyspnea (i.e. —breathlessness), peripheral edema (i.e. —swelling of the legs), irregular heart beat. In some cases, FAC symptoms are preceded by carpal tunnel syndrome. Subjects with cardiomyopathy are at increased risk for congestive heart failure and sudden cardiac death. Many FAC patients also exhibit polyneuropathy and autonomic nervous system dysfunction.

Symptoms of FAC may be ascertained by, e.g., patient self-report, clinical examination, and/or laboratory tests. Such laboratory tests can include echocardiography, ECG, or in vivo imaging, e.g., MRI.

In some cases, onset of FAC symptoms occurs around or after age 60. Symptoms of FAC may include the presence of conduction system disease (e.g., sinus node or atrioventricular node dysfunction) congestive heart failure, shortness of breath, peripheral edema, syncope, exertional dyspnea, generalized fatigue, or heart block. In some embodiments, symptoms of FAC include a low ECG voltage, axis deviation, bundle branch block, AV block, and atrial fibrillation.

In other embodiments, the symptom of the disease is characteristic of SSA. SSA symptoms include, e.g., include congestive heart failure, arrhythmias, and conduction defects, and may include one or more symptoms of FAC, described herein.

In other embodiments, the symptom of the disease is characteristic of familial oculoleptomeningeal amyloidosis. Familial oculoleptomeningeal amyloidosis symptoms include, e.g., central nervous system dysfunction, brain hemorrhage, vision impairment, nystagmus, dementia, seizures, coma, stroke, headache, ataxia, tremor, deafness, dysarthria, and spasticity.

Symptoms of any of the diseases described herein can also include the presence of amyloid deposits in affected tissue (e.g., nerves, leptomeningeal blood vessels, brainstem, spinal cord, eye, fat pad, and heart tissue). By way of example only, familial amyloid neuropathy progresses, amyloid deposits can be detected in other organs and organ systems such as, e.g., the heart, kidneys, salivary gland and digestive tract. Amyloid deposition in these organs can worsen and cause dysfunction of these organ systems, such as, e.g., infectious disease, heart failure, and renal insufficiency. In some embodiments, the presence of amyloid deposits in nerves or other tissue can be detected using any method known in the art or described herein. Such methods include, by way of non-limiting example only, staining a biological sample obtained from a subject with an amyloid-specific dye, or in vivo imaging of a live subject with an amyloid-specific imaging agent.

Amyloid-specific dyes include, e.g., Congo Red, thioflavin S, thioflavin T, curcumin, acridine orange, fluorine, DDNP, (trans, trans)-1-bromo-2,5-bis-(3-hydroxycarbonyl4-hydroxy)-styrylbenzene (BSB), chyrsamine G, and any analogs and derivatives thereof. Congo red stained amyloid is generally characterized by a dichroic appearance exhibiting a yellow-green polarization color, resulting from the beta-pleated sheet structure of the amyloid. Further description of the biochemistry and histochemistry of amyloid can be found in Glenner, G., N. Eng. J. Med., 302: 1333 (1980).

Amyloid-specific imaging agents include, e.g., radiopharmaceutical imaging agents such as but not limited to radio-labeled flutemetamol, florbetapir, and florbetaben. Exemplary amyloid-specific imaging agents and imaging methods are described in U.S. Pat. Nos. 7,311,893, 6,001,331, 7,425, 318, 7,700,616, 7,029,655 United States Patent Application Nos. 20090123373, 20060035946

In particular embodiments, the detected amyloid deposit comprises TTR protein, as evidenced by co-localization of amyloid-specific dye or imaging agent with a TTR-specific marker TTR-specific markers include TTR-specific antibodies which may or may not be complexed with a detectable label. In some embodiments, the TTR-specific antibody is an antibody of the invention.

In related embodiments, the invention provides a method for treating an amyloid disease in a subject in need thereof, comprising: administering an anti-aggregate agent to said subject upon detection of non-native TTR in said subject. In another related embodiment, the invention provides a method of assessing the efficacy of an anti-aggregate therapy applied to a subject, comprising: measuring a change in the level of non-native TTR in said subject during said therapy, wherein a decrease in the level of non-native TTR during said therapy indicates that said therapy is efficacious. In some embodiments, an increase in the level of non-native TTR during said therapy indicates that said therapy is not efficacious. Accordingly, the invention provides a method for administering an anti-aggregate agent to a subject in need thereof, comprising: administering said anti-aggregate agent to said subject at multiple time points, measuring a level of non-native TTR in said subject upon at least a first and second time point of said administration, and adjusting dosage of said anti-aggregate agent and/or selecting a different anti-aggregate agent for administration based on said detected level of non-native TTR. In preferred embodiments, detection or measurement of non-native TTR in said subject is performed using an antibody of the invention.

The terms "treating", "treatment", or "therapy" are used interchangeably to refer to utilizing a method or methods to achieve a therapeutic benefit and/or a prophylactic benefit. In some cases, a therapeutic benefit may refer to reducing the severity of a symptom or symptoms of a disease. In some cases, a therapeutic benefit may refer to addressing or correcting the biological mechanisms underlying the disease. In other cases, a therapeutic benefit may refer to halting or slowing the progression of the disease. In addition, a prophylactic benefit may refer to reducing the risk of developing a symptom of the disease. In some cases, a prophylactic benefit may refer to delaying the onset of symptom(s) of the disease.

Anti-Aggregate Agents/Therapies

As used herein, "agent" refers to a biological, pharmaceutical, or chemical compound or other moiety. Non-limiting examples include a simple or complex organic or inorganic molecule, a peptide, a protein, an oligonucleotide, an antibody, an antibody derivative, an antibody fragment, a vitamin or vitamin derivative, a carbohydrate, a toxin, a chemotherapeutic compound, or a vaccine. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. One of skill in the art can readily recognize that there is no limit as to the structural nature of the agents of the present invention.

A wide range of anti-aggregate agents and therapies are known in the art, and are contemplated in the invention. In practicing the invention, any anti-aggregate agent that results in a therapeutic benefit to a subject having a disease or having an increased risk of developing a disease symptom as described herein is within the scope of the invention. Described below are exemplary anti-aggregate agents and therapies. The anti-aggregate agents and therapies described herein are not meant to be an exhaustive list of anti-aggregate agents and therapies.

In some embodiments, the anti-aggregate agent is a kinetic stabilizer that stabilizes the TTR tetramer and prevents its dissociation into monomers. In other embodiments, the anti-aggregate agent is an agent that prevents the association of TTR monomers into TTR oligomers, or prevents the association of TTR oligomers into protofibrils, or prevents the association of TTR protofibrils into fibrils and/or amyloid deposits.

Exemplary kinetic stabilizers are described in U.S. Pat. Nos. 7,214,696, 7,560,488, 7,214,695, 7,868,033, U.S. patent application Ser. No. 11/504,134, WIPO Patent Application Nos. WO/2011/140333. Exemplary kinetic stabilizers include, e.g., biphenyl amines, biphenyls, oxime ethers, benzazoles or other structures composed of two aromatic rings where one bears hydrophilic groups such as an acid or a phenol and the other bears hydrophobic groups such as halogens or alkyls. Additional exemplary kinetic stabilizers include, e.g., ortho-trifluormethylphenyl anthranilic acid and N-(meta-trifluoromethylphenyl) phenoxazine 4, 6-dicarboxylic acid.

In some embodiments, the kinetic stabilizer selectively binds and stabilizes native TTR. Such kinetic stabilizers include, by way of non-limiting example only, biaryl reagents, e.g., biaryl amine, polychlorinated biphenyls, diflunisal analogs, benzoxazoles such as, e.g., tafamidis.

In some embodiments, the compound is a biaryl reagent where one ring bears one or more hydrophilic substituents and the other ring comprises one or more hydrophobic substituents. In some embodiments, both rings of the biaryl reagent beat one or more hydrophilic substituents. The hydrophilic group can be a phenol, a COOH, a benzyl alcohol, a boronic acid or ester, a tetrazole, an aldehyde, a hydrated aldehyde, or any functional group that serves as either a H-bond donor or acceptor to the protein. In some embodiments, the biaryl reagent is a symmetrical biaryl reagent.

In some embodiments, the kinetic stabilizer is a non-steroidal anti-inflammatory agent. In some embodiments, the non-steroidal anti-inflammatory agent is diclofenac, flurbiprofen, diflunisal, or resveratrol.

In one embodiment, the kinetic stabilizer is diflunisal, or a pharmaceutically acceptable salt, derivative, metabolite, analog, or solvate thereof.

In one embodiment, the kinetic stabilizer is tafamidis, or a pharmaceutically acceptable salt, derivative, metabolite, analog, or solvate thereof.

In some embodiments, the kinetic stabilizer is an isoflavone, or a pharmaceutically acceptable salt, derivative, metabolite, analog, or solvate thereof. In one embodiment, the isoflavone is genisteine.

In some embodiments, the agent prevents the formation of TTR protofibrils, fibrils and/or amyloid deposits. Such agents have been described in Adamski-Werner, S. L.; et al. J. Med. Chem. 2004, 47, 355-374; Baures, P. W.; et al. Bioorg. Med. Chem. 1999, 7, 1339-1347; Baures, P. W.; Peterson, S. A.; Kelly, J. W. Bioorg. Med. Chem. 1998, 6, 1389-1401; Johnson, S. M.; et al. J. Med. Chem. 2005; Klabunde, T.; et al. Nat. Struct. Biol. 2000, 7, 312-321; Oza, V. B.; et al. J. Med. Chem. 2002, 45, 321-332; Peterson, S. A.; et al. Proc. Natl. Acad. Sci. USA 1998, 95, 12956-12960; Petrassi, H. M.; et al. J. Am. Chem. Soc. 2000, 122, 2178-2192; Razavi, H.; et al. Bioorg. Med. Chem. 2005, 15, 1075-1078; Razavi, H.; et al. Angew. Chem. Int. Ed. Engl. 2003, 42, 2758-2761; Wiseman, R. L.; et al. J. Am. Chem. Soc. 2005), all of which are incorporated by reference. Exemplary agents include, e.g., epigallocatechin-3-gallate, curcumin and nordihydroguaiaretic acid.

In some embodiments, the agent inhibits toxicity of an amyloidogenic protein or inhibits formation of an amyloidogenic protein deposit. Such agents are described in U.S. Pat. Nos. 7,901,683, 7,053,116, U.S. patent application Ser. No. 11/103,656, Hsiao Y. H., et. al, J Neurosci Res. 2008 September; 86(12):2685-95.

Exemplary agents that can inhibit toxicity of an amyloid protein deposit include, but are not limited to amyloid beta sheet mimics, antioxidant, and other agents. Exemplary agents are described in PCT application publication number WO/2008/141074 and U.S. patent application Ser. No. 12/687,455.

Inflammation can be a hallmark of amyloid toxicity. Therefore, agents that reduce inflammation can be used as an anti-aggregate agent. Exemplary agents that reduce inflammation are described in, e.g., U.S. application Ser. No. 10/314,428. Exemplary anti-inflammatory agents include but are not limited to lipoxygenase inhibitor, such as an inhibitor of 5-lipoxygenase, a cyclooxygenase inhibitor, such as a cyclooxygenase-2 inhibitor, an interleukin receptor antagonist, such as an interleukin-1 receptor antagonist, an NMDA receptor antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sulindac, tenidap, steroids such as beclomethasone, methylprednisolone, betamethasone, prednisone, dexamethasone, and hydrocortisone; non-steroidal anti-inflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen.

Amyloid beta sheet mimics inhibit aggregation of amyloidogenic proteins and reduce amyloid toxicity. In some embodiments, the anti-aggregate agent is an amyloid beta sheet mimic (ABSM). Exemplary ABSMs are described in Cheng, P N et al, Nature Chemistry 4, 927-933(2012).

In some embodiments, the anti-aggregate therapy comprises a liver transplantation.

In some embodiments, the anti-aggregate therapy comprises domino liver transplantation.

In some embodiments, the anti-aggregate therapy comprises administration of an anti-TTR agent intended at reducing total TTR protein level. The anti-TTR agent can be any agent that inhibits expression of TTR, e.g., by reducing translation of TTR mRNA or by causing the degradation of TTR mRNA. The anti-TTR agent can be a nucleic acid, a protein, a polypeptide, a chemical compound, or any combination thereof. Exemplary nucleic acid molecules that can be used to inhibit expression include double stranded ribonucleic acid (dsRNA) or anti-sense oligonucleotides that target TTR. In some embodiments, the dsRNA includes an antisense strand having a regions which is complementary to at least a portion of TTR mRNA, which may include a 5' UTR, an open reading frame (ORF), or a 3' UTR. Exemplary dsRNA agents targeting TTR are described in U.S. Pat. Nos. 8,283,460, 7,250,496, U.S. patent application Ser. Nos. 12/273,731; 13/503,843; 12/582,669; WO 2010/048228 (International application no. PCT/US2009/061381, filed Oct. 20, 2009) and WO/2011/123468. Anti-sense oligonucleotides that target TTR can be any oligonucleotide sequence having a sequence that is complementary to at least five contiguous nucleotides in the TTR mRNA sequence.

In some embodiments, administration of an anti-TTR agent reduces TTR protein level or mRNA level in a subject, or in a biological sample obtained from said subject, by about 10%, 15%, 20%, 25%, 30%, 35%, 40%, 45%, 50%, 55%, 60%, 65%, 70%, 75%, 80%, 90%, 95%, or more than 95%. TTR protein level can be ascertained by any means known in the art, including, e.g., a binding assay using an antibody that selectively binds TTR as compared to other polypeptides, an RT-PCR assay, an in situ hybridization assay, or an RNase protection assay.

In some embodiments, the anti-TTR agent is an agent that inhibits the translation of TTR. Exemplary agents include, e.g., RXR/RAR agonists, RXR/RAR antagonists, estrogen agonists, estrogen antagonists, testosterone agonists, testosterone antagonists, progesterone agonists, progesterone antagonists, dexamethasone agonists, dexamethasone antagonists, antisense oligonucleotides, siRNA, shRNA, dsRNA, miRNA, fatty acid binding protein antagonists, C/EBP agonists, C/EBP antagonists, HNF-1 agonists, HNF-1 antagonists, HNF-3 agonists, HNF-3 antagonists, HNF-4 agonists, HNF-4 antagonists, HNF-6 agonists, HNF-6 antagonists, aptamers, ribozymes and monoclonal antibodies. Exemplary agents are described in U.S. patent application Ser. No. 11/296,909.

In some embodiments, the therapy comprises administration of an agent that promotes folding of a non-native protein conformation into a native conformation. In particular embodiments, the agent is a molecular chaperone. Molecular chaperones generally refer to proteins or other molecules that assist the non-covalent folding or unfolding of macromolecular structures such as, e.g., proteins and small molecule (chemical) chaperones. Chaperone proteins include heat shock proteins such as, e.g., HSP60, HSP70, HSP90, HSP100, BiP, GRP94, GRP170, calnexin and calreticulin, Protein disulfide isomerase (PDI), Peptidyl prolyl cis-trans-isomerase (PPI), and ERp57. Chemical chaperones include methylamines such as, e.g., trimethylamine N-oxide (TMAO), betaine, glycine betaine, and glycero-phosphorylcholine, carbohydrates such as, e.g., glycerol, glycerol, sorbitol, arabitol, myo-inositol and trehalose, choline, 4-Phenyl butyric acid, and taurine-conjugated ursodeoxycholic acid.

In some embodiments, the therapy comprises administration of an agent that modulates endoplasmic reticulum (ER) stress. ER stress refers to an accumulation of unfolded or misfolded proteins in the endoplasmic reticulum, leading to activation of an unfolded protein response (UPR) pathway. The UPR pathway is an evolutionarily conserved pathway that, in some cases, reduces ER stress by inhibition of protein translation and activation of genes that assist in protein folding (e.g., protein chaperones, such as those described herein). In some embodiments, the agent activates the UPR pathway or activates the expression of genes that assist in protein folding.

In some embodiments, the therapy comprises administration of an agent that modulates the ubiquitin proteosome pathway (UPS pathway). Exemplary modulators of the UPS pathway include, e.g., proteosome inhibitors such as, e.g., bortezomib, peptide boronic acids and esters, disulfiram, epigallocatechin-3-gallate, salinosporamide A, carfilzomib, ONX 0912, CEP-18770, and MLN9708. Other exemplary agents can include proteins that activate the proteosome, such as, e.g., the proteasome activator subunit PA28γ, members of the proteosome activator protein families US and Blm10, 19S activator, or agents that increase expression of said proteins.

In some embodiments, the therapy comprises administration of an agent that modulates the acute phase response. Generally, the acute phase response refers to the increase or decrease of acute phase proteins in response to inflammation. Exemplary acute phase response proteins that are increased in response to inflammation includes, e.g., C-reactive protein, serum amyloid P component, serum amyloid A, complement factors, mannan-binding lectin, fibrinogen, prothrombin, factor VIII, von Willlebrand factor, plasminogen, Alpha 2-macroglobulin, ferritin, hepcidin, cerruloplasmin, haptoglobin, orosomucoid, alpha 1-antitrypsin, and alpha-1 antichymotrypsin. Exemplary acute phase response proteins that are decreased in response to inflammation includes, e.g., albumin, transferrin, transthyretin, retinol-binding protein, antithrombin, transcortin. The acute phase-response modulator can be any agent that modulates the release of positive acute phase response proteins, described herein, into plasma, or can be any agent that modulates the release of negative acute phase response proteins described herein into plasma. Exemplary agents include, e.g., R-1-[6-[R-2-carboxy-pyrrolidin-1-yl]-6-oxo-hexanoyl]pyrrolidine-2-carboxylic acid. Exemplary agents are described in, e.g., U.S. application Ser. No. 11/471,018, and U.S. Pat. No. 7,659,299.

"Administering" an anti-aggregate agent or therapy encompasses providing a recommendation for said anti-aggregate agent or therapy to said subject, prescribing an anti-aggregate agent or therapy to said subject, and administering an anti-aggregate agent or therapy to said subject. Administration of an agent can be by any route in which the agent will contact the target cell or tissue in said subject. Exemplary routes of administration include oral administration, injection, inhalation, transdermal infusion, topical administration, or parenteral administration. Oral administration can be by ingestion of an oral dosage form, including, by way of example only, solid dosage forms such as, e.g., tablets, capsules, caplets, gelatin capsules, sustained release formulations, lozenges, thin films, lollipops, chewing gum, or liquid dosage forms such as, e.g., hydrophilic suspensions, emulsions, liquids, gels, syrups, slurries, solutions, elixirs, softgels, tinctures, hydrogels, or beverages comprising the agent. Exemplary routes of injection include is intraperitoneal, intravenous, intra-arterial, intraosseous, subcutaneous, intrathecal, or intramuscular injection. Exemplary routes of inhalation include, e.g., inhalation by a nebulizer, inhaler, vaporizer, face mask, or breathing machine. Exemplary routes of transdermal or topical administration include, e.g., contacting said subject with gels, water soluble jellies, creams, lotions, suspensions, foams, powders, slurries, ointments, oils, pastes, suppositories, solutions, sprays, emulsions, saline solutions, dimethylsulfoxide (DMSO)-based solutions comprising the therapeutic agent. Parenteral administration includes any route of administration other than via the gastrointestinal tract (any other route than oral or rectal administration), and encompasses non-intraperitoneal injection, inhalation, transdermal or topical administration, localized administration such as, e.g., administration of eye or ear drops, intracerebral injection, intracerebrovascular injection.

The method of determining if an anti-aggregate agent or therapy is efficacious can comprise measuring a change in the level of non-native TTR in said subject during said therapy. In some embodiments, measuring a change in the level of non-native TTR comprises measuring a level of non-native TTR in said subject at a plurality of time points during said therapy. In one embodiment, measuring a change in the level of non-native TTR comprises measuring a first level of non-native TTR at a first time point prior to initiating a therapy, measuring a second level of non-native TTR at a second time point after initiating said therapy, and comparing said first level and said second level. In another embodiment, the first and second time point can both occur after initiating a therapy. The second time point can be at any later time point than said first time point. In some embodiments, measuring a change comprises measuring a level of non-native TTR at multiple time points, e.g., 2, 3, 4, 5, 6, 7, 8, 9, 10, 15, 20, 25, or more than 25 time points. In some embodiments, the second time point is at least 12 hours later, 24, hours later (1 day later), 2 days later, 3, days later, 4 days later, 5 days later, 6 days later, 1 week later, 2 weeks later, 4 weeks later, 1 month later, 2 months later, 3 months later, 4 months later, 5 months later, 6 months later, 7 months later, 8 months later, 9 months later, 10 months later, 11 months later, 1 year later, or more than 1 year later than said first time point. In some embodiments, the multiple time points can be spaced apart by 12 hours, 24, hours (1 day), 2 days, 3, days, 4 days, 5 days, 6 days, 1 week, 2 weeks, 4 weeks, 1 month, 2 months, 3 months, 4 months, 5 months, 6 months, 7 months, 8 months, 9 months, 10 months, 11 months, 1 year, or more than 1 year. In some embodiments, a therapy is designated as efficacious in said subject if a level is decreased as compared to a level measured at a prior time point. In some embodiments, a therapy is designated as efficacious in said subject if said level is decreased by at about 5% or more, 10% or more, 15% or more, 20% or more, 25% or more, 30% or more, 35% or more, 40% or more, 45% or more, 50% or more, 55% or more, 60% or more, 65% or more, 70% or more, 75% or more, 80%, or more 85% or more, 90% or more, 95% or more, or 100% as compared to said prior time point. In one embodiment, a therapy is designated as efficacious in said subject if said level is decreased to a level as measured in a control subject or to an undetectable level. In some embodiments, the method further comprises alerting said subject or caregiver thereof that said therapy is efficacious. In some embodiments, a therapy is designated as not efficacious in said subject if said level has not decreased as compared to a level measured at a prior time point. In some embodiments, the method further comprises alerting said subject or caregiver thereof that said therapy is not efficacious.

In some embodiments, dosage of an anti-aggregate agent is adjusted based on a change in the level of non-native TTR in said subject during a course of administration of said agent. By way of example only, dosage of an anti-aggregate agent can be titrated to achieve a reduction of non-native TTR at a desired rate. By way of example only, if during a course of administration of an anti-aggregate agent, the level of non-native TTR decreases only slightly (e.g., by less than 10%) or decreases slowly over time (e.g., by less than 10% over more than a month), the dosage of said anti-aggregate agent can be increased. Alternatively, said anti-aggregate agent can be administered more frequently. By way of other example only, if during a course of administration of an anti-aggregate agent, a subject experiences a negative side effect of said administration, and the level of non-native TTR decreases rapidly (e.g., by over 50% in less than 1 week), dosage of said agent can be reduced in order to reduce negative side effects in said subject while still effecting a decrease in the level of non-native TTR in said subject, possibly at a slower rate. By way of other example, if during a course of administration of an anti-aggregate agent, the level of non-native TTR does not decrease in said subject, dosage of said agent may be increased to effect a decrease in the level of non-native TTR in said subject. In one embodiment, dosage of said anti-aggregate agent is increased if said detected level is increased by 20% or more as compared to a level measured at an earlier time point. Alternatively, a different anti-aggregate agent may be selected for administration in said subject. For example, administration of said first anti-aggregate agent may be terminated and administration of a different anti-aggregate agent initiated. For other example, administration of a second anti-aggregate agent may be initiated on top of administration of said first anti-aggregate agent (e.g., combination therapy).

In some embodiments, the antibodies of the present invention can be used to identify agents that reduce or increase a level of non-native TTR in a cell. Methods of identifying such agents can be useful for identifying new therapies for TTR-related diseases. In one embodiment, a method includes: contacting a cell that expresses or is capable of expressing TTR with a test compound; and detecting or measuring a level of non-native TTR in said cell or in a sample obtained from said cell. The contacting can take place in vitro (e.g., in a cell culture system), in vivo (e.g., by administration of a test compound to a subject), or ex vivo (e.g., by contacting a biological sample obtained from a subject with a test compound). Test compounds that cause a reduction in a level of non-native TTR, as compared to said cell before said contacting, or as compared to a control cell that is not contacted with said test compound, can be identified and/or selected as potential therapeutic agents. Therefore, in some embodiments, the therapy comprises administration of an agent that has been identified as a potential therapeutic agent using a method described herein.

In another aspect, the invention contemplates use of the antibodies of the present invention as a therapeutic agent. The antibody can form an immunocomplex with non-native TTR in a subject. The formation of the immunocomplex can, for example, inhibit the aggregation of non-native TTR (e.g., TTR monomers and/or oligomers) into fibrils and amyloid deposits. This inhibition can reduce amyloid burden in a subject. In some embodiments, the formation of the immunocomplex induces the proteolytic degradation of the complexed non-native TTR, e.g., the antibody is a catalytic antibody that selectively binds to and induces proteolytic degradation of non-native TTR. Catalytic antibodies and methods of producing the same are described herein. In another aspect, the invention provides an immunocomplex comprising a non-native TTR and an antibody of the present invention.

Kits

The invention further provides kits including one or more antibodies of the invention, including pharmaceutical formulations, packaged into suitable packaging material. In some embodiments, the kit comprises an antibody of the invention. In some embodiments, the kit comprises an antibody of the invention and instructions for use of the antibody to detect non-native forms of TTR in a biological sample obtained from said subject. In other embodiments, a kit includes a nucleic acid encoding an antibody of the invention. In other embodiments, a kit includes a cell that expresses an antibody of the invention.

In some embodiments, the kit includes a packaging material. As used herein, the term "packaging material" refers to a physical structure housing the components of the kit. The packaging material can maintain sterility of the kit components, and can be made of material commonly used for such purposes (e.g., paper, corrugated fiber, glass, plastic, foil, ampules, etc.).

In some embodiments, the kit comprises instructions for use of the antibody, e.g., instructions for practicing a method of the invention. By way of example only, the instructions may be a protocol for conducting a binding assay utilizing the antibody of the invention. By way of other example only, the instructions may be a protocol for expressing an invention antibody or a nucleic acid encoding an invention antibody in cells in vitro, in vivo, or ex vivo. In yet additional embodiments, the instructions may comprise instructions for treating a subject (e.g., a subject at risk for developing a symptom of an amyloid disease) by administering an anti-aggregate therapy if non-native TTR is detected in said subject utilizing an antibody of the invention. In some embodiments, the instructions may be a protocol for detecting the presence or measuring a level of non-native TTR in vivo, ex vivo, or in vitro. The instructions can include instructions for practicing any of the methods of the invention described herein.

The kit can also include a buffering agent, a preservative, or a protein/nucleic acid stabilizing agent. The kit can also include control samples of known non-native TTR concentrations which may be used to calculate a standard curve. In some embodiments, the kit includes a negative control sample, e.g., a sample that does not contain non-native TTR. In some embodiments, the kit includes a positive control sample, e.g., a sample containing known amounts of non-native TTR.

In some embodiments, the kit comprises a detectable label that is capable of forming a complex with an antibody of the invention. By way of example only, the detectable label can be a secondary antibody conjugated to a detectable moiety that is capable of binding to an antibody of the invention. The detectable moiety may be any detectable moiety known in the art or described herein. Exemplary detectable moieties include radioisotopes, fluorescent compounds, chemiluminescent compounds, colloidal metals, luminescent compounds, enzymes, and paramagnetic labels. Exemplary enzymes which may be used as detectable moieties include acetyltransferase, galactosidase, glucose oxidase, peroxidase, horseradish peroxidase (HRP), urease and alkaline phosphatase.

Exemplary fluorescent compounds include, e.g., fluorescein isothiocyanate, rhodamine, phycoerytherin, phycocyanin, allophycocyanin, o-phthaldehyde, fluorescamine, and commercially available fluorophores such as Alexa Fluor 350, Alexa Fluor 488, Alexa Fluor 532, Alexa Fluor 546, Alexa Fluor 568, Alexa Fluor 594, Alexa Fluor 647, DyLight dyes such as DyLight 488, DyLight 594, DyLight 647, and BODIPY dyes such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine and Texas Red, from Molecular Probes, Inc., Eugene, Oreg.), Exemplary luminescent compounds include, e.g., luminol, isoluminol, an aromatic acridinium ester, an imidazole, an acridinium salt and oxalate esters), bioluminescent compounds (e.g., luciferin, luciferase and aequorin.

In some embodiments, the kit comprises a solid support and an invention antibody, as well as instructions and/or reagents for immobilizing said antibody to said solid support. In other embodiments, the kit comprises a solid support with an invention antibody immobilized thereon. In some embodiments, the immobilized antibody or antibody to be immobilized onto the solid support is a TTR antibody that recognizes and binds both native and non-native TTR. In other embodiments the immobilized antibody or antibody to be immobilized is a TTR antibody that recognizes and selectively binds to non-native TTR as compared to native TTR. The solid support can be, e.g., a microtiter plate. In some embodiments, the kit further comprises an invention antibody that is not immobilized onto said solid support. In some embodiments, the antibody that is not immobilized onto said solid support is the same antibody that is immobilized on said solid support. In other embodiments, the antibody that is not immobilized onto said solid support is a different antibody that the antibody immobilized on said solid support. In preferred embodiments, the antibody that is not immobilized onto said solid support selectively binds to non-native TTR as compared to native TTR.

Computer Readable Medium

In one aspect, the invention provides a computer readable medium. In some embodiments, the computer readable medium comprises codes that, upon execution by one or more processors, implements a method of determining a likelihood of a subject to develop a symptom of a disease, the method comprising: (a) receiving measurement data regarding a detected level of non-native TTR in a subject or in a biological sample obtained from said subject, (b) comparing said measurement data against a set threshold level for designating said subject as having an increased likelihood of developing a symptom, and (c) designating said subject as having an increased risk of developing said disease if said detected level of non-native TTR exceeds said threshold level.

In another aspect, the invention provides a computer readable medium. In some embodiments, the computer readable medium comprises codes that, upon execution by one or more processors, implements a method of diagnosing a subject for a disease associated with TTR amyloidosis, the method comprising: (a) receiving measurement data regarding a detected level of non-native TTR in a subject or in a biological sample obtained from said subject, (b) comparing said measurement data against a set threshold level for designating said subject as having a disease associated with TTR amyloidosis, and (c) designating said subject as having a disease associated with TTR amyloidosis if said detected level of non-native TTR exceeds said threshold level.

In another embodiment, the computer readable medium comprises codes that, upon execution by one or more processors, implements a method of assessing a likelihood of a subject to develop a symptom of a disease, the method comprising: (a) receiving measurement data regarding a detected level of non-native TTR in a subject or in a biological sample obtained from said subject, (b) comparing said measurement data against a set threshold level for designating said subject as having an increased likelihood of developing a symptom, and (c) alerting a caregiver to commence treatment for said disease, wherein said treatment comprises administering an anti-aggregate agent to said subject.

In another embodiment, the computer readable medium comprises codes that, upon execution by one or more processors, implements a method of assessing efficacy of an anti-aggregate therapy applied to a subject, comprising: (a) receiving measurement data regarding a change in the detected level of non-native TTR in a subject or in a biological sample obtained from said subject during said therapy, (b) designating said therapy as efficacious if said change is a decrease in non-native TTR, and (c) alerting a caregiver of said designation.

Computer Systems

In another aspect, the invention provides computer systems for the early detection, diagnosis, or prognosis of a disease. In some embodiments, the invention provides computer systems for determining the efficacy of an anti-aggregate therapy applied to a subject in need thereof. In some embodiments, the computer system provides a report communicating said early detection, diagnosis, prognosis, or therapy efficacy for said disease. In some embodiments, one or more steps of the methods described herein for diagnosis, prognosis, predicting therapeutic efficacy are performed with the aid of a processor, e.g., a computer system executing instructions contained in a computer-readable medium. In some embodiments, the processor is associated with one or more controllers, calculation units, and/or other units of a computer system, or implanted in firmware. In some embodiments, one or more steps of the method are implemented in hardware. In some embodiments, one or more steps of the method are implemented in software. Software routines may be stored in any computer readable memory unit such as flash memory, RAM, ROM, magnetic disk, laser disk, or other storage medium as described herein or known in the art. Software may be communicated to a computing device by any known communication method including, for example, over a communication channel such as a telephone line, the internet, a wireless connection, or by a transportable medium, such as a computer readable disk, flash drive, etc. The one or more steps of the methods described herein may be implemented as various operations, tools, blocks, modules and techniques which, in turn, may be implemented in firmware, hardware, software, or any combination of firmware, hardware, and software. When implemented in hardware, some or all of the blocks, operations, techniques, etc. may be implemented in, for example, an application specific integrated circuit (ASIC), custom integrated circuit (IC), field programmable logic array (FPGA), or programmable logic array (PLA).

A computer system may be used for one or more steps, including, e.g., sample collection, sample processing, genotyping, receiving patient history or medical records, receiving and storing measurement data regarding a detected level of non-native TTR, comparing said measurement data against a set threshold level to determine a diagnosis, prognosis, or therapeutic efficacy, generating a report, and reporting results to a receiver.

A client-server and/or relational database architecture can be used in embodiments of the invention. In general, a client-server architecture is a network architecture in which each computer or process on the network is either a client or a server. Server computers can be powerful computers dedicated to managing disk drives (file servers), printers (print servers), or network traffic (network servers). Client computers can include PCs (personal computers) or workstations on which users run applications, as well as example output devices as disclosed herein. Client computers can rely on server computers for resources, such as files, devices, and even processing power. In some embodiments of the invention, the server computer handles all of the database functionality. The client computer can have software that handles front-end data management and receive data input from users.

In some embodiments there is provided a computer readable medium encoded with computer executable software that includes instructions for a computer to execute functions associated with a detected level of non-native TTR. Such computer readable medium may include any combination of such codes or computer executable software, depending upon the types of evaluations desired to be completed. The system can have code for calculating a weighted risk based on one or more levels of non-native TTR. The system can further comprise code for conducting genetic analysis based on mutation status of TTR in a subject. The system can also have code for one or more of the following: conducting, analyzing, organizing, or reporting the results, as described herein. The system may comprise code for comparing a detected level of non-native TTR to a threshold value, and assigning a fold-baseline risk based on whether or not the threshold value is exceeded. The system can also have code for correlating an anti-aggregate therapy, e.g., administration of an anti-aggregate agent to a change in the level of non-native TTR in a subject during said therapy. The code can additionally be configured to designate said therapy as efficacious if said change is a decrease in the level of non-native TTR during said therapy. Accordingly, the system can comprise code implementing methods described herein for adjusting treatment of an amyloid disease in a subject. The system can also have code for generating a report.

After performing a calculation, a processor can provide the output, such as from a calculation, back to, for example, the input device or storage unit, to another storage unit of the same or different computer system, or to an output device. Output from the processor can be displayed by a data display, e.g., a display screen (for example, a monitor or a screen on a digital device), a print-out, a data signal (for example, a packet), a graphical user interface (for example, a webpage), an alarm (for example, a flashing light or a sound), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In some embodiments, an output device is the same device as the input device. Example output devices include, but are not limited to, a telephone, a wireless telephone, a mobile phone, a PDA, a flash memory drive, a light source, a sound generator, a fax machine, a computer, a computer monitor, a printer, an iPod, and a webpage. The user station may be in communication with a printer or a display monitor to output the information processed by the server. Such displays, output devices, and user stations can be used to provide an alert to the subject or to a caregiver thereof.

Data relating to the present disclosure can be transmitted over a network or connections for reception and/or review by a receiver. The receiver can be but is not limited to the subject to whom the report pertains; or to a caregiver thereof, e.g., a health care provider, manager, other healthcare professional, or other caretaker; a person or entity that performed and/or ordered the genotyping analysis; a genetic counselor. The receiver can also be a local or remote system for storing such reports (e.g. servers or other systems of a "cloud computing" architecture). In one embodiment, a computer-readable medium includes a medium suitable for transmission of a result of an analysis of a biological sample, such as analysis of a level of non-native TTR. The medium can include a result regarding the level of non-native TTR in said subject, risk (such as fold-baseline risk) of developing a symptom of an amyloid disease, risk of having an amyloid disease, and/or an action plan or treatment recommendation for the subject, wherein such a result is derived using the methods described herein.

In some embodiments, the subject or another individual (e.g. a heath care provider, health care manager, other health professional, or other caretaker) is alerted if a subject is designated as being at risk for developing a symptom of a disease or risk of having a disease. In some embodiments, the method further comprises providing a recommendation for action based on an assessment of a subject's a symptom of a disease or risk of having a disease. A recommendation may form part of a report generated based on risk assessment, or may be made by a receiver on the basis of such report. A recommendation may be for further action on the part of the subject and/or for a third party, such as a heath care provider, health care manager, other health professional, or other caretaker. Recommendations may include, but are not limited to, prescription or administration of one or more therapeutic agents. In some embodiments, the therapeutic agent is prescribed, administered, or otherwise provided at a therapeutically effective dose.

EXAMPLES

Example 1: Generation of TTR Immunogens

Tetrameric and Monomeric TTR Expression and Purification

Tetrameric and monomeric TTR was generated as previously described (Babbes, et al, Biochemistry 2008. 47(26): 6969-6984). Briefly, all TTR variants were expressed in BL21(DE3) Epicurian Gold *Escherichia coli* cells (Stratagene, La Jolla, Calif.), transformed with the appropriate pMMHa expression vector containing the TTR and ampicillin resistance genes. *E. coli* cultures were grown, harvested, and lysed in the presence of protease inhibitors, and the cell lysates were centrifuged. All of the variants examined were expressed as soluble proteins and were therefore purified from cell supernatants. The supernatant was fractionated by ammonium sulfate precipitation; the 50-100% ammonium sulfate pellet was resuspended in a minimal volume of 25 mM Tris, 1 mM EDTA (pH 8.0) and was dialyzed in 10,000 MWCO dialysis tubing (Snakeskin from Pierce Biotechnology, Rockford, Ill.) against 4 L of 25 mM Tris, 1 mM EDTA (pH 8.0) overnight at 4° C. After dialysis, the sample was filtered through 0.22 µm filters and applied to a Source 15Q anion exchange column (Amersham Biosciences, Piscataway, N.J.), which had been equilibrated with 25 mM Tris, 1 mM EDTA, 50 mM NaCl (pH 8.0) and was run at 4° C. TTR was eluted with a linear gradient of 50-350 mM NaCl in 1.5 column volumes followed by a 350 mM NaCl wash for 1.5 column volumes. Fractions containing TTR (the major peak in all cases) were pooled, concentrated, and further purified on a Superdex 75 gel filtration column (Amersham Biosciences, Piscataway, N.J.) in 50 mM sodium phosphate, 100 mM KCl, 1 mM EDTA (pH 7.4) at 4° C., in order to remove any soluble TTR aggregates. The identity of each purified TTR variant was confirmed by its mass, determined by electrospray LC/MS on a HP Series 1100-MSD liquid chromatography/mass spectrometer (Agilent Technologies, Palo Alto, Calif.). Concentrations of TTR solutions are expressed in micromolar (µM) units and were determined spectrophotometrically, using an $\epsilon 280$ of $1.88 \times 10^4$ M-1 cm-1. A typical purification yields 60-100 mg of tetrameric TTR from 2 L of cell culture. All TTR solutions were stored at 4° C. and were used within a week of purification.

M-TTR was purified according to the above procedure, with slight modifications to the ammonium fractionation step: A 25-90% ammonium sulfate pellet was obtained, resuspended, and dialyzed in 3,500 MWCO Snakeskin dialysis tubing (Pierce Biotechnology, Rockford, Ill.). The typical yield is 40-60 mg of M-TTR from 2 L of cell culture; M-TTR thus obtained is >95% monomeric.

Peptide Immunogen Design & Synthesis

Synthetic polypeptide fragments of the human transthyretin proteins and the corresponding immunogenicity-enhancing conjugates were also generated as antigens for antibody production. Normally folded TTR adopts tetrameric conformation in solution. Pymol (Schrodinger, USA) was used to calculate and visualize solvent exposure of all amino acid side-chains of TTR based on the crystal structure of tetrameric TTR (PBD 2QGB). A polypeptide (ALA-ALA-LEU-LEU-SER-PRO-TYR-SER-TYR-SER-THR-THR-ALA-VAL (SEQ ID NO: 20)) corresponding to part of the G-strand and H-strand on TTR (amino acids 108-121)

was identified as solvent inaccessible when TTR is folded as a tetramer and only becomes exposed when the tetramer dissociates and/or misfolds, as in the cases of the various non-native intermediate conformations leading to TTR amyloidogenesis. The peptide was synthesized using standard solid phase chemistry. A Cysteine residue was added to the C-terminus of the peptide to facilitate conjugation.

Example 2. Preparation and Analysis of Non-Native TTR Forms 2.1 Preparation of Non-Native TTR Forms Non-native forms (including oligomeric forms) of TTR proteins were prepared using M-TTR or by incubating the normally folded tetrameric TTR proteins at 37° C. in 100 mM pH 4.3 acetate buffer at 0.2 mg/mL protein concentration for 16 hours (Bourgault, et al, Biochemistry 2011. 50(6): 1001-1015). Non-native forms of TTR were also prepared by incubating M-TTR (monomeric) or wild-type (tetrameric) TTR at 4° C., room temperature (e.g., about 20-30, 25-40° C.), or 37 C for over one day.

2.2 Cross-Linking of TTR

Glutaraldehyde cross-linking of TTR samples was achieved by addition of 1.6% v/v of glutaraldehyde solution (25% v/v solution in water) (Sigma-Aldrich, St. Louis, Mo.) at room temperature. The reaction was quenched by addition of 2.8% v/v of a 1.85 M NaBH4 solution (freshly prepared in 0.1 N NaOH) and incubation for 5 minutes. Samples were immediately mixed with SDS-PAGE sample buffer and separated on Novex 4-12% NuPAGE Bis-Tris precast gradient gels (Invitrogen, Carlsbad, Calif.). After electrophoresis, samples were transferred to 0.2 micron nitrocellulose and western blot performed using Western Breeze Chromogenic Immunodetection System as directed (Invitrogen) with anti-TTR antibody. For example, 1 microgram/ml rabbit polyclonal TTR antibody, MFD113, was used in FIG. 4B.

Example 3: Generation of Mouse Anti-TTR Monoclonal Antibodies 3.1 Mouse Immunization/Fusion and Antibody Purification Balb/c mice were immunized using recombinant monomeric human TTR immunogen, M-TTR, or M-TTR conjugated with KLH, and a long immunization protocol. The first immunization was given via intraperitoneal (ip) injection with one hundred micrograms (rig) of the antigen mixed in Complete Freund's Adjuvant (CFA) emulsion, followed by three ip injections two to three weeks apart with each delivering 50 μg of antigen mixed in Incomplete Freund's Adjuvant (IFA) emulsion. The serum was taken a week after fourth antigen injection to check the titer of antibodies by ELISA. Three mice with high response titer were euthanized, and the spleens were surgically removed for hybridoma cloning.

A single cell suspension of spleenocytes was prepared by forcing the spleen through a 100-micron stainless steel screen, then through a cell strainer, and wash twice in 30 ml RPMI. The spleenocytes were mixed with Sp2/0-Ag14 cells (Sigma, St. Louis, Mo.) or the likes in three to one ratio, and cell fusion was facilitated by adding 50% PEG-1500 and gentle stirring. The mixture of cells were precipitated by centrifugation, and gently washed with RPMI, followed by incubation in RPMI-1640 medium with 20% fetal calf serum (FCS) at 37 0 C for 30 minutes. The cells were suspended in RPMI-1640 containing 20% FCS, standard HAT (hypoxanthine, aminoptehn and thymidine), 25% spleen-conditioned medium, 2 mM glutamate and 100 ug/ml Pen-Strip, (Invitrogen; Calsbad, Calif.), dispensed in five 96-well plates and cultured in 37° C./5% CO 2 incubator for 8 to 20 days to allow HAT-resistant hybridoma clones established. The conditioned media from each hybridoma clone were subjected to ELISA screening.

Mouse monoclonal antibodies are produced either in hybridoma, ascites, or as recombinant proteins and purified with protein G following standard protocol.

3.2 mAb Sequencing

The monoclonal antibodies of the invention are immunoglobulins of subclass IgG1, kappa light chain.

Total RNA was extracted from frozen Hybridoma cells following the technical manual of TRIzol Plus RNA purification system (Life Technologies, USA). The total RNA was analyzed by agarose gel electrophoresis. Total RNA was reverse transcribed into cDNA using isotype-specific antisense primers or universal primers following the technical manual of SuperScript III first-strand synthesis system (Life Technologies, USA). The antibody fragment was amplified by Rapid amplification of 5' cDNA ends (RACE). RT-PCR was then performed to amplify the variable regions (heavy and light chains) of the antibody, which were then cloned into a standard cloning vector separately. Colony PCR screening was performed to identify clones with inserts of correct sizes. No fewer than ten independent positive colonies were sequenced for each antibody fragment. Ten clones with insertions of VH and VL genes were sequenced for the antibody fragments and the consensus sequences were derived for each hybridoma.

Example 4. Generation of Rabbit Anti-TTR Polyclonal Antibodies 4.1 H-Strand Polyclonal Antibody Polyclonal antibody was made by immunizing 2 NZW-SPF rabbits subcutaneously with 500 microgram each of KLH-conjugated H-strand peptide (ALLSPYSYSTTAV (SEQ ID NO: 16)) in complete Freund's adjuvant (CFA). Animals were boosted with 500 micrograms of the KLH-conjugated peptide in incomplete Freund's adjuvant 3 weeks later and then subsequently boosted two additional times at three-week intervals. Blood was drawn and serum was tested for antibody reactivity by ELISA. Terminal bleeds were taken ten weeks after the initial immunization and antibodies were purified using peptide affinity column. Antibody affinity and selectivity was confirmed by indirect ELISA using biotinylated H-strand peptide.

4.2 Total TTR Polyclonal Antibody

Polyclonal antibody was made as previously described (Purkey, et al. PNAS 2001 98:10 p. 5566-5571), briefly rabbits were injected with a 1:1 mixture of complete Freund's adjuvant and 1 mg/ml recombinant human TTR with an additional methionine at the N-terminus. After 5 weeks, the rabbits were given boosters of 1:1 incomplete Freund's adjuvant:TTR (1 mg/ml) every 2 weeks for 2 months. Subsequently, the boosters were given once a month. Fifty milliliters of serum was drawn from each rabbit 30 days after each booster injection, and the blood serum was isolated. Antibodies were isolated from rabbit serum by passage over a recombinant staphylococcal protein A column (Amersham Pharmacia Biotech). The column was washed with 5 column volumes of 50 mM sodium phosphate (pH 7.2), and the antibodies were eluted with 5 column volumes of 100 mM sodium citrate (pH 3.0). The elution fractions were returned to neutral pH with the addition of 1 ml of 1 M TrisHCl (pH 9.0) to each 5-ml fraction. The fractions were pooled and exchanged into 100 mM sodium bicarbonate, pH 8.2.

Example 5: ELISA Screening of Hybridomas 5.1 Direct ELISA

All Enzyme-linked immunoabsorbent assay (ELISA) were performed using Corning 96-well EIA/RIA high binding polystyrene plates (Thermo Fisher, Rochester, N.Y.). 2 µg/mL of M-TTR in 50 mM pH 9.6 sodium carbonate buffer was used to coat the plates and plates were then washed three times with TBST (1×TBS with containing 0.05% Tween-20) and then blocked with Superblock (Pierce, USA). Conditioned media from hybridoma clones from no dilution to 1:1,000 diluted in TBST were added to the wells and incubated at room temperature for one hour. The wells were washed three times with TBST. Horseradish peroxidase (HRP) conjugated goat-anti-mouse IgG or Fc antibody was added to detect the mAbs bound to the antigen. Excessive HRP was washed off by washing three times with TBST, 350 µl per well for each wash. TMB (3,3',5,5'-tetramethylbenzidine) solution was then added as substrate for HRP color development. The reaction was stopped and plates were scanned by a plate reader at 450 nm. Positive clones proceeded to additional ELISA screenings. Some of the clones are listed in Table 2.

5.2 Sandwich Assay

This section describes the sandwich ELISA assay format used during hybridoma screening. The same format is also applicable with purified antibodies in various combinations as outlined in Table 2.

Figure 4A:
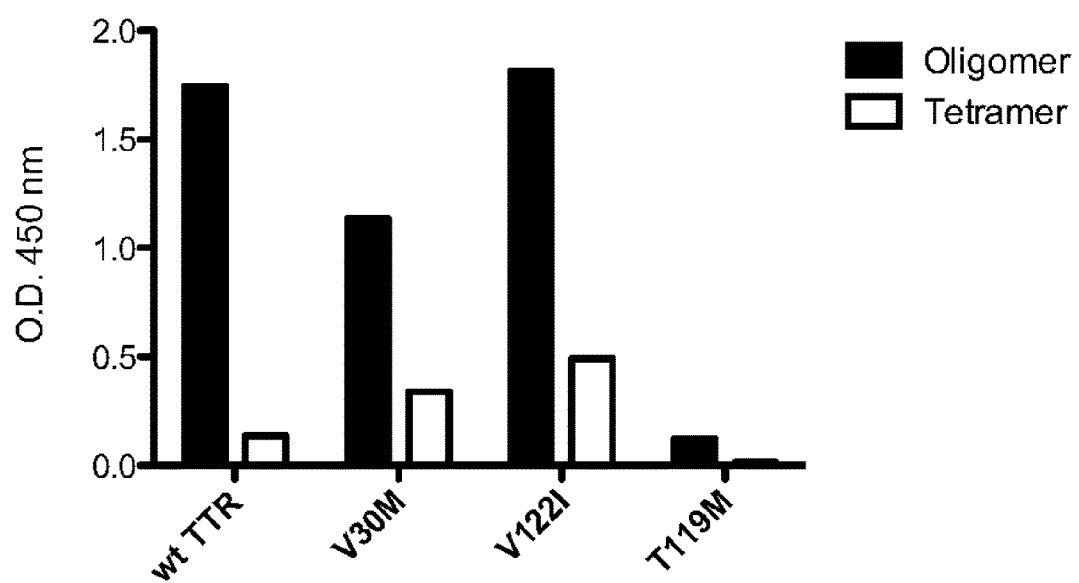
FIG. 4A illustrates results from a sandwich ELISA for the detection of non-native recombinant TTR conformations (dark bars) versus native tetrameric conformations* (white bars) using MFD114 and MFD102 as the capture and the detection antibodies, respectively.

Conditioned media from hybridoma clones were screened for their ability to bind selectively to misfolded monomeric and oligomeric forms of wild-type and mutant TTR proteins over normally folded tetrameric TTR proteins. In one embodiment, the ELISA plates were prepared by coating with rabbit anti-TTR polyclonal antibody MFD113, which was generated by immunizing rabbits with wild-type TTR as described above. Plates were blocked with Superblock (Pierce, USA) before various concentrations of M-TTR, oligomeric forms of wild-type and mutant TTR proteins, or normally folded tetrameric TTR proteins were added and incubated at room temperature for one hour. The wells were washed three times with TBST. Fifty microliters of each hybridoma clone supernatant was added to the wells and incubated at room temperature for one hour. The wells were washed three times with TBST. HRP conjugated goat-anti-mouse IgG or Fc antibody and TMB were then used for detection following the same protocol as in the indirect ELISA. FIG. 4A illustrates an example of MFD102 selectively detect non-native (including oligomeric) forms of TTR over tetrameric TTR in a sandwich ELISA assay.

In another embodiment, the capturing and detection antibodies were from the same species while the detection antibody was biotinylated. In this case, a HRP-conjugated Streptavidin would then be added to the ELISA samples after incubation with the detection antibody and subsequent wash steps. After washing off unbound Streptavidin, TMB substrate was added to enable the measurement.

Table 2, herein, listed some examples of the capture/detection antibody combinations used in this invention for detection of non-native TTR levels. The level of non-native TTR proteins correlates with the signals detected at 450 nm.

In one embodiment, a total TTR antibody was used as the capture antibody, while a non-native TTR specific antibody generated in a different species (mouse or rabbit) was used as the detection antibody.

In another embodiment, a non-native TTR specific antibody was used as the capture antibody, while a total TTR antibody generated in a different species was used as the detection antibody.

In another embodiment, a non-native TTR specific antibody was used as the capture antibody, while another non-native TTR specific antibody targeting a different epitope generated in a different species was used as the detection antibody.

In another embodiment, the capture antibody and the detection antibody were generated in the same species. The detection antibody was biotinylated.

In another embodiment, the capture antibody and the detection antibody were of the same antibody. The detection antibody was biotinylated.

5.3 Competition Assay

Competition assay was also employed to assess the binding selectivity of the hybridoma supernatants toward non-native (including monomeric and oligomeric) forms of TTR relative to normally folded tetrameric forms of wild-type and mutant TTR proteins. Corning 96-well high binding EIA/RIA plates were coated with 2 µg/mL of M-TTR in 50 mM pH 9.6 sodium carbonate/bicarbonate buffer and blocked with Superblock (Pierce, USA). Fifty to one hundred microliters of each hybridoma supernatant were spiked with 50 µg/mL of various forms of TTR proteins or bovine serum albumin (BSA, as a negative control). The mixtures were incubated at room temperature for one hour before being added to the coated plates, and incubated at room temperature for another hour. The wells were washed three times with TBST. HRP conjugated goat-anti-mouse IgG or Fc antibody and TMB was then used for detection following the same protocol as in the indirect ELISA. Binding to immobilized M-TTRA by a number of the hybridoma clones, including MFD102 and MFD108 (deposited with the American Type Culture Collection having the ATCC Patent Deposit Designation PTA-120816), can only be competed off by non-native forms of TTR but not tetrameric TTR, indicating favorable selectivity.

Example 6. Epitope Mapping

In order to identify the linear continuous sequences for which the anti-TTR antibodies recognize, an overlapping peptide library was designed and synthesized (Table 3).

TABLE 3 peptides used for linear epitope mapping.

| Peptide ID | Sequence | SEQ ID NO: |
|---|---|---|
| 1 | GPTGTGESKCPLM | 21 |
| 2 | TGESKCPLMVKVL | 22 |
| 3 | KCPLMVKVLDAVR | 23 |
| 4 | MVKVLDAVRGSPA | 24 |
| 5 | LDAVRGSPAINVA | 25 |
| 6 | RGSPAINVAVHVF | 26 |
| 7 | AINVAVHVFRKAA | 27 |
| 8 | AVHVFRKAADDTW | 28 |
| 9 | FRKAADDTWEPFA | 29 |
| 10 | ADDTWEPFASGKT | 14 |
| 11 | WEPFASGKTSESG | 30 |
| 12 | ASGKTSESGELHG | 31 |
| 13 | TSESGELHGLTTE | 15 |
| 14 | GELHGLTTEEEFV | 32 |
| 15 | GLTTEEEFVEGIY | 33 |
| 16 | EEEFVEGIYKVEI | 34 |
| 17 | VEGIYKVEIDTKS | 35 |
| 18 | YKVEIDTKSYWKA | 36 |

TABLE 3-continued peptides used for linear epitope mapping.

| Peptide ID | Sequence | SEQ ID NO: |
|---|---|---|
| 19 | IDTKSYWKALGIS | 37 |
| 20 | SYWKALGISPFHE | 38 |
| 21 | ALGISPFHEHAEV | 39 |
| 22 | SPFHEHAEVVFTA | 40 |
| 23 | EHAEVVFTANDSG | 41 |
| 24 | VVFTANDSGPRRY | 42 |
| 25 | ANDSGPRRYTIAA | 43 |
| 26 | GPRRYTIAALLSP | 44 |
| 27 | YTIAALLSPYSYS | 45 |
| 28 | ALLSPYSYSTTAV | 16 |
| 29 | PYSYSTTAVVTNP | 46 |
| 30 | STTAVVTNPKE | 47 |
| 31 | VVTNPKE | 48 |

Polypeptides of 13 amino acids in length and 4 amino acids overlap spanning the entire wild-type TTR sequence were synthesized using standard solid phase chemistry and biotinylated. These peptides were purified to >75% purity and solubilized in double-distilled water or dimethyl sulfoxide (DMSO).

ELISA assay was then utilized to identify the corresponding epitope(s) for each antibody. 5 µg/mL of NeutrAvidin (Pierce, USA) in 50 mM pH 9.6 sodium carbonate/bicarbonate buffer was used to coat 96-well Corning high-binding EIA/RIA plates. The plates were washed three times with TBST buffer and blocked with Superblock (Pierce, USA). Fifty to one hundred microliters of the biotinylated peptides were diluted with PBS to 2 µg/mL and added to each well and incubated at room temperature for one hour. The plates were then washed again with TBST and hybridoma supernatant diluted with PBS/0.2% BSA or purified antibody (2 µg/mL) was added to the plates. After one hour room temperature incubation and washing steps, HRP-conjugated secondary antibody was applied. Goat-anti-mouse IgG or Fc HRP conjugates were used in the case of mouse monoclonal antibodies while goat-anti-rabbit IgG HRP conjugate antibody was used for rabbit polyclonal detection. TMB was used as the HRP substrate for the detections.

Figure 3:
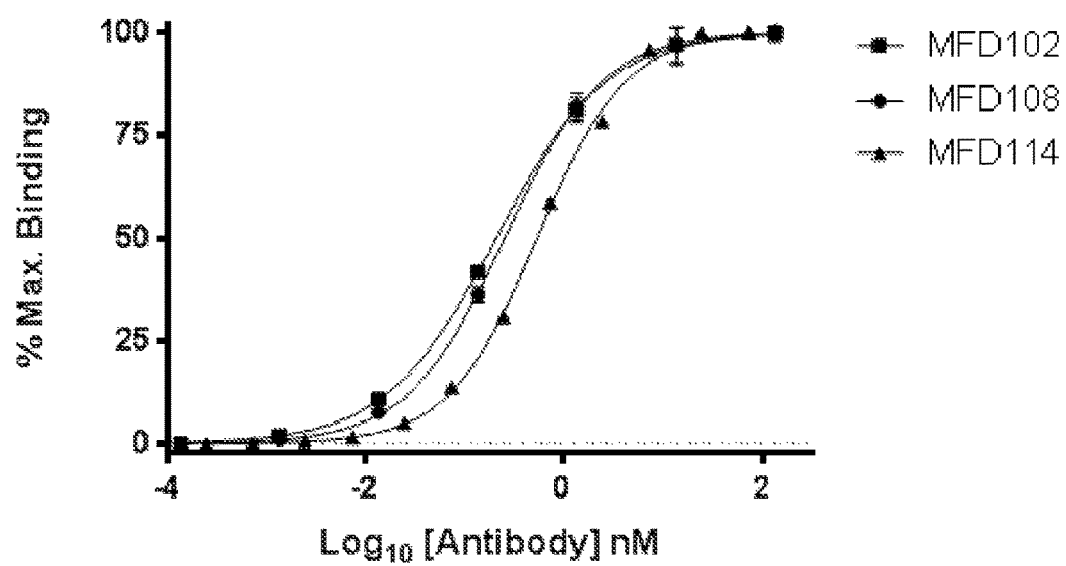
FIG. 3 illustrates the ELISA binding affinity of the antibodies to peptide TTR antigens: a) Mouse monoclonal antibody MFD102 binding to peptide 10 (ADDTWEPFAS-GKT (SEQ ID NO: 14); square); b) Mouse monoclonal antibody MFD108 binding to peptide 13 (TSESGELH-GLTTE (SEQ ID NO: 15); circle); c) Rabbit polyclonal antibody MFD114 binding to peptide 28 (ALLSPYSYST-TAV (SEQ ID NO: 16); triangle).

Three unique epitopes were identified for the antibodies that selectively recognize non-native forms of TTR (Table 1, herein). FIG. 3 illustrates the ELISA binding affinity of the antibodies to the respective peptide epitopes (peptide ADDTWEPFASGKT (SEQ ID NO: 14) for MFD102, peptide TSESGELHGLTTE (SEQ ID NO: 15) for MFD108, and peptide ALLSPYSYSTTAV (SEQ ID NO: 16) for MFD114. For example, mouse monoclonal antibody MFD102 recognizes peptide sequence ADDTWEPFASGKT (SEQ ID NO: 14), the underlined amino acids are unique to this peptide and do not exist in the neighboring peptides used for epitope mapping in this invention. The second unique non-native epitope corresponds to peptide sequence TSESGELHGLTTE (SEQ ID NO: 15), which is exemplified by mouse monoclonal antibody MFD108. These two epitopes reside on C-strand and D-strand in the TTR structure, respectively. Although C- and D-strands are located on the surface of the tetrameric TTR based on its crystal structure, the binding behavior of MFD102 and MFD108 suggests that the specific linear epitopes as identified in this invention represent different structural epitopes as compared to the native TTR structure. Interestingly, many deleterious TTR mutations reside around this region, such as L55P TTR (Lashuel, et al. Biochemistry. 1999 Oct. 12; 38(41):13560-73). It is likely that tetramer dissociation and oligomerization cause subtle unwinding and conformational changes around this region, rendering these linear structural epitopes accessible to antibodies such as MFD102 and MFD108. The third unique epitope by design is ALLSPYSYSTTAV (SEQ ID NO: 16), which is recognized by the rabbit polyclonal antibody MFD114. MFD114 also recognized neighboring peptides containing overlapping amino acids to peptide ALLSPYSYSTTAV (SEQ ID NO: 16), as would be expected for a polyclonal antibody.

In addition, the rabbit anti-total TTR antibody, MFD113, recognizes multiple linear epitopes, including but not limited to RGSPAINVAVHVF (SEQ ID NO: 26), ASGKTSES-GELHGLTTEEEFV (SEQ ID NO: 49), GPRRYTIAALLSP (SEQ ID NO: 44), and STTAVVTNPKE (SEQ ID NO: 47).

Although the mouse monoclonal antibody MFD112 was shown to be able to bind to multiple forms of TTR with similarly high binding affinity (FIG. 3) and is therefore considered a total TTR antibody, it does not appear to recognize any of the linear epitopes on TTR.

Example 7. Binding Affinity Determination

The physical binding affinity of the anti-TTR antibodies were measured by ELISA. In one embodiment, NeutrAvidin was used to capture 2 µg/mL of biotinylated peptide corresponding to the linear binding epitope of the antibody of interest, which was then serially diluted in PBS+0.2% BSA and added into the plates as the detection antibody. HRP-conjugated secondary antibodies were then employed with TMB used as the enzyme substrate and stopped with acidic solution. In the end, the absorbance at 450 nm was plotted as a function of antibody concentration and fitted to a non-linear regression to determine the binding affinity of each antibody (FIG. 3). All three antibodies assayed exhibited sub-nanomolar binding affinity (KD) toward their corresponding peptide epitopes.

To determine the ability of the antibodies to detect non-native and/or native forms of mutant TTR, recombinant TTR harboring various mutations (V30M, V122I, and T119M), as well as recombinant wild-type (WT) TTR were incubated under either neutral (pH 7) or acidic (pH 4.3) conditions as described in Example 2.1 to induce formation of non-native species. T119M TTR was used as a negative control, as the T119M substitution acts to stabilize the native (e.g., tetrameric) form of TTR even under oligomerization conditions as described herein. Samples were subjected to a sandwich ELISA assay as described herein (see, e.g., Section 5.2). The capture and detection antibodies were selected, e.g., according to Table 2. FIG. 4A depicts results of the sandwich assay, demonstrating selective detection of non-native wild-type and various mutant forms of TTR as compared to native wild-type and mutant forms of TTR.

Figure 4B:
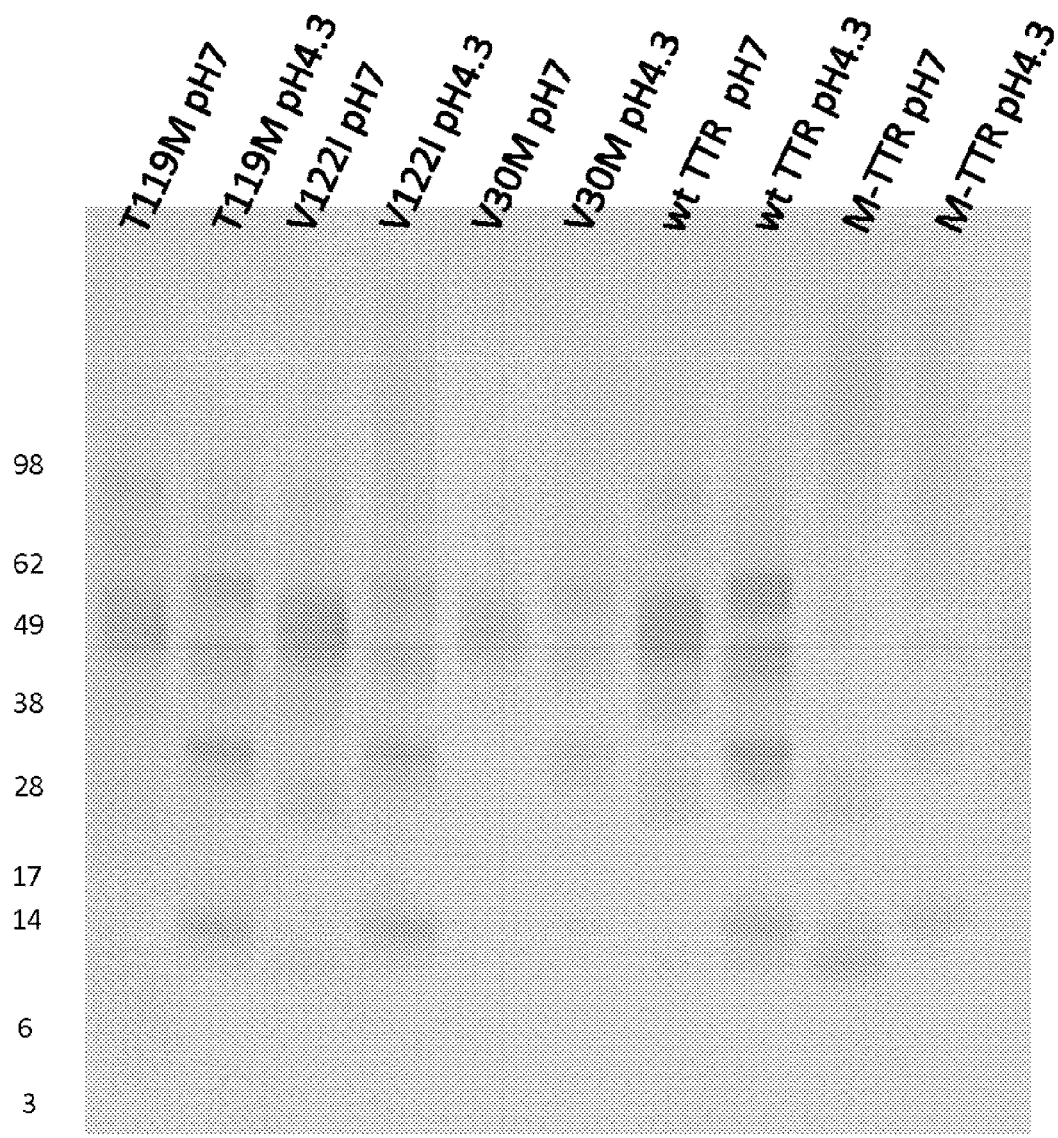
FIG. 4B illustrates a western blot of TTR variants incubated under either neutral (pH 7) or acidic (pH 4.3) conditions to induce formation of non-native species (instability and oligomer development). Proteins were crosslinked with glutaraldehyde and separated by SDS PAGE, transferred to nitrocellulose and detected with polyclonal anti-TTR antibody (MFD113).

To determine the binding affinity of the total TTR antibody MFD113, mutant TTR variants and WT TTR were incubated under neutral (pH 7) or acidic (pH 4.3) conditions as described in Section 2.1 to induce formation of non-native TTR species. Proteins were cross-linked with glutaraldehyde and separated by SDS-PAGE, then transferred to nitrocellulose and detected with MFD113 (FIG. 4B).

Figure 5:
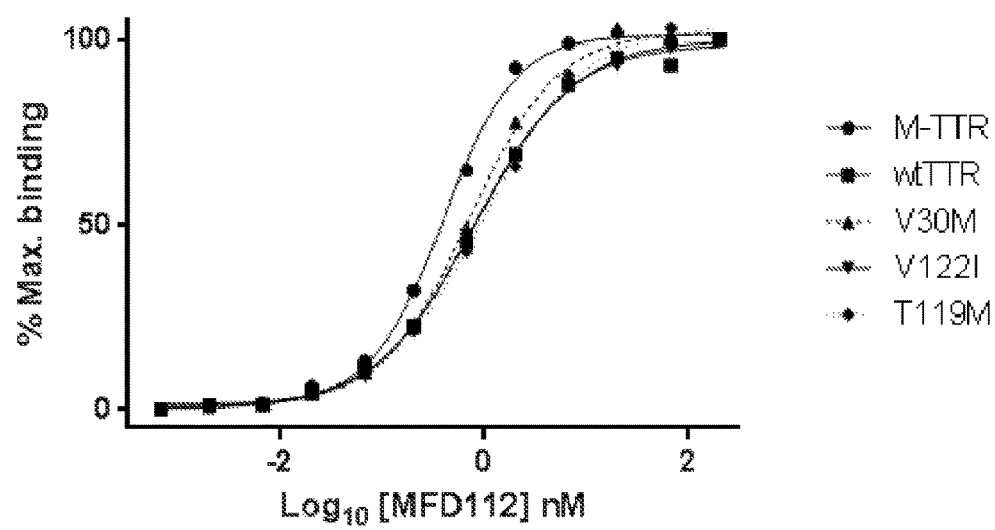
FIG. 5 illustrates the binding affinity of mouse monoclonal antibody MFD112 (recognizes total TTR) against wild-type and variants of tetrameric TTR, as well as monoclonal TTR (M-TTR), as ascertained by a Sandwich ELISA.

In another embodiment, a sandwich ELISA format was employed using the anti-total TTR antibodies MFD113 (rabbit polyclonal) and MFD112 (mouse monoclonal) as the capture and detection antibodies, respectively. A dilution series of MFD112 was used to detect M-TTR, wild-type and mutant tetrameric TTR proteins captured by MFD113-coated ELISA plate. Based on the non-linear regression data fitting, MFD112 exhibited sub-nanomolar binding affinity towards all TTR variants tested (FIG. 5).

Example 8. Identification of FAP Patient Plasma by Sandwich ELISA

Plasma samples from drug-naïve symptomatic V30M TTR Familial Amyloid Polyneuropathy (FAP) patients and age-matched controls were drawn by venipuncture into BD Vacutainer Cell Preparation Tubes (CPT) containing sodium citrate/Ficoll (Becton Dickinson #362782). Tubes were stored upright at room temperature for 30-45 minutes, mixed by inversion and then centrifuged for 20 minutes at 1500 RCF at room temperature. Plasma was carefully removed to avoid disturbing the mononuclear cell and platelet layer. Plasma was flash frozen and stored at −80° C. In a blinded fashion, plasma samples were analyzed by sandwich ELISA.

In one embodiment, the ELISA plates were prepared by coating with a TTR capture antibody, selected from Table 2, overnight at 4° C. in sodium carbonate/bicarbonate buffer, pH 9.6. Plates were blocked with Superblock (Pierce) for 1 hour at room temperature followed by incubation with plasma samples at 1/10-1:200 dilution in PBS+0.2% BSA (Sigma, Fraction V) for 2 hours at room temperature. The wells were then washed three times with TBST followed by a 1 hour incubation at room temperature with a 0.5 microgram/ml anti-non-native TTR antibody (e.g., detection antibody) selected from Table 2(diluted in PBS+0.2% BSA). Wells were then washed 3× with TBST followed by incubation for 30 minutes at room temperature with rabbit anti mouse IgG-HRP conjugate (Pierce, 1:10,000 dilution in PBS+0.2% BSA). After washing 3× with TBST, signal was detected with TMB (Pierce) with acid stop and absorbance measured at 450 nm.

Figure 6A:
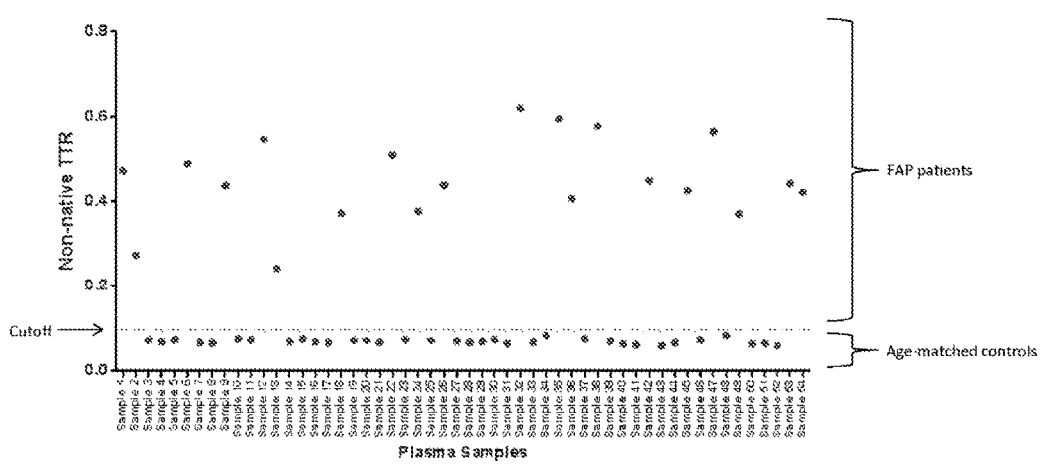
FIG. 6A illustrates results from a sandwich ELISA for the differentiation of plasma samples from drug-naïve, symptomatic familial amyloid polyneuropathy (FAP) patients and age-matched controls.

Background absorbance level and corresponding plate cutpoint were determined and samples with absorbance above the cutpoint were defined as positive for non-native TTR and classified as FAP carriers. By this method 20 out of 54 plasma samples were experimentally classified as FAP patients with the remaining 34 plasma samples classified as age-matched controls. Unblinding of the samples independently confirmed correct identification of 20/20 FAP patient and 34/34 age-matched control plasma samples (FIG. 6A).

In other embodiments, different combinations of capture/detection antibodies as listed in Table 2 were used to identify symptomatic patients from age-matched controls.

Example 9. Identification of FAP Carrier Plasma by Sandwich ELISA

Plasma samples from asymptomatic V30M TTR FAP patients and age-matched controls were drawn by venipuncture into BD Vacutainer Cell Preparation Tubes (CPT) containing sodium citrate/Ficoll (Becton Dickinson #362782). Tubes were stored upright at room temperature for 30-45 minutes, mix by inversion and then centrifuged for 20 minutes at 1500 RCF at room temperature. Plasma was carefully removed to avoid disturbing the mononuclear cell and platelet layer. Plasma was flash frozen and stored at −80° C. In a blinded fashion, plasma samples were analyzed by sandwich ELISA.

In one embodiment, the ELISA plates were prepared by coating with a TTR capture antibody, selected from Table 2, overnight at 4° C. in sodium carbonate/bicarbonate buffer, pH 9.6. Plates were blocked with Superblock (Pierce) for 1 hour at room temperature followed by incubation with plasma samples at 1/10-1:200 dilution in PBS+0.2% BSA (Sigma, Fraction V) for 2 hours at room temperature. The wells were then washed three times with TBST followed by a 1 hour incubation at room temperature with a 0.5 microgram/ml anti-non-native TTR antibody (e.g., detection antibody) selected from Table 2 (diluted in PBS+0.2% BSA). Wells were then washed 3× with TBST followed by incubation for 30 minutes at room temperature with rabbit anti mouse IgG-HRP conjugate (Pierce, 1:10,000 dilution in PBS+0.2% BSA). After washing 3× with TBST, signal was detected with TMB (Pierce) with acid stop and absorbance measured at 450 nm.

Background absorbance level and corresponding plate cutpoint were determined and samples with absorbance above the cutpoint were defined as positive for non-native TTR and classified as FAP carriers.

Figure 6B:
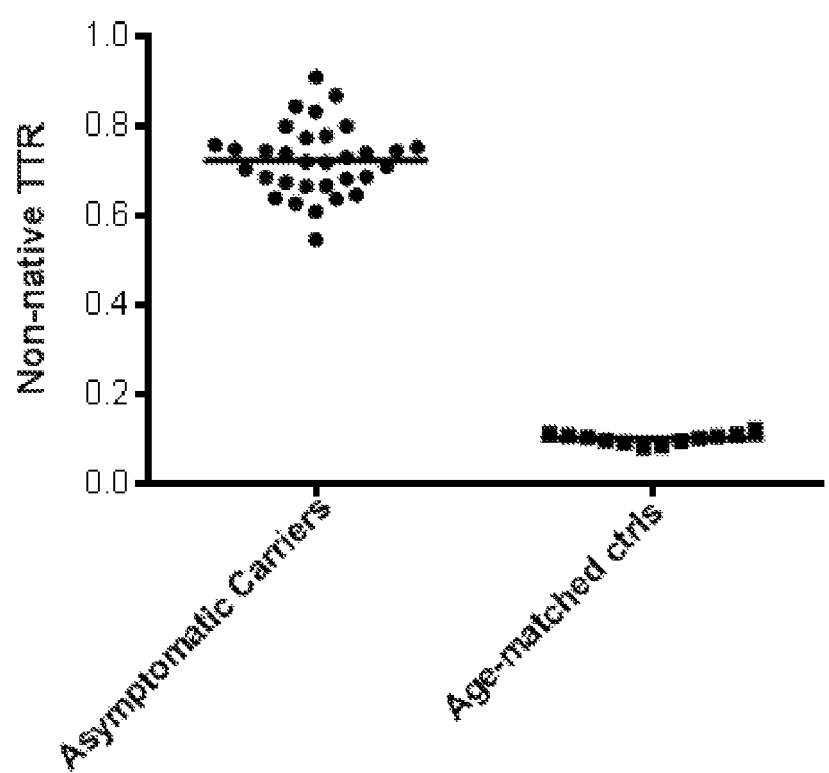
FIG. 6B illustrates results from a sandwich ELISA for the differentiation of plasma samples from asymptomatic familial amyloid polyneuropathy (FAP) carriers and age-matched controls.

By this method, 34 drug-naïve FAP carriers showed elevated level of non-native TTR proteins, clearly differentiated from the 34 age-matched controls where the non-native TTR signal is at background level (FIG. 6B).

In other embodiments, different combinations of capture/detection antibodies as listed in Table 2 were used to identify asymptomatic carriers from age-matched controls.

Example 10. Identification of Tafamidis Treated Patient Plasma by Sandwich ELISA Plasma samples from drug-naïve and tafamidis (a small molecule kinetic stabilizer of TTR) treated symptomatic V30M TTR FAP patients, and age-matched controls were drawn by venipuncture into BD Vacutainer Cell Preparation Tubes (CPT) containing sodium citrate/Ficoll (Becton Dickinson #362782). Tubes were stored upright at room temperature for 30-45 minutes, mix by inversion and then centrifuged for 20 minutes at 1500 RCF at room temperature. Plasma was carefully removed to avoid disturbing the mononuclear cell and platelet layer. Plasma was flash frozen and stored at −80° C. In a blinded fashion, plasma samples were analyzed by sandwich ELISA.

In one embodiment, the ELISA plates were prepared by coating with a TTR capture antibody, selected from Table 2, overnight at 4° C. in sodium carbonate/bicarbonate buffer, pH 9.6. Plates were blocked with Superblock (Pierce) for 1 hour at room temperature followed by incubation with plasma samples at 1/10-1:200 dilution in PBS+0.2% BSA (Sigma, Fraction V) for 2 hours at room temperature. The wells were then washed three times with TBST followed by a 1 hour incubation at room temperature with a 0.5 microgram/ml anti-non-native TTR antibody (e.g., detection antibody) selected from Table 2 (diluted in PBS+0.2% BSA). Wells were then washed 3× with TBST followed by incubation for 30 minutes at room temperature with rabbit anti mouse IgG-HRP conjugate (Pierce, 1:10,000 dilution in PBS+0.2% BSA). After washing 3× with TBST, signal was detected with TMB (Pierce) with acid stop and absorbance measured at 450 nm.

Figure 7:
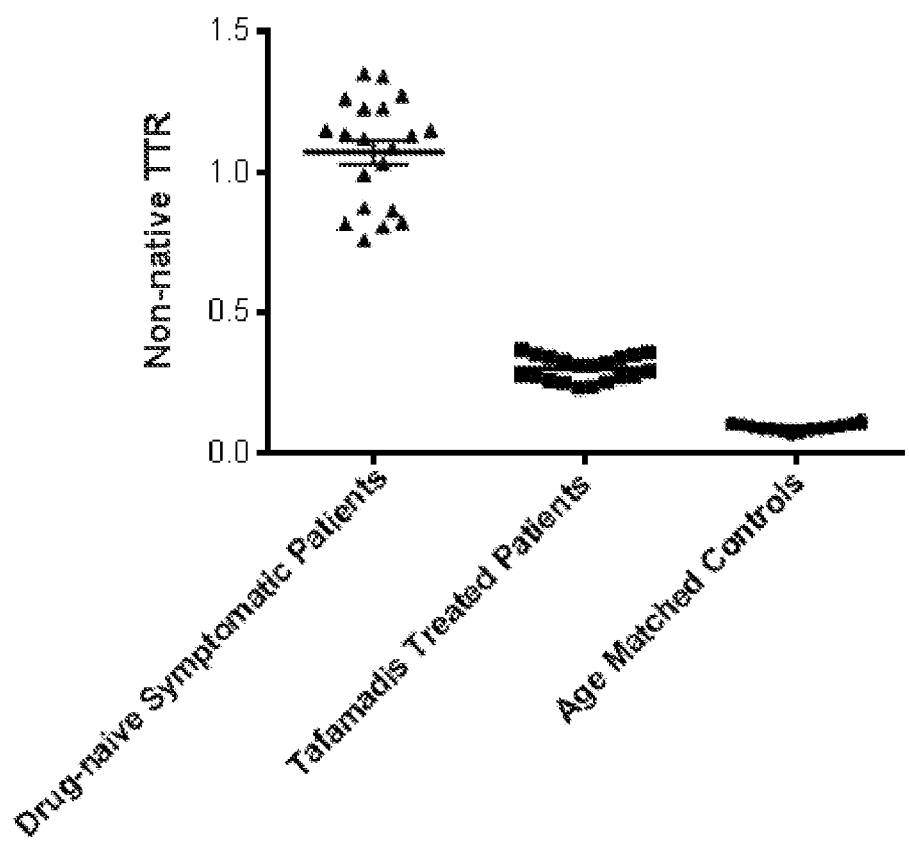
FIG. 7 illustrates results from a sandwich ELISA for the detection of non-native TTR conformations in the plasma of drug-naïve symptomatic FAP patients (N=20), tafamidis-treated FAP patients (N=20) and age-matched controls (N=34).

FIG. 7 depicts results from the sandwich ELISA for the detection of non-native TTR in plasma samples from drug-naïve symptomatic FAP patients (N=20), tafamidis-treated FAP patients (N=20) and age-matched controls (N=34). As shown in FIG. 7, serum from tafamidis treated FAP patients has significantly lower non-native TTR signal than that of treatment naïve symptomatic FAP patients, an indication of pharmacodynamics stabilization of TTR structure by tafamidis as a kinetic stabilizer.

In other embodiments, different combinations of capture/detection antibodies as listed in Table 2 were used to differentiate FAP patients before and after tafamidis treatment.

Figure 8:
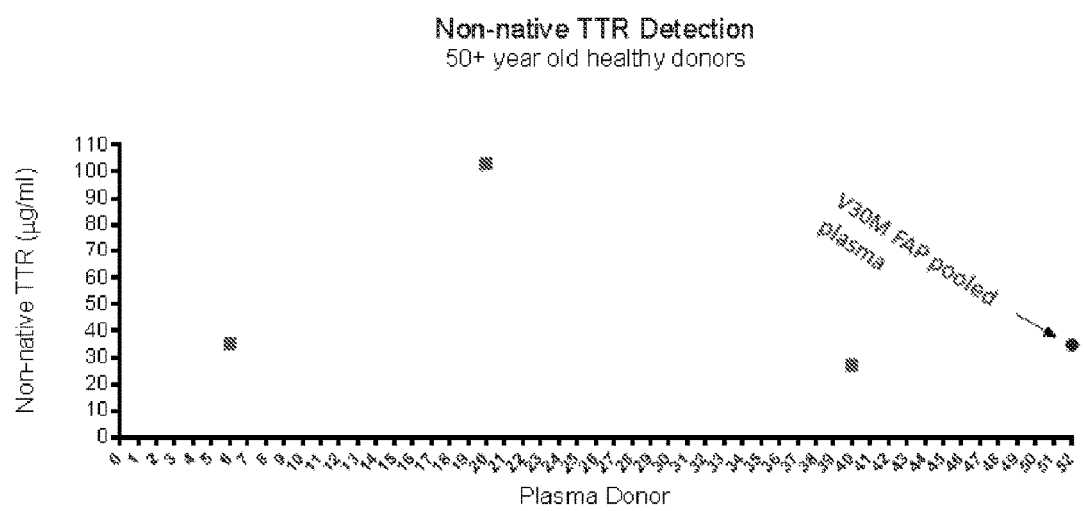
FIG. 8 depicts detection of non-native TTR in plasma from 50 year+healthy blood donors.

Example 11: Identification of Individuals at Risk for Developing TTR Amyloidosis in Plasma Samples from Otherwise Healthy Blood Donors There is no current method for early diagnosis of familial amyloid polyneuropathy (FAP), familial amyloid cardiomyopathy (FAC) or senile systemic amyloidosis (SSA). FIG. 8 depicts results from a sandwich ELISA assay performed as described herein for the detection of non-native TTR in plasma samples from fifty apparently healthy donors aged 50 years and older. Three out of the fifty samples are positive for non-native TTR. It is hypothesized that donors exhibiting a positive signal using the assay are considered to be at increased risk of developing TTR amyloidosis or are carriers of such diseases.

Figure 9:
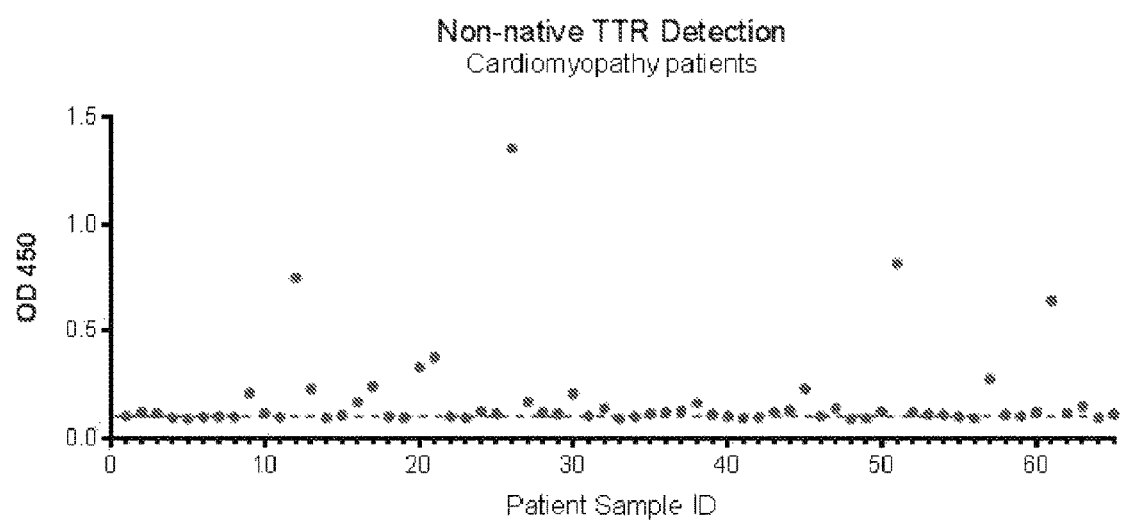
FIG. 9 depicts detection of non-native TTR in sera of symptomatic cardiomyopathy patients.

FIG. 9 depicts results from another sandwich ELISA assay performed as described herein for the detection of non-native TTR in 65 symptomatic cardiomyopathy patients. Several patients exhibited detectable levels of non-native F1R. Such detection can be used to support a diagnosis of FAC over a non-TTR related cardiomyopathy.

Example 12: Further Characterization of Exemplary Non-Native TTR Selective Antibodies To further characterize non-native TTR selective antibodies MFD108 and MFD114, recombinant monomeric TTR (M-TTR) was incubated under acidic conditions (pH 4.3 for 24 hours at 37° C.) to induce formation of non-native TTR species. Recombinant wild-type (WT) TTR was used as the native TTR control sample. 200 ng samples were subjected to SDS-PAGE denaturing (Novex NuPAGE Bis-Tris, Invitrogen) or native PAGE (Novex NativePAGE, Invitrogen) conditions. For denaturing conditions, samples were prepared in NuPAGE reducing (DTT) LDS buffer and denatured by heating at 70° C. for 10 minutes. Denatured samples were run on a Novex NuPAGE 4-12% Bis-Tris gel. Following electrophoresis, gels were either stained with colloidal coomassie or transferred to nitrocellulose for western blotting. For native PAGE conditions, samples were prepared in NativePAGE sample buffer (non-denaturing, without detergent). Non-denatured samples were separated on a Novex NativePAGE 4-12% Bis-Tris gel. Following electrophoresis, gels were transferred to a PVDF membrane. Blots were probed with either MFD108 or MFD114 antibody (0.5 mg/ml), followed by detection using an AP-conjugated secondary antibody and visualization by BCIP/NBT.

Figure 10:
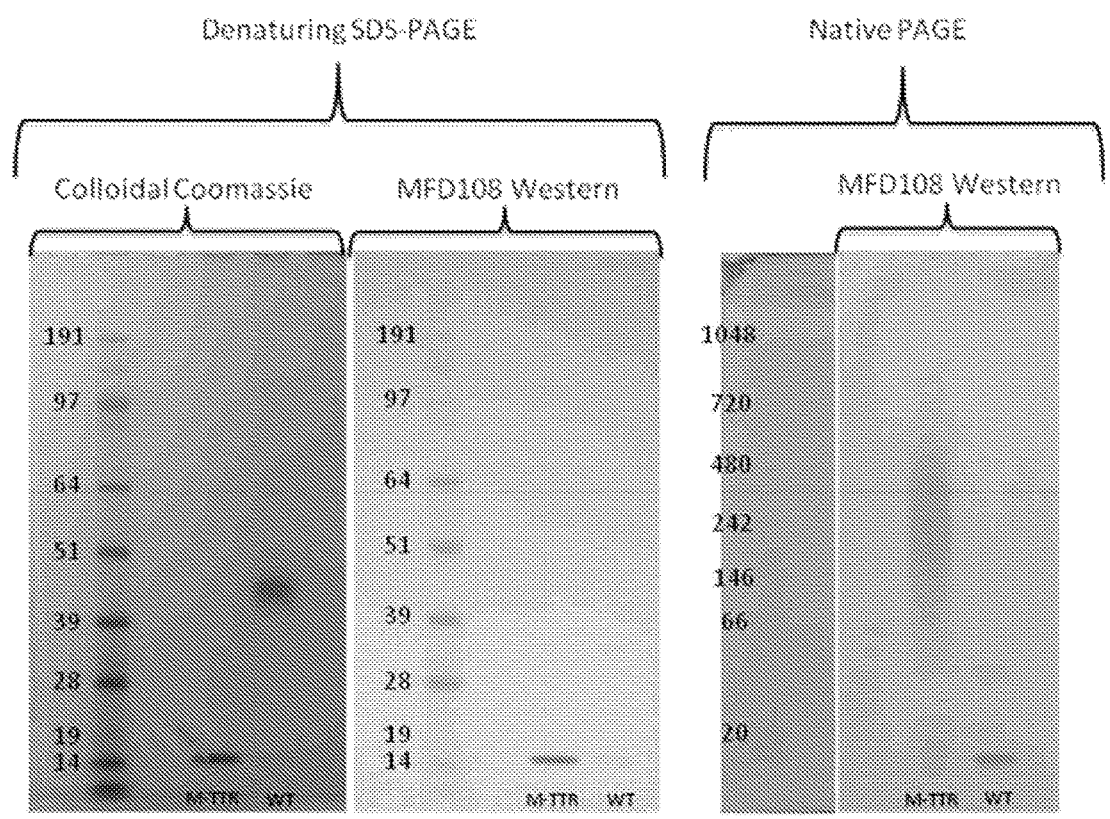
FIG. 10 depicts characterization of the non-native TTR using antibody MFD108.

FIG. 10 depicts the Colloidal Coomassie staining of non-native M-TTR and native WT TTR and corresponding western blot using the MFD108 antibody, under denaturing and native PAGE conditions, respectively. The Coomassie gel demonstrates that M-TTR after denaturation is mainly monomeric, and that WT-TTR is resistant to denaturation and mainly tetrameric. The corresponding MFD108 western blot demonstrates that MFD108 selectively recognizes monomeric TTR over tetrameric TTR. The native PAGE gel exhibits a high-molecular weight smear in the M-TTR lane, indicating that under non-denaturing PAGE conditions that oligomerized TTR are maintained and that MFD108 recognizes both oligomeric TTR and monomeric TTR (~14 kD band in the WT lane), but poorly recognizes tetrameric TTR.

Figure 11:
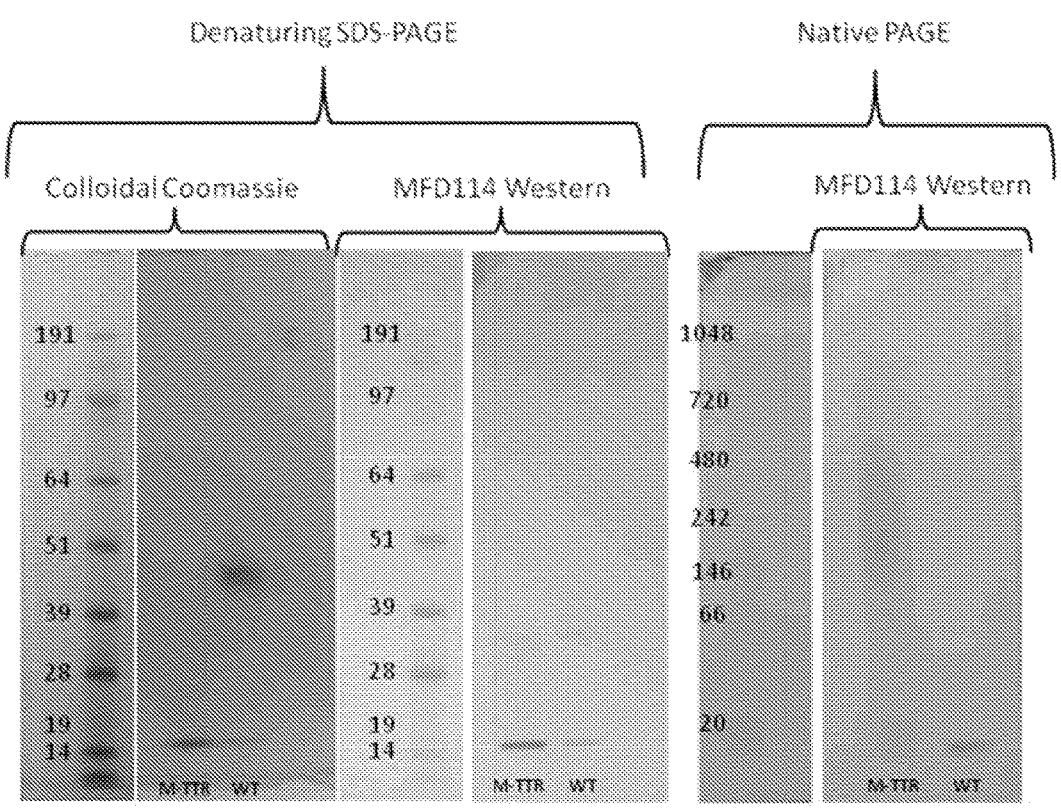
FIG. 11 depicts characterization of the non-native TTR using antibody MFD114.

FIG. 11 depicts the Colloidal Coomassie staining of non-native M-TTR and native WT TTR and corresponding western blot using the MFD114 antibody, under denaturing and native PAGE conditions, respectively. The Coomassie gel demonstrates that M-TTR after denaturation is mainly monomeric, and that WT-TTR is resistant to denaturation and mainly tetrameric. The corresponding MFD114 western blot demonstrates that MFD114 selectively recognizes monomeric TTR over tetrameric TTR. The native PAGE gel exhibits a high-molecular weight smear in the M-TTR lane, indicating that under non-denaturing PAGE conditions that oligomerized TTR are maintained and that MFD114 recognizes both oligomeric TTR and monomeric TTR (~14 kD band in the WT lane), but poorly recognizes tetrameric TTR. MFD114 also recognizes a species between the 28 kD and 39 kD marker, which likely corresponds to a dimeric form of misfolded TTR.

Example 13: Diagnosis of Cardiomyopathy Caused by TTR Amyloidosis

Senile systemic amyloidosis often presents with symptoms and histological hallmarks shared by other amyloidosis, for example, primary immunoglobulin light chain amyloidosis (AL), where the clinical presentations (echocardiographic findings, etc.) are very similar. Other biomarkers currently used in assisting the diagnosis of these diseases are non-specific where many different physiological and pathological events can affect the levels of the biomarkers. Sera samples were collected from 65 symptomatic cardiomyopathy patients including those believed to have SSA or AL. Samples were assayed for non-native 1TR using a sandwich ELISA as described herein. FIG. 9 depicts results from the 65 symptomatic cardiomyopathy patients, with the dotted line representing the plate cut point. Patients with non-native TTR levels above the plate cut point are considered positive in the assay and predicted to have cardiomyopathy caused by TTR amyloidosis. It is believed that many of the AL patients are potentially mis-diagnosed SSA (or FAC) patients or affected by TTR amyloidosis simultaneously. Additional curated SSA and AL samples are being tested to validate the diagnostic assay.

Figure 12:
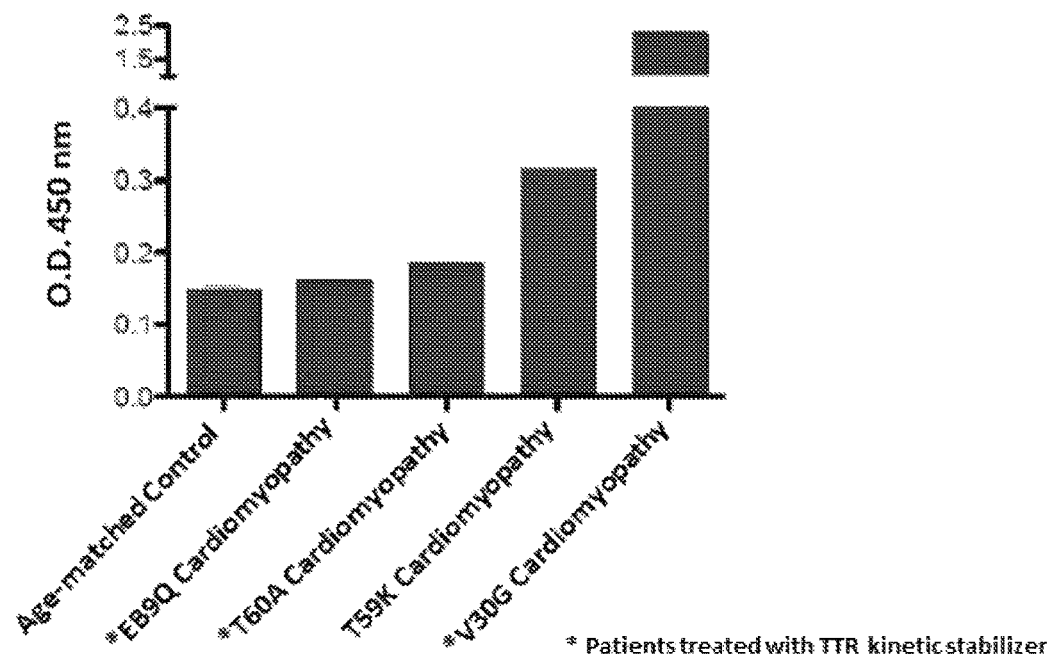
FIG. 12 depicts detection of non-native TTR in plasma from subjects with TTR mutations other than V30M mutations.

Example 14: Detection of Non-Native TTR in Human Subjects with TTR Mutations Other than V30M Mutations TTR-related amyloidoses are associated with a number of TTR mutations. While V30M and V122I mutations are commonly associated with TTR-related amyloidoses, other rare mutations (including but not limited to mutations described herein) are associated with amyloidoses related to, e.g., cardiomyopathy and polyneuropathy. To determine whether the subject antibodies detect non-native TTR in subjects with rare TTR mutations, plasma samples were collected from a 61 year old female cardiomyopathy patient heterozygous for a E89Q TTR mutation, undergoing treatment with a TTR kinetic stabilizer (n=1), a 57 year old male cardiomyopathy patient heterozygous for a T60A mutation, undergoing treatment with a 11K kinetic stabilizer (n=1), a 55 year old female cardiomyopathy patient heterozygous for a T59K mutation (n=1), 53 year old female cardiomyopathy patient heterozygous for a V30G mutation, undergoing treatment with a TTR kinetic stabilizer (n=1), and age-matched control subjects (n=10, 5 male and 5 female). Samples were collected and assayed for non-native TTR as described herein (see, e.g., Example 10). FIG. 12 depicts results from the non-native TTR assay. All mutations were associated with an increase in non-native TTR signal as compared to age-matched control subjects, indicating that the subject antibodies can detect non-native forms of rare mutant TTR.

Example 14: Effects of Tafamidis on Non-Native TTR in FAP Patients

Figure 13A:
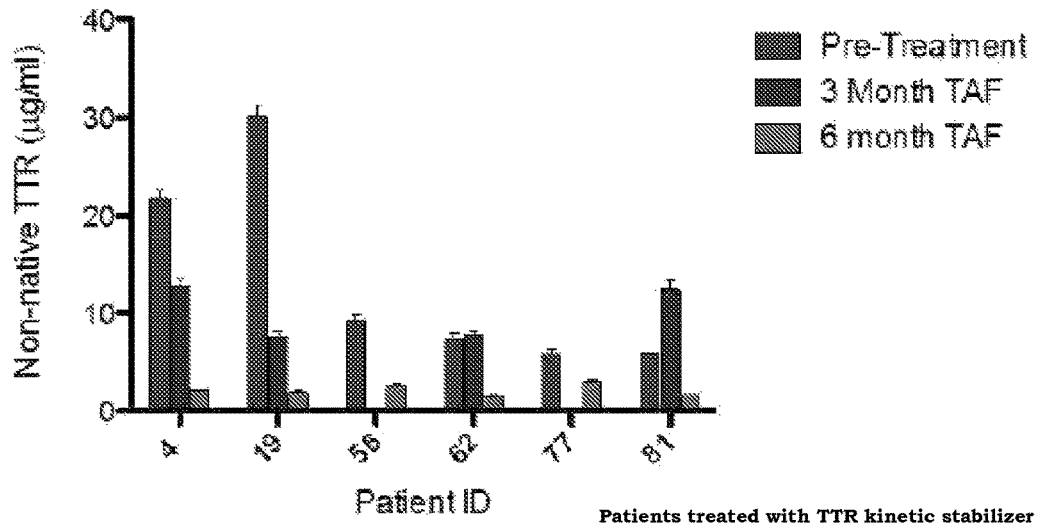
FIGS. 13A and 13B depict detection of non-native TTR in plasma from familial amyloid polyneuropathy patients before and during tafamidis treatment.

Tafamidis is a small molecule kinetic stabilizer of TTR. To determine the effects of tafamidis administration on non-native TTR in heterozygous V30M FAP patients, subjects were administered 20 mg/day tafamidis for 6 months. Plasma was collected from FAP patients before treatment, after 3 months of tafamidis treatment, and after 6 months of tafamidis treatment. Samples were collected and assayed for non-native TTR as described herein (see, e.g., Example 10). Non-native TTR levels were determined by comparison to a non-native TTR standard curve (data not shown). Non-native TTR standards were prepared as described in Example 2.1. FIG. 13A depicts results from the assay. Subjects exhibited varying levels of non-native TTR prior to tafamidis treatment. By 3 months of treatment, subjects 4, 19, 56, and 77 exhibited reduced levels of non-native TTR as compared to pre-treatment levels. By contrast, by 3 months of treatment subjects 62 and 81 exhibited similar or increased levels of non-native TTR as compared to pre-treatment levels. By 6 months of treatment, all treated patients exhibited reduced non-native TTR levels as compared to pre-treatment levels.

Figure 13B:
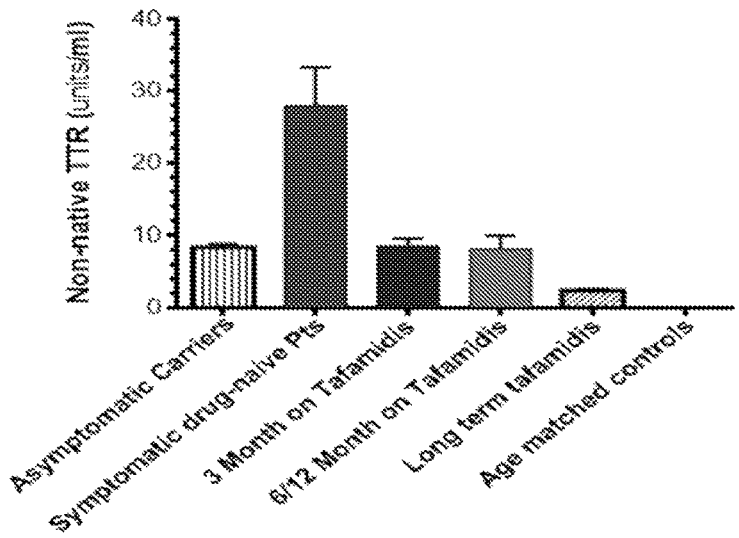

In a separate study, non-native TTR levels were assessed in 56 symptomatic heterozygous V30M FAP patients prior to tafamidis treatment, as well as asymptomatic carriers. Patients were administered 20 mg/day tafamidis. Non-native TTR levels were assessed in the same patients at 3 months, 6 months or 12 months post treatment. Furthermore, an additional 20 patients were treated with tafamidis 20 mg/day for greater than 24 months (e.g., long-term treatment group). FIG. 13B depicts results from the study. All V30M subjects (asymptomatic, symptomatic, and tafamidis-treated) exhibited detectable levels of non-native TTR, while age-matched controls exhibited no detectable levels of non-native TTR. These results indicate that the non-native TTR assay described herein is useful for early identification of FAP patients (e.g., for early identification of asymptomatic FAP patients). Furthermore, symptomatic FAP patients exhibited a marked increase in non-native TTR levels as compared to asymptomatic carriers. These results indicate that the non-native TTR assay can be used to biochemically differentiate symptomatic from asymptomatic patient groups. In addition, patients treated with tafamidis for 3, 6, 12, or over 24 months exhibited a reduction in non-native TTR levels, with the long-term treatment group exhibiting the greatest reduction in non-native TTR levels. This data indicates that the non-native TTR assay can be used to monitor response to TTR drug treatment.

Example 15: Chemiluminescent Assay for Non-Native TTR

Plasma samples from drug-naïve, symptomatic male and female heterozygous V30M TTR FAP patients (N=20) and age matched controls (N=12) were drawn by venipuncture into BD Vacutainer Cell Preparation Tubes (CPT) containing sodium citrate/Ficoll (Becton Dickinson #362782). Tubes were stored upright at room temperature for 30-45 minutes, mixed by inversion and then centrifuged for 20 minutes at 1500 RCF at room temperature. Plasma was carefully removed to avoid disturbing the mononuclear cell and platelet layer. Plasma was flash frozen and stored at −80° C. In a blinded fashion, plasma samples were analyzed by sandwich ELISA.

ELISA plates were prepared by coating with a TTR capture antibody, selected from Table 2, overnight at 4° C. in sodium carbonate/bicarbonate buffer, pH 9.6. Plates were blocked with plasma (pooled normal human plasma, Innovative Research) diluted 1/20 in Superblock (Pierce) for 1 hour at room temperature followed by incubation with plasma samples at 1/20 dilution in TBS for 2 hours at room temperature. The wells were then washed three times with TBST followed by a 1 hour incubation at room temperature with a 0.5 microgram/ml biotinylated anti-non-native TTR antibody (e.g., detection antibody) selected from Table 2 (diluted in Superblock+0.05% Tween-20). Wells were then washed 3× with TBST followed by incubation for 30 minutes at room temperature with Streptavidin-HRP conjugate (Invitrogen, 1/5,000 dilution in Superblock+0.05% Tween-20). After washing 3× with TBST, signal was detected with SuperSignal ELISA Pico Chemiluminescent Substrate (Pierce) and luminescence signal was detected with a Flex-Station 3 microplate reader (Molecular Devices). Non-native TTR levels in plasma samples were determined from recombinant non-native TTR standard curve (FIG. 14, panel A).

Figure 14:
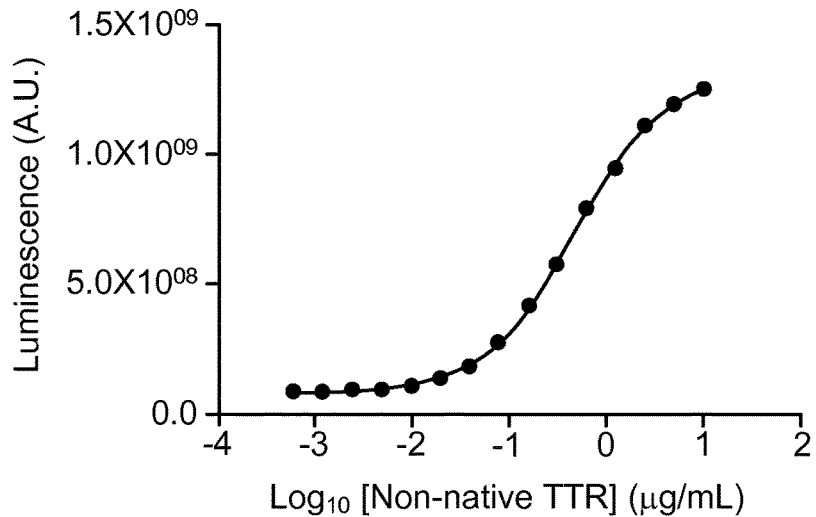
FIG. 14 depicts detection of non-native TTR in plasma from V30M heterozygous FAP carriers using an ELISA assay with chemiluminescent detection.
Figure 14:
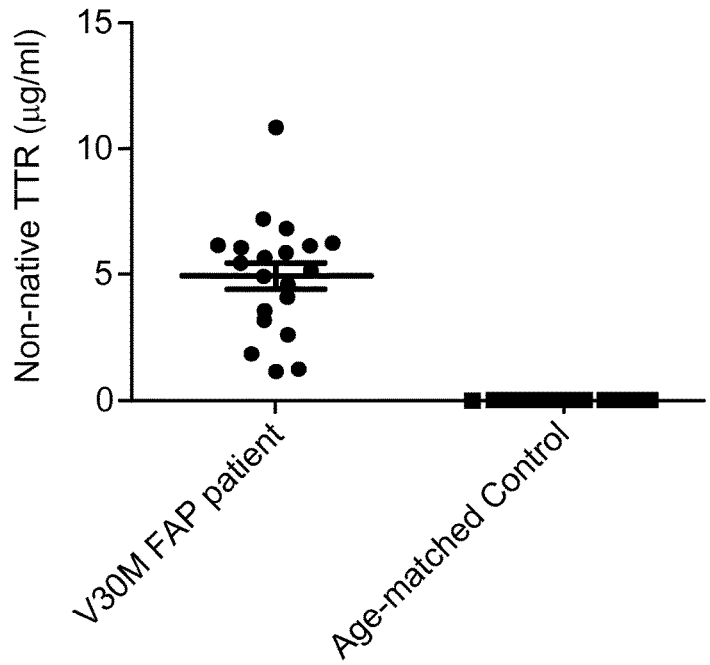

FIG. 14 depicts results from the non-native TTR assay with chemiluminescent detection. Panel A depicts luminescence readings generated from a non-native TTR standard curve, demonstrating detection of sub-nanogram to over 10 microgram amounts of non-native TTR/ml sample. Panel B depicts quantitation of non-native TTR in the V30M subjects vs. age-matched controls. V30M FAP patients exhibited non-native TTR levels that were significantly higher than age-matched control (Student's t-test, $p<0.001$).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An anti-transthyretin (TTR) monoclonal antibody that exhibits selective binding to non-native TTR under physiologically relevant conditions as compared to tetrameric TTR for said antibody binding, wherein the monoclonal antibody binds to an epitope consisting essentially of amino acid residues 49-61 or 109-121 in SEQ ID. No. 1 with a Kd equal to or less than 1 nM, wherein the epitope has a length of 10, 11, 12, 13, 14, 15, or 16 amino acids.

2. The antibody of claim 1, wherein said antibody binds to an epitope that is more accessible on non-native TTR as compared to tetrameric TTR, wherein epitope accessibility is evidenced by formation of an epitope/antibody complex in a binding assay.

3. The antibody of claim 1, wherein the monoclonal antibody binds to an epitope consisting essentially of amino acid residues 49-61 in SEQ ID. No 1.

4. The antibody of claim 1, wherein said antibody binds to wild-type monomeric and/or wild-type oligomeric TTR.

5. The antibody of claim 1, wherein said antibody binds to mutant monomeric and/or mutant oligomeric TTR.

6. The antibody of claim 1, wherein the monoclonal antibody binds to an epitope consisting essentially of amino acid residues 109-121 in SEQ ID. No 1.

7. The antibody of claim 1, wherein said antibody exhibits weaker binding to said epitope when TTR is in a native tetrameric conformation as compared to when TTR is in a non-native conformation.

8. The antibody of claim 7, wherein said weaker binding is ascertained by indirect ELISA.

9. The antibody of claim 1, wherein said monoclonal antibodies exhibit at least 100 times greater affinity towards the non-native TTR as compared to the tetrameric TTR.

10. The antibody of claim 9, wherein said antibody exhibits a Kd equal to or less than 1 nM, and wherein said monoclonal antibodies exhibit at least 100 times greater affinity towards the non-native TTR as compared to the tetrameric TTR.

11. A host cell that produces the antibody of claim 1.

12. The antibody of claim 1, wherein the antibody exhibits selective binding to a non-native form of mutant transthyretin (TTR) present in an amyloid disease carrier under physiologically relevant conditions as compared to a tetrameric form of said mutant TTR.

13. The antibody of claim 12, wherein said amyloid disease is familial amyloid neuropathy, familial amyloid cardiomyopathy, carpel tunnel syndrome, leptomeningeal amyloidosis, familial oculoleptomeningeal amyloidosis, or senile systemic amyloidosis.

14. The antibody of claim 12, wherein said mutant transthyretin comprises a mutation selected from the group consisting of a Cys10Arg mutation, a Leu12Pro mutation, an Asp18Glu mutation, an Asp18Gly mutation, an Asp18Asn mutation, a Val20Ile mutation, a Ser23Asn mutation, a Pro24Ser mutation, an Ala25Thr mutation, an Ala25Ser mutation, a Val28Met mutation, a Val30Met mutation, a Val30Ala mutation, a Val30Leu mutation, a Val30Gly mutation, a Val32Ala mutation, a Phe33Ile mutation, a Phe33Leu mutation, a Phe33Val mutation, a Phe33Cys mutation, an Arg34Thr mutation, an Arg34Gly mutation, a Lys35Asn mutation, a Lys35Thr mutation, an Ala36Pro mutation, an Asp38Ala mutation, an Asp38Val mutation, a Trp41Leu mutation, a Glu42Gly mutation, a Glu42Asp mutation, a Phe44Ser mutation, an Ala45Asp mutation, an Ala45Ser mutation, an Ala45Thr mutation, a Gly47Arg mutation, a Gly47Ala mutation, a Gly47Val mutation, a Gly47Glu mutation, a Thr49Ala mutation, a Thr49Ile mutation, a Thr49Pro mutation, a Ser50Arg mutation, a Ser50Ile mutation, a Glu51Gly mutation, a Ser52Pro mutation, a Gly53Glu mutation, a Gly53Ala mutation, a Glu54Gly mutation, a Glu54Lys mutation, a Glu54Leu mutation, a Leu55Arg mutation, a Leu55Pro mutation, a Leu55Gln mutation, a Leu55Glu mutation, a His56Arg mutation, a Gly57Arg mutation, a Leu58His mutation, a Leu58Arg mutation, a Thr59Lys mutation, a Thr60Ala mutation, a Glu61Lys mutation, a Glu61Gly mutation, a Phe64Leu mutation, a Phe64Ser mutation, a Gly67Glu mutation, a Ile68Leu mutation, a Tyr69His mutation, a Tyr69Ile mutation, a Lys70Asn mutation, a Val71Ala mutation, a Ile73Val mutation, a Ser77Phe mutation, a Ser77Tyr mutation, a Tyr78Phe mutation, an Ala81Val mutation, an Ala81Thr mutation, a Ile84Ser mutation, a Ile84Asn mutation, a Ile84Thr mutation, a His88Arg mutation, a Glu89Gln mutation, a Glu89Lys mutation, a His90Asp mutation, an Ala91Ser mutation, a Gln92Lys mutation, a Val94Ala mutation, an Ala97Gly mutation, an Ala97Ser mutation, an Arg103Ser mutation, a Ile107Val mutation, a Ile107Met mutation, a Ile107Phe mutation, an Ala109Ser mutation, a Leu111Met mutation, a Ser112Ile mutation, a Tyr114Cys mutation, a Tyr114His mutation, a Tyr116Ser mutation, an Ala120Ser mutation, a Val122Ile mutation, a DelVal122 mutation, a Val122Ala mutation, and an Asn124Ser mutation.

15. The antibody of any of claim 12, wherein said selective binding to said non-native TTR as compared to tetrameric TTR is evidenced by an increased amount of immunocomplexes formed between said antibody and said non-native TTR as compared to an amount of immunocomplexes formed between said antibody and said tetrameric TTR.

16. A homogenous population of monoclonal antibodies of claim 1.

17. A set of antibodies of claim 1, comprising a first antibody exhibiting selective binding to an epitope consisting essentially of amino acid residues 49-61 in SEQ ID. No. 1, and a second antibody exhibiting selective binding to an epitope consisting essentially of amino acid residues 109-121.

18. The antibody of claim 1, wherein the antibody is MFD108 produced by the hybridoma deposited with the American Type Culture Collection having the ATCC Patent Deposit Designation PTA-120816.

19. The set of antibodies of claim 17, wherein the first antibody is MFD108 produced by the hybridoma deposited with the American Type Culture Collection having the ATCC Patent Deposit Designation PTA-120816.

* * * * *

SEQUENCE LISTING

<160> NUMBER OF SEQ ID NOS: 13

<210> SEQ ID NO 1
<211> LENGTH: 127
<212> TYPE: PRT

<213> ORGANISM: Artificial sequence
<220> FEATURE:
<223> OTHER INFORMATION: Polypeptide

<400> SEQUENCE: 1

```
Gly Pro Thr Gly Thr Gly Glu Ser Lys Cys Pro Leu Met Val Lys Val
1               5                   10                  15
Leu Asp Ala Val Arg Gly Ser Pro Ala Ile Asn Val Ala Val His Val
            20                  25                  30
Phe Arg Lys Ala Ala Asp Asp Thr Trp Glu Pro Phe Ala Ser Gly Lys
        35                  40                  45
Thr Ser Glu Ser Gly Glu Leu His Gly Leu Thr Thr Glu Glu Glu Phe
    50                  55                  60
Val Glu Gly Ile Tyr Lys Val Glu Ile Asp Thr Lys Ser Tyr Trp Lys
65                  70                  75                  80
Ala Leu Gly Ile Ser Pro Phe His Glu His Ala Glu Val Val Phe Thr
                85                  90                  95
Ala Asn Asp Ser Gly Pro Arg Arg Tyr Thr Ile Ala Ala Leu Leu Ser
            100                 105                 110
Pro Tyr Ser Tyr Ser Thr Thr Ala Val Val Thr Asn Pro Lys Glu
        115                 120                 125
```

<210> SEQ ID NO 2
<211> LENGTH: 399
<212> TYPE: DNA
<213> ORGANISM: Artificial sequence
<220> FEATURE:
<223> OTHER INFORMATION: Polynucleotide

<400> SEQUENCE: 2

```
atgggatgga actggatctt tctctttctc ctgtcaggaa ctgcaggtgt cctctctgag    60
gtccacttgc aacagtctgg acctgagctg gtgaagcctg ggcttcagt gaagatatcc    120
tgcaagactt ctggataccc attcgctgaa tacaccattc actgggtgaa gcagagccat   180
ggagagagcc ttgagtggat tggaggtatt aatcctatca ctggtggtac tttctacaac   240
cagaagttca cggcaaggc cacattgact gttgacaggt cctccagcac agcctacatg   300
gacttccgca gcctgacatc tgaggattct gcagtctatt actgtgcaag aggggaaagg   360
acttactggg gccagggac tctggtcact gtctctgca                           399
```

<210> SEQ ID NO 3
<211> LENGTH: 133
<212> TYPE: PRT
<213> ORGANISM: Artificial sequence
<220> FEATURE:
<223> OTHER INFORMATION: Polypeptide

<400> SEQUENCE: 3

```
Met Gly Trp Asn Trp Ile Phe Leu Phe Leu Leu Ser Gly Thr Ala Gly
1               5                   10                  15
Val Leu Ser Glu Val His Leu Gln Gln Ser Gly Pro Glu Leu Val Lys
            20                  25                  30
Pro Gly Ala Ser Val Lys Ile Ser Cys Lys Thr Ser Gly Tyr Pro Phe
        35                  40                  45
Ala Glu Tyr Thr Ile His Trp Val Lys Gln Ser His Gly Glu Ser Leu
    50                  55                  60
Glu Trp Ile Gly Gly Ile Asn Pro Ile Thr Gly Gly Thr Phe Tyr Asn
65                  70                  75                  80
```

Gln Lys Phe Asn Gly Lys Ala Thr Leu Thr Val Asp Arg Ser Ser Ser
                 85                  90                  95

Thr Ala Tyr Met Asp Phe Arg Ser Leu Thr Ser Glu Asp Ser Ala Val
            100                 105                 110

Tyr Tyr Cys Ala Arg Gly Glu Arg Thr Tyr Trp Gly Gln Gly Thr Leu
        115                 120                 125

Val Thr Val Ser Ala
    130

<210> SEQ ID NO 4
<211> LENGTH: 408
<212> TYPE: DNA
<213> ORGANISM: Artificial sequence
<220> FEATURE:
<223> OTHER INFORMATION: Polynucleotide

<400> SEQUENCE: 4
atgaacttcg ggctcagctt gattttcctt gccctcattt taaaaggtgt ccagtgtgag      60
gtgcagctgg tggagtctgg gggagactta gtgaagcctg agggtccct gaaactctcc     120 tgtgcagcct ctggattcac tttcagtaac tatggcatgt cttgggttcg ccagactcca    180
gacaagaggc tggagtgggt cgcaaccatt actagtggtg gtagttacac ctactatcca    240
gacagtgtga agggcgatt caccatctcc agagacaatg ccagaacac cctgtacctg      300 caaatgagca gtctgaagtc tgaggacaca gccatgtatt actgtgcaag agatgggacc    360
gcctggtttg cttactgggg ccaagggact ctggtcactg tctctgca                 408

<210> SEQ ID NO 5
<211> LENGTH: 136
<212> TYPE: PRT
<213> ORGANISM: Artificial sequence
<220> FEATURE:
<223> OTHER INFORMATION: Polypetide

<400> SEQUENCE: 5

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Asn Tyr Gly Met Ser Trp Val Arg Gln Thr Pro Asp Lys Arg Leu
    50                  55                  60

Glu Trp Val Ala Thr Ile Thr Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Asp Gly Thr Ala Trp Phe Ala Tyr Trp Gly Gln
        115                 120                 125

Gly Thr Leu Val Thr Val Ser Ala
    130                 135

<210> SEQ ID NO 6
<211> LENGTH: 411
<212> TYPE: DNA
<213> ORGANISM: Artificial sequence
<220> FEATURE:

<223> OTHER INFORMATION: Polynucleotide

<400> SEQUENCE: 6

```
atggaatgga gttggatatt tctctttctc ctgtcaggaa ctgcaggtgt ccactctgag      60
gtccagctgc agcagtctgg acctgagctg gtaaagcctg ggcttcagt gaagatgtcc     120
tgcaaggctt ctggatacac attcactagc tttcttatgc actgggtgaa gcagaagcct    180
gggcagggcc ttgagtggat tggatatatt aatccttaca atgatggtac taagtacaat    240
gagaagttca aggcaaggc cacactgact tcagccaaat cctccagcac agcctacatg     300
gagctcagca gcctgacctc tgaggactct gcggtctatt actgtgcaag agagaaggga    360
tggttatctc ttgcttactg gggccaaggg actctggtca ctgtctctgc a             411
```

<210> SEQ ID NO 7
<211> LENGTH: 137
<212> TYPE: PRT
<213> ORGANISM: Artificial sequence
<220> FEATURE:
<223> OTHER INFORMATION: Polypeptide

<400> SEQUENCE: 7

```
Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Phe Leu Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Ala Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Glu Lys Gly Trp Leu Ser Leu Ala Tyr Trp Gly
        115                 120                 125

Gln Gly Thr Leu Val Thr Val Ser Ala
    130                 135
```

<210> SEQ ID NO 8
<211> LENGTH: 393
<212> TYPE: DNA
<213> ORGANISM: Artificial sequence
<220> FEATURE:
<223> OTHER INFORMATION: Polynucleotide

<400> SEQUENCE: 8

```
atgaagttgc ctgttaggct gttggtgctg atgttctgga ttcctgtttc cagcagtgat      60
gtcttgatga cccaaactcc actctcctg cctgtcagtc ttggagatca gtttccatc      120
tcttgcagat ctagtcagag cattgtacgt agtaatggaa acacctattt agaatggtat     180
ctgcagaaac caggccagtc tccaaagctc ctgatctaca agtttccaa ccgattttct      240
ggggtcccag acaggttcag tggcagtgga tcaggacag atttcacact caagatcagc      300
agagtggagg ctgaggatct gggagtttat tactgctttc aaggttcaca tgttcctcct     360
acgttcggtg ctgggaccaa gctggagctg aaa                                  393
```

<210> SEQ ID NO 9
<211> LENGTH: 131
<212> TYPE: PRT
<213> ORGANISM: Artificial sequence
<220> FEATURE:
<223> OTHER INFORMATION: Polypeptide

<400> SEQUENCE: 9

```
Met Lys Leu Pro Val Arg Leu Leu Val Leu Met Phe Trp Ile Pro Val
1               5                   10                  15

Ser Ser Ser Asp Val Leu Met Thr Gln Thr Pro Leu Ser Leu Pro Val
            20                  25                  30

Ser Leu Gly Asp Gln Val Ser Ile Ser Cys Arg Ser Ser Gln Ser Ile
        35                  40                  45

Val Arg Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Pro Thr Phe Gly Ala Gly Thr Lys Leu
        115                 120                 125

Glu Leu Lys
    130
```

<210> SEQ ID NO 10
<211> LENGTH: 378
<212> TYPE: DNA
<213> ORGANISM: Artificial sequence
<220> FEATURE:
<223> OTHER INFORMATION: Polynucleotide

<400> SEQUENCE: 10

```
atgatgtcct ctgctcagtt cctttggtctc ctgttgctct gttttcaagg taccagatgt    60
gatatccaga tgacacagac tacatcctcc ctgtctgcct ctctgggaga cagagtcacc   120
atcagttgca gggcaagtca ggacattagc aattatttaa actggtatca gcagaaacca   180
gatggaactg ttaaactcct gatctactac acatcaagat tacactctgg agtcccatca   240
cggttcagtg gcagtgggtc tggaacagat tattctctca ccattagcaa cctggaggaa   300
gaagatattg ccacttactt ttgccaacag ggtaatacgc ttcggacgtt cggtggaggc   360
accaagctgg agatcaaa                                                  378
```

<210> SEQ ID NO 11
<211> LENGTH: 126
<212> TYPE: PRT
<213> ORGANISM: Artificial sequence
<220> FEATURE:
<223> OTHER INFORMATION: Polypeptide

<400> SEQUENCE: 11

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45
```

Ile Ser Asn Tyr Leu Asn Trp Tyr Gln Gln Lys Pro Asp Gly Thr Val
 50                  55                  60

Lys Leu Leu Ile Tyr Tyr Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
                 85                  90                  95

Asn Leu Glu Glu Glu Asp Ile Ala Thr Tyr Phe Cys Gln Gln Gly Asn
            100                 105                 110

Thr Leu Arg Thr Phe Gly Gly Gly Thr Lys Leu Glu Ile Lys
        115                 120                 125

<210> SEQ ID NO 12
<211> LENGTH: 390
<212> TYPE: DNA
<213> ORGANISM: Artificial sequence
<220> FEATURE:
<223> OTHER INFORMATION: Polynucleotide

<400> SEQUENCE: 12
atggattttc agatgcagat tatcagcttg ctgctaatca gtgtcacagt cataatgtct      60
aatggagaaa ttgtgctcac ccagtctcca accaccatgg ctgcatctcc cggggagaag    120
atcactatca cctgcagtgc cagctcaagt ttaagttcca attacttgca ttggtatcag    180
cagaagccag gattctcccc taaactcttg atttatagga catccaatct gggttctgga    240
gtcccagctc gcttcagtgg cagtgggtct gggacctctt actctctcac aattggcacc    300
atggaggctg aagatgttgc cacttactac tgccagcagg gtagtagtat accacgcacg    360
ttcggtgctg ggaccaagct ggagctgaga                                     390

<210> SEQ ID NO 13
<211> LENGTH: 130
<212> TYPE: PRT
<213> ORGANISM: Artificial sequence
<220> FEATURE:
<223> OTHER INFORMATION: Polypeptide

<400> SEQUENCE: 13

Met Asp Phe Gln Met Gln Ile Ile Ser Leu Leu Leu Ile Ser Val Thr
  1               5                  10                  15

Val Ile Met Ser Asn Gly Glu Ile Val Leu Thr Gln Ser Pro Thr Thr
             20                  25                  30

Met Ala Ala Ser Pro Gly Glu Lys Ile Thr Ile Thr Cys Ser Ala Ser
         35                  40                  45

Ser Ser Leu Ser Ser Asn Tyr Leu His Trp Tyr Gln Gln Lys Pro Gly
 50                  55                  60

Phe Ser Pro Lys Leu Leu Ile Tyr Arg Thr Ser Asn Leu Gly Ser Gly
 65                  70                  75                  80

Val Pro Ala Arg Phe Ser Gly Ser Gly Ser Gly Thr Ser Tyr Ser Leu
                 85                  90                  95

Thr Ile Gly Thr Met Glu Ala Glu Asp Val Ala Thr Tyr Tyr Cys Gln
            100                 105                 110

Gln Gly Ser Ser Ile Pro Arg Thr Phe Gly Ala Gly Thr Lys Leu Glu
        115                 120                 125

Leu Arg
130